United States Patent [19]

Moser et al.

[11] 4,202,816
[45] May 13, 1980

[54] NOVEL LIGHT STABILIZERS

[75] Inventors: Paul Moser, Riehen; Jean Rody, Basel, both of Switzerland

[73] Assignee: Ciba-Geigy Corporation, Ardsley, N.Y.

[21] Appl. No.: 849,156

[22] Filed: Nov. 7, 1977

Related U.S. Application Data

[63] Continuation-in-part of Ser. No. 696,962, Jun. 17, 1976, abandoned.

[30] Foreign Application Priority Data

Jun. 19, 1975 [CH] Switzerland .................. 7989/75
Dec. 2, 1975 [CH] Switzerland .................. 15651/75
Mar. 18, 1976 [CH] Switzerland .................. 3407/76

[51] Int. Cl.$^2$ .................. C08K 5/54; C08K 5/34; C07D 211/06
[52] U.S. Cl. .................. 260/45.75 N; 260/45.8 N; 260/45.8 A; 260/45.75 R
[58] Field of Search ......... 260/270 R, 270 PD, 270 J, 260/293.76, 293.63, 45.75, 45.8 N, 293.64, 293.65, 293.73, 293.66, 293.58, 294.8 F, 293.76, 45.8 H

[56] References Cited

U.S. PATENT DOCUMENTS

| | | | |
|---|---|---|---|
| 2,984,634 | 5/1961 | Caldwell et al. | 260/23 H |
| 3,188,293 | 6/1965 | Williamson et al. | 260/23 H |
| 3,189,630 | 6/1965 | Smutny | 260/45.75 N |
| 3,464,943 | 9/1969 | Newland et al. | 260/23 H |
| 3,464,953 | 9/1969 | Newland | 260/45.75 N |
| 3,640,928 | 2/1972 | Murayama et al. | 260/24 XA |
| 3,745,163 | 7/1973 | Holt et al. | 260/293.76 |
| 3,790,525 | 2/1974 | Murayama et al. | 260/45.8 NZ |
| 3,853,890 | 12/1974 | Holt | 260/293.63 |
| 3,859,293 | 1/1975 | Murayama et al. | 260/45.8 NP |
| 3,899,464 | 8/1975 | Murayama et al. | 260/45.8 NP |
| 3,904,581 | 9/1975 | Murayama et al. | 260/45.8 NP |
| 3,933,735 | 1/1976 | Murayama et al. | 260/45.8 NP |
| 3,939,168 | 2/1976 | Cook | 260/45.8 NZ |
| 3,940,363 | 2/1976 | Murayama et al. | 260/45.75 N |
| 3,948,852 | 4/1976 | Rasberger et al. | 260/45.75 N |
| 3,954,779 | 5/1976 | Smith et al. | 260/45.8 NP |
| 3,992,390 | 11/1976 | Holt et al. | 260/45.8 N |
| 3,993,655 | 11/1976 | Rasberger et al. | 260/45.8 N |
| 4,026,866 | 5/1977 | Rasberger et al. | 260/45.75 N |
| 4,046,788 | 9/1977 | Rasberger et al. | 260/45.75 N |
| 4,052,361 | 10/1977 | Susi et al. | 260/45.8 NA |
| 4,061,616 | 12/1977 | Murayama et al. | 260/45.8 NP |

*Primary Examiner*—V. P. Hoke
*Attorney, Agent, or Firm*—Wenderoth, Lind & Ponack

[57] ABSTRACT

Novel light stabilizers, i.e. metal complexes of formula I

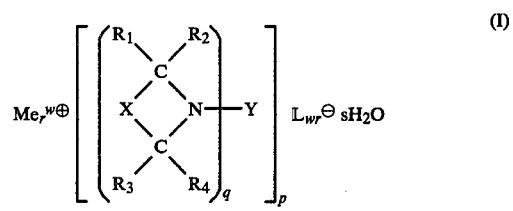

wherein
Me is a doubly or triply positively charged metal ion,
w is 2 or 3,
p is 1 or 2,
q is 1 or 2,
r is equal to the number, to half the number or to a quarter of the number of the >N-Y groups present within the bracket q,
$R_1$, $R_2$, $R_3$ and $R_4$ independently of one another are alkyl, or
$R_1$ and $R_3$ together are alkylene, or
$R_1$ and $R_2$ or $R_3$ and $R_4$, independently of one another, together are alkylene or azaalkylene,
and, if q is 1,
Y is hydrogen, oxyl, optionally substituted alkyl, alkenyl, alkynyl or aralkyl,
or, if q is 2,
Y is alkylene, alkenylene, alkynylene or arylenedialkylene,
s is a value from 0 to 2,
X is a divalent organic radical which supplements the N-containing ring to form a 5–7-membered ring, or is two monovalent organic radicals, and
L is a singly charged anion of an aliphatic carboxylic acid, of an aminophosphinic or aminophosphonic acid or of an enol of formula II

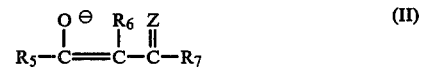

wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxycarbonyl, or $R_5$ and $R_6$ together are optionally substituted 1,4-butadi-1,3-enylene or 1,4-butylene, and $R_7$ is optionally substituted alkyl, alkenyl, cycloalkyl, aralkyl, aryl, alkoxy or optionally substituted amino.

57 Claims, No Drawings

NOVEL LIGHT STABILIZERS

CROSS-REFERENCE TO RELATED APPLICATION

This is a continuation-in-part application of our co-pending application Ser. No. 696,962, filed June 17, 1976, now abandoned.

SUMMARY OF THE INVENTION

The invention relates to novel metal complexes with sterically hindered amines and singly charged anions, to their manufacture and to their use as stabilisers for synthetic polymers, as well as to the material stabilised by means of them.

There have been repeated descriptions in recent years of sterically hindered amines as stabilisers for synthetic polymers, for instance in the following literature:

| | | | | | |
|---|---|---|---|---|---|
| GB-PS | 1.325.774 | GB-PS | 1.202.299 | DT-OS | 2.326.010 |
| GB-PS | 1.325.775 | US-PS | 3.547.874 | DT-OS | 2.338.076 |
| US-PS | 3.853.890 | US-PS | 3.542.729 | DT-OS | 2.349.962 |
| GB-PS | 1.329.847 | US-PS | 3.639.409 | JA-OS | 49-60337 |
| US-PS | 3.769.259 | US-PS | 3.640.928 | DT-OS | 2.352.606 |
| DT-OS | 2.257.997 | US-PS | 3.790.525 | JA-OS | 49-63738 |
| US-PS | 3.847.930 | US-PS | 3.862.155 | DT-OS | 2.352.538 |
| DT-OS | 2.258.086 | DT-OS | 2.030.908 | DT-OS | 2.353.539 |
| GB-PS | 1.365.319 | DT-OS | 2.040.983 | DT-OS | 2.258.368 |
| DT-OS | 2.258.752 | GB-PS | 1.262.234 | JA-OS | 49-72332 |
| DT-OS | 2.319.816 | DT-OS | 2.047.846 | JA-OS | 49-77944 |
| DT-OS | 2.337.822 | DT-OS | 2.040.975 | JA-OS | 48-65179 |
| DT-OS | 2.337.847 | US-PS | 3.840.494 | DT-OS | 2.425.984 |
| DT-OS | 2.337.796 | US-PS | 3.839.273 | DT-OS | 2.433.639 |
| US-PS | 3.850.877 | US-PS | 3.859.293 | DT-OS | 2.453.174 |
| DT-OS | 2.314.105 | JA-PS | 559.160 | DT-OS | 2.418.540 |
| DT-OS | 2.314.091 | JA-PS | 591.467 | | |
| DT-OS | 2.314.115 | JA-PS | 600.042 | | |
| DT-OS | 2.315.042 | JA-PS | 600.043 | | |
| DT-OS | 2.315.245 | JA-PS | 694.198 | | |
| DT-OS | 2.321.526 | JA-PS | 640.258 | | |
| DT-OS | 2.351.865 | JA-PS | 640.259 | | |
| DT-OS | 2.352.379 | JA-PS | 640.260 | | |
| DT-OS | 2.352.658 | JA-PS | 652.775 | | |
| DT-OS | 2.402.636 | JA-PS | 652.776 | | |
| DT-OS | 2.415.818 | JA-PS | 720.111 | | |
| DT-OS | 2.425.425 | JA-PS | 659.579 | | |
| DT-OS | 2.427.853 | DT-OS | 2.227.689 | | |
| DT-OS | 2.428.877 | US-PS | 3.829.404 | | |
| DT-OS | 2.435.170 | DT-OS | 2.304.374 | | |
| US-PS | 3.536.722 | DT-OS | 2.233.122 | | |
| GB-PS | 1.202.298 | DT-OS | 2.327.717 | | |

Such sterically hindered amines stabilise polymers, e.g. polyolefins such as polypropylene, against degradation caused by UV irradiation. As is customary in many cases of stabilisation of polymers, the said sterically hindered amines may be used on their own or together with other stabilisers, e.g. with antioxidants, UV absorbers, light stabilisers, metal deactivators, phosphites, compounds decomposing peroxide, polyamide stabilisers, basic Co-stabilisers, PVC stabilisers, nucleating agents, and so forth, whereby there are mentioned as light stabilisers, in addition to many other nickel complexes of 2,2'-thio-bis-[4-(1,1,3,3-tetramethylbutyl)-phenol], optionally with additional ligands such as n-butylamine: nickel complexes of bis-[2-hydroxy-4-(1,1,3,3-tetramethylbutyl)-phenyl]-sulphone, optionally with additional ligands such as 2-ethylcapronic acid, and nickel salts of 4-hydroxy-3,5-di-tert.butylbenzyl-phosphonic acid monoalkyl esters, such as of ethyl ester; as well as nickel-3,5-di-tert.-butyl-4-hydroxybenzoate (see, e.g., the aforementioned DT-OS No. 2,427,853).

It has now been found that metal complexes with sterically hindered amines and specific anions according to the invention display an appreciably better light-stabilising activity in polymers than could have been anticipated on the basis of the individual constituents. These advantageous properties are accompanied by a good prolongation of the stabilising action and by extraction stability in the polymer and also by good compatibility therein, so that the novel complex compounds are excellently suitable for stabilising polymers against UV decomposition. Whereas there occurs with the anions according to the invention a synergistic effect with regard to the light-stabilising action, that is to say, the stabilising action is greater than that resulting from the sum of the effects of the individual constituents, there occurs no synergistic effect in the case of the known combinations of sterically hindered amines with the nickel complexes given in the prior art, e.g. the combination of the sterically hindered amine with the nickel complex of 2,2'-thio-bis[4-(1,1,3,3-tetramethylbutyl)-phenol], with the nickel complex of bis-[2-hydroxy-4-(1,1,3,3-tetramethylbutyl)-phenyl]-sulphone, or with the nickel complex of 4-hydroxy-3,5-di-tert.-butyl-benzylphosphonic acid monoethyl ester, as can be seen from the comparative examples. The stabilisers according to the invention were therefore not rendered obvious by the prior art.

The metal complexes according to the invention correspond to formula I

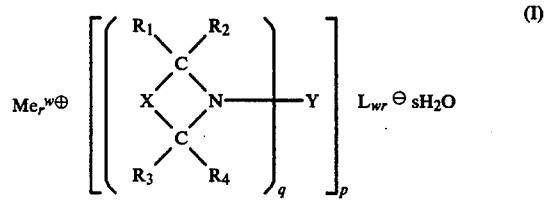

wherein
Me is a doubly or triply positively charged metal ion,
w is 2 or 3,
P is 1 or 2,
q is 1 or 2,
r is equal to the number, to half the number or to a quarter of the number of the >N-Y groups present within the bracket q,
$R_1$, $R_2$, $R_3$ and $R_4$ independently of one another are alkyl, or
$R_1$ and $R_3$ together are alkylene, or
$R_1$ and $R_2$ or $R_3$ and $R_4$, independently of one another, together are alkylene or azaalkylene,
and, if q is 1,
Y is hydrogen, oxyl, optionally substituted alkyl, alkenyl, alkynyl or aralkyl,
or, if q is 2,
Y is alkylene, alkenylene, alkynylene or arylenedialkylene,
s is a value from 0 to 2,
X is a bivalent organic radical which supplements the N-containing ring to form a 5-7-membered ring, or is two monovalent organic radicals, and
L is a singly charged anion of an aliphatic carboxylic acid, of an aminophosphinic or aminophosphonic acid or of an enol of formula II

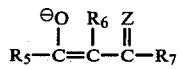

(II)

wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxycarbonyl, or $R_5$ and $R_6$ together are optionally substituted 1,4-butadi-1,3-enylene or 1,4-butylene, and $R_7$ is optionally substituted alkyl, alkenyl, cycloalkyl, aralkyl, aryl, alkoxy or optionally substituted amino.

Me as doubly positively charged metal ion is, in particular, such an ion of magnesium, calcium, strontium, barium, cadmium or VO, namely $VO^{2+}$, and especially of manganese, zinc, cobalt and more especially of nickel. As a triply positively charged metal ion, Me is in particular such an ion of chromium and especially of aluminium.

p is in particular 1, and q is in particular 1.

r corresponds to the whole number, to half the number or to a quarter of the number of sterically hindered amine groups, and is preferably 1 or 2.

$R_1$, $R_2$, $R_3$ and $R_4$ as alkyl, independently of one another, are in particular alkyl having 1-6 C atoms, preferably ethyl and more especially methyl.

As alkylene, $R_1$ and $R_3$ together are, in particular, alkylene having 1-6 C atoms, especially methylene or ethylene.

$R_1$ and $R_2$ or $R_3$ and $R_4$ together as alkylene are, in particular, straight-chain or branched-chain alkylene having 4-8 C atoms, especially pentamethylene; and as azaalkylene they are in particular straight-chain or branched-chain azaalkylene having 4-16, especially 4-10, C atoms, which can be substituted on the N atom, particularly by a monovalent radical Y, especially by alkyl such as alkyl having 1-6 C atoms, particularly methyl; or is in particular unsubstituted on the N atom, such as 3-aza-pentamethylene, and especially 2,2,4,4-tetramethyl-3-azo-pentamethylene, 2,2,3,4,4-pentamethyl-3-azo-pentamethylene, or the N-oxyl of 2,2,4,4-tetramethyl-3-aza-pentamethylene. Preferably only one of the pairs $R_1/R_2$ and $R_3/R_4$ is alkylene or azaalkylene, and the other is in each case alkyl; and in particular all the radicals $R_1$, $R_2$, $R_3$ and $R_4$ are alkyl.

Y as alkyl is in particular alkyl having 1-8 C atoms, preferably α-unbranched, especially that having 1-4 C atoms, and more especially methyl.

As substituted alkyl, Y is in particular halogenoalkyl having preferably 1-5 C atoms, especially 2-4 C atoms, wherein halogen is, e.g., bromine, and especially chlorine, such as 2-chloroethyl, 2-bromoethyl, 2-chloro-n-propyl, 3-bromo-n-propyl and 4-chloro-n-butyl, or cyanoalkyl having preferably a total of 2-6 C atoms, such as 2-cyanoethyl, 2-cyano-n-propyl, 3-cyano-n-propyl or 4-cyano-n-pentyl, or epoxyalkyl having preferably 3-5 C atoms, such as 2,3-epoxy-3-methyl-propyl, 3,4-epoxy-n-butyl, 4,5-epoxy-n-pentyl and, in particular, 2,3-epoxy-propyl, or hydroxyalkyl preferably having 2-5 C atoms and two, or especially one, hydroxy groups, such as 2,3-dihydroxy-n-propyl, 2-hydroxy-ethyl, 2-hydroxy-n-propyl, 3-hydroxy-n-propyl, 2-hydroxy-n-butyl and 4-hydroxy-n-pentyl, or acyloxyalkyl such as alkanoyloxyalkyl having a total of preferably 4-23 C atoms, such as 2-acetoxyethyl, 2-acetoxy-n-propyl, 3-acetoxy-n-propyl, 4-propionyloxy-n-butyl, 4-propionyloxy-n-pentyl and 2-octadecanoyloxyethyl, or such as alkylcarbamoyloxyalkyl having a total of preferably 4-7 C atoms, such as 2-methylcarbamoyloxy-ethyl and 2-ethyl-carbamoyloxy-ethyl, or such as arylcarbamoyloxyalkyl having a total preferably of 9-13 C atoms, such as 2-phenylcarbamoyl-oxy-ethyl, or such as alkylthiocarbamoyloxyalkyl having a total preferably of 4-7 C atoms, such as 2-methylthiocarbamoyloxy-ethyl, or alkoxycarbonylalkyl having a total preferably of 3-23 C atoms, such as 2-methoxycarbonylethyl, 2-ethoxycarbonylethyl, 2-n-butoxycarbonylethyl, n-hexyloxycarbonylmethyl, 3-methoxycarbonyl-n-propyl, 2-n-dodecyloxycarbonylethyl, 2-n-octadecyloxycarbonyl-ethyl and 2-eicosyloxycarbonyl ethyl, or alkoxyalkyl having a total preferably of 3-20 C atoms, such as 2-methoxyethyl, 2-ethoxyethyl, 2-n-propoxyethyl, 3-methoxy-n-propyl, 2-n-butoxyethyl, 4-methoxy-n-pentyl, 2-n-octoxyethyl, 2-n-dodecyloxyethyl and 2-n-octadecyloxyethyl, or cycloalkylalkyl having a total preferably of 6-20 C atoms, such as cyclohexylmethyl.

As alkenyl, Y is in particular alkenyl having 3-12, especially 3-6, C atoms, such as allyl, methallyl, n-hex-3-enyl, n-oct-4-enyl and n-undec-10-enyl.

As alkynyl, Y is in particular alkynyl having 3-6 C atoms, such as propargyl, n-but-1-ynyl, but-2-ynyl and n-hex-1-ynyl.

As aralkyl, Y is in particular aralkyl having a total of 7-12 C atoms, such as naphthyl-1-methyl and especially benzyl, which is optionally substituted such as by halogen, alkyl having particularly 1-6 C atoms, such as methyl, or methoxy having 1-6 C atoms, such as methoxy.

As alkylene, Y is in particular alkylene having 1-18 C atoms, preferably straight-chained, such as methylene, ethylene, propylene, butylene, hexylene, octylene, dodecylene and octadecylene.

As alkenylene, Y is in particular alkenylene having 4-8 C atoms, such as 1,4-but-2-enylene.

As alkynylene, Y is in particular alkynylene having 4-8 C atoms, such as 1,4-but-2-inylene.

As arylenedialkylene, Y is in particular arylenedialkylene having a total of 8-12 C atoms, especially phenylenedialkylene optionally alkylated, such as methylated, in the phenyl moiety, such as p-phenylenedimethylene, p-phenylenediethylene and dimethyl-p-phenylenedimethylene.

The bivalent organic radical X which supplements the N-containing ring to form a 5-7 -membered ring is preferably an optionally substituted radical of the following type: alkylene, especially trimethylene, alkenylene, especially propenylene, azaalkylene especially 1-aza-dimethylene, 2-aza-trimethylene and 2-aza-tetramethylene, and thiaalkylene, particularly 2-thia-2,2-dioxo-trimethylene.

Optionally substituted trimethylene X is, for example, unsubstituted trimethylene or trimethylene carrying one or more of the following substituents: in 1- and/or 3-position: alkyl having 1-5 C atoms, alkenyl having 3 or 4 C atoms, alkynyl having 3 or 4 C atoms, or aralkyl having 7 or 8 kC atoms, and/or in 2-position: optionally esterified or etherified hydroxy, or simultaneously OH and a 4-piperidyl, or optionally 1- and/or 3-substituted 1,3-bis-aza-2,4-dioxo-tetramethylene, or optionally substituted 4-hydroxy-cyclohexyl, or optionally 1-alkylated 2-hydroxyethyl, or optionally substituted methyl carrying an optionally functionally modified carboxyl group, or optionally substituted methylene carrying an optionally functionally modified carboxyl group, or aryl, or optionally 3-substituted 1-oxa-3-azatetramethylene carrying in the 2-position oxo or thioxo and in the 4-position oxo or imino, or 1,5dicyano-2,4-dioxo-3-aza-pentamethylene, or 1,5-dicarbamoyl-2,4-dioxo-3-aza-pentamethylene, or simultaneously OH and esterified —P(O)(OH)$_2$, or acylamino or ketalised oxo.

In the 1- and/or 3-position, alkyl as substituent of trimethylene X is, for example, ethyl iso-propyl, iso-butyl, n-pentyl or, in particular, methyl, and alkenyl e.g. allyl, methallyl or 2-butenyl, and alkynyl, e.g. propargyl, and aralkyl, e.g. phenethyl, α-methylbenzyl or especially benzyl.

Optionally esterified hydroxyl as substituent in the 2-position of trimethylene X is, e.g., free hydroxyl or hydroxyl which is esterified with an organic or inorganic acid carrying at least one hydroxyl group, as is explained further on in the test.

Esterified hydroxyl as substituent in the 2-position of trimethylene X is, in particular, a radical, bound by way of oxygen, of an optionally substituted hydrocarbon, as is explained further on in the text.

4-Piperidyl as substituent in the 2-position of trimethylene X, whereby simultaneously an OH group is bound in the 2-position, is, in particular, optionally N-substituted 2,2,6,6-tetramethyl-4-hydroxy-4-piperidyl, as is explained further on in the text.

Optionally 1- and/or 3-substituted 1,3-bisaza-2,4-dioxo-tetramethylene as substituent in the 2-position of trimethylene X is, in particular, that wherein the 1-position is substituted by methyl, ethyl, or allyl, or is especially unsubstituted, and the 3-position is unsubstituted or is substituted by an optionally substituted hydrocarbon radical, as is esplained further on in the text.

Optionally substituted 4-hydroxy-cyclohexyl as substituent in the 2-position of trimethylene X is, in particular, that which carries in one or more of the positions 2, 3, 5 and 6 hydrogen, or alkyl having 1–9 C atoms, such as methyl, ethyl, n-propyl, iso-propyl, sec-butyl, tert-butyl, sec-amyl, tert-amyl, 1,1-dimethylbutyl, 2-n-octyl or iso-nonyl, or cyclolkyl or alkylcycloalkyl having 5–14 C atoms, such as 1-methylcyclohexyl, cyclooctyl, cyclododecyl or adamantyl, especially cyclohexyl, or cycloalkylalkyl having 7–14 C atoms, such as cyclohexyl-octyl, cyclohexyl-hexyl or, in particular, cyclohexyl-methyl or 2-cyclohexyl-prop-2-yl, whereby the 4-hydroxyl group is unsubstituted or is substituted and represents one of the following groups: alkoxy having 1–20 C atoms, particularly 1–12 C atoms, such as methoxy or ethoxy, hydroxyalkoxy having 1–20, especially 1–12, C atoms, such as 2-hydroxyethoxy, or cyano-alkoxy having 2–20, particularly 2–12, C atoms, such as 2-cyanoethyl.

Optionally 1-alkylted 2-hydroxyethyl as substituent in the 2-position of trimethylene X is, in particular, that carrying in the 1-position an alkyl having 1–12 C atoms, especially 1–4 C atoms, such as methyl, ethyl or n-propyl, and particularly unsubstituted 2-hydroxyethyl.

Optionally substituted methyl carrying an optionally functionally modified carboxyl group is, as substituent in the 2-position of trimethylene X, in particular methyl itself, which carries an optionally functionally modified carboxyl group, or in the second place such a methyl which is substituted by alkyl having 1–4 C atoms, such as methyl, aralkyl having 7–9 C atoms, such as benzyl, cyclopentyl or cyclohexyl. An optionally functionally modified carboxyl group is, for example, a free esterified or amidated carboxyl or thiocarboxyl group, such as alkoxy-carbonyl having 2–20 C atoms, especially 2–12 C atoms, such as methoxycarbonyl, ethoxycarbonyl or n-propoxycarbonyl, alkenyloxycarbonyl having 3–20 C atoms, particularly 4–11 C atoms, such as allyloxycarbonyl, methallyloxycarbonyl or 10-undecenyloxycarbonyl, cycloalkoxycarbonyl having 5–10 C atoms, aralkoxycarbonyl having 7–12 C atoms, such as benzyloxycarbonyl, p-methylbenzyloxycarbonyl, or α, p-dimethyl-benzyloxycarbonyl, aryloxycarbonyl such as phenoxycarbonyl, alkyl C$_{1-4}$-phenoxycarbonyl or halogenophenoxycarbonyl, such as 4-methylphenoxycarbonyl or 2-chlorophenoxycarbonyl, alkylcarbamoyl having 2–10 C atoms, such as methylcarbamoyl, dialkylcarbamoyl having 3–12 C atoms, such as dimethylcarbamoyl, alkyleneaminocarbonyl having 6 or 7 C atoms, such as pyrrolidinocarbonyl or piperidinocarbonyl, oxoalkyleneaminocarbonyl having 5–6 C atoms, such as morpholinocarbonyl, or azacycloalkoxycarbonyl having 10–22 C atoms, such as 2,2,6,6-tetramethyl-4-piperidinyl-oxycarbonyl, which optionally carries on the N atom alkyl having 1–12 C atoms, such as methyl, alkenyl having 3–12 C atoms, such as allyl, or aralkyl having 7–12 C atoms, such as benzyl.

Optionally substituted methylene carrying an optionally functionally modified carboxyl group is, as substituent in the 2-position of trimethylene X, in particular methylene itself which carries an optionally functionally modified carboxyl group, in second place, such a methylene substituted by alkyl having 1–4 C atoms, such as methyl, aralkyl having 7–12 C atoms, such as benzyl, cyclopentyl or cyclohexyl. An optionally functionally modified carboxyl group is, for example, a free esterified or amidated carboxyl or thiocarboxyl group, such as alkoxycarbonyl having 2–20 C atoms, especially 2–12 C atoms, such as methoxycarbonyl, ethoxycarbonyl or n-propoxycarbonyl, alkenyloxycarbonyl having 3–20 C atoms, especially 4–11 C atoms, such as allyloxycarbonyl, methallyloxycarbonyl or 10-undecenyloxycarbonyl, cycloalkoxycarbonyl having 5–10 C atoms, aralkoxycarbonyl having 7–12 C atoms, such as benzyloxycarbonyl, p-methylbenzyloxycarbonyl, or α-p-dimethylbenzyloxycarbonyl, aryloxycarbonyl such as phenoxycarbonyl, alkyl C$_{1-4}$-phenoxycarbonyl or halogenophenoxycarbonyl, such as 4-methylphenoxycarbonyl or 2-chlorophenoxycarbonyl, alkylcarbamoyl having 2–10 C atoms, such as methylcarbamoyl, dialkylcarbamoyl having 3–12 C atoms, such as dimethylcarbamoyl, alkyleneaminocarbonyl having 6 or 7 C atoms, such as pyrrolidinocarbonyl or piperidinocarbonyl, oxoalkyleneaminocarbonyl having 5–6 C atoms, such as morpholinocarbonyl or azacycloalkoxycarbonyl having 10–22 C atoms, such as 2,2,6,6-tetramethyl-4-piperidyl-oxycarbonyl, which optionally carries on the N atom alkyl having 1–12 C atoms, such as methyl, alkenyl having 3–12 C atoms, such as allyl, or aralkyl having 7–12 C atoms, such as benzyl.

Aryl is substituent in the 2-position of trimethylene X is, in particular, optionally substituted p-hydroxyphenyl or 4-hydroxy-α-naphthyl. Optionally substituted p-hydroxyphenyl is, in particular, unsubstituted p-hyroxyphenyl or, in second place, p-hydroxyphenyl which is substituted in the 2, 3, 5 and/or 6-position and/or on the OH group. Substituents in the 2-, 3-, 5- and 6-position are, for example, alkyl having 1–9, especially 1–4, C atoms, such as methyl or tert-butyl, cycloalkyl having 5–14 C atoms, particularly 6–8 C atoms, such as cyclohexyl, aralkyl having 7–14 C atoms, especially 7–9 C atoms, such as benzyl, aryl, such as phenyl, and alkaryl having 7–14 C atoms, such as tolyl. Hydroxyphenyl or 4-hydroxy-α-naphthyl substituted on the OH group is, in particular, that which carries, instead of the OH group, one of the following groups: alkoxy having 1–20 C atoms, such as methoxy, hydroxyalkoxy having 1–20 C atoms, such as β-hydroxyethoxy, cyanoalkoxy having 2–20 C atoms, such as β-cyanoethoxy, alkenyloxy having 2–20 C atoms, especially 3–4 C atoms, such as allyloxy, alkynyloxy having 2–20 C atoms, particularly 3–4 C atoms, such as propargyloxy, cycloalkoxy having 5–12 C atoms, such as cyclopentyloxy or cyclohexyloxy, aralkoxy having 7–12 C atoms, such as benzyloxy, aryloxy, such as phenoxy, or furyloxy or thienyloxy, alkylcarbamoyloxy having 2–22 C atoms, such as methylcarbamoyloxy and ethylcarbamoyloxy, alkenylcarbamoyloxy having 4–11 C atoms, such as allylcarbamoyloxy, cycloalkylcarbamoyloxy having 5–20 C atoms, such as cyclopentylcarbamoyloxy and cyclohexylcarbamoyloxy, aralkylcarbamoyloxy having 8–15 C atoms, such as benzylcarbamoyloxy, and dialkylcarbamoyloxy having 3–22 C atoms, such as dimethylcarbamoyloxy and diethylcarbamoyloxy.

Optionally 3-substituted 1-oxa-3-aza-tetramethylene carrying in the 2-position oxo or thioxo and in the 4-position oxo or imino is, as substituent in the 2-position of trimethylene X, in particular that wherein the substituent in the 3-position is mono-, di- or trivalent. In the case of a di- or trivalent substituent, the second, or second and third, free valency (valencies) is (are) saturated by a radical (radicals) identical to that bound to the first free valency. Monovalent substituents are, in particular, alkyl having 1–20 C atoms, especially 1–6 C atoms, such as methyl and ethyl, cycloalkyl having 5–7 C atoms, such as cyclopentyl and cyclohexyl, alkenyl having 3–12 C atoms, particularly 3–4 C atoms, such as allyl, aralkyl having 7–12 C atoms, such as benzyl, aryl having 6–16 C atoms, such as alkylphenyl having 7–12 C atoms, e.g. tolyl, halogenophenyl such as chlorophenyl, alkoxyphenyl having 7–12 C atoms such as methoxyphenyl, and phenyl. Divalent substituents are, in particular, arylene such as phenylene and alkylphenylene having 7–12 C atoms, such as methylphenylene, alkylene having 1–10 C atoms, especially 1–4 C atoms, such as methylene and ethylene, alkylenebisphenylene having 13–18 C atoms, such as methylenebisphenylene, thiobisphenylene or dithiobisphenylene, alkenylene having 2–10 C atoms, such as butenylene, aralkylene having 7–12 C atoms, such as benzylidene, oxaalkylene having 2–12 C atoms, such as 3-oxa-pentamethylene, or alkylene-bis-alkyleneoxycarbonyl having 4–20 C atoms, such as butylene-1,4-bis-methyleneoxycarbonyl. Trivalent substituents are, in particular, trivalent radicals of an alkane having 4–12 C atoms, such as 1,3,4-isobutylidine, or alkyl-trisalkyleneoxycarbonyl having 6–20 C atoms, such as isobutyl-1,3,4-tris-methylene-oxocarbonyl, or phenyl-tris-alkylene-oxycarbonyl having 11–20 C atoms, such as phenyl-trismethyleneoxycarbonyl.

Esterified —P(O)(OH)$_2$ as substituent in the 2-position of trimethylene X, whereby simultaneously an OH group is bound in the 2-position, is, in particular, twofold esterified —P(O)(OH)$_2$, wherein the protons of the two OH groups are substituted by, e.g., alkyl having 1–12 C atoms, such as methyl or ethyl, halogenoalkyl having 1–12 C atoms, such as chloromethyl, cycloalkyl having 5–12 C atoms, such as cyclohexyl, alkenyl having 2–12 C atoms, such as allyl or vinyl, aryl, such as phenyl or alkylphenyl having 7–12 C atoms, such as tolyl, or aralkyl having 7–12 C atoms, such as benzyl.

Acylamino as substituent in the 2-position of trimethylene X is, in particular, that wherein acyl is a radical of a carboxylic, sulphonic or phosphoric acid, as is explained further on in the text.

Ketalised oxo as substituent in the 2-position of trimethylene X is, in particular, that which carries two monovalent radicals, such as alkyl having 1–20 C atoms, e.g. methyl, or especially that which carries a divalent radical, as is explained further on in the text.

Optionally substituted propenylene X is substituted in particular in the 2-position, especially by alkoxy having 1–18 C atoms, such as methoxy or ethoxy, cycloalkoxy having 5 or 6 C atoms, such as cyclohexyloxy, arylalkoxy having 7–20 C atoms, such as benzyloxy, alkylphenoxy having 7–12 C atoms, such as tolyoxy, halogenophenoxy, such as chlorophenoxy, hydroxyphenoxy, or 4-hydroxyphenoxy or 4-hydroxynaphthoxy, which are both substituted on the 4—OH group by alkyl having 1–20 C atoms, such as methyl, alkenyl having 2–20 C atoms, such as allyl, alkynyl having 2–20 C atoms, such as propargyl, cycloalkyl having 5–12 C atoms, such as cyclohexyl, aralkyl having 7–12 C atoms, such as benzyl, aryl, such as phenyl, acyl having 1–20 C atoms, such as alkanoyl having 1–20 C atoms, such as acetyl or propionyl, carbamoyl, alkylcarbamoyl having 2–12 C atoms, such as methylcarbamoyl, dialkylcarbamoyl having 3–12 C atoms, such as dimethylcarbamoyl; or in the 2-position of X there is attached 3,3,5,5-tetramethyl-4-aza-cyclohex-1-enyl-thio, -sulphinyl or -sulphonyl or 3,3,4,5,5-pentamethyl-4-aza-cyclohex-1-enyl-thio, -sulphinyl or -sulphonyl.

Optionally substituted 1-aza-dimethylene X is in particular 1-aza-2-oxo-dimethylene, which is optionally substituted on the N atom, especially by a mono-, di-, tri- or quadrivalent radical. In the case of di-, tri- or quadrivalent radicals, the substituents are bound with the other free valencies to radicals identical to those of the first free valency. Monovalent radicals are, in particular, alkyl having 1–20 C atoms, especially 1–6 C atoms, such as methyl or ethyl, alkoxyalkyl having 2–20 C atoms, especially 2–8 C atoms, such as 2-methoxyethyl, alkylthioalkyl having 2–20 C atoms, particularly 2–8 C atoms, such as 2-methylthio-ethyl, alkenyl having 2–12 C atoms, especially 3–4 C atoms, such as allyl, alkynyl having 2–12 C atoms, particularly 3–4 C atoms, such as propargyl, aralkyl having 7–12 C atoms, such as benzyl, hydroxyphenylalkyl having 7–12 C atoms, such as hydroxybenzyl, alkanoyloxyphenylalkyl having 8–20 C atoms, such as acetoxybenzyl. Divalent radicals are, in particular, alkylene having 2–12 C atoms, such as ethylene, propylene or butylene, oxaalkylene having 2–12 C atoms, such as 3-oxapentamethylene, thiaalkylene having 2–12 C atoms, such as 3-thiapentamethylene, alkenylene having 2–10 C atoms, such as 1,4-but-2-enylene, alkynylene having 2–10 C atoms, such as 1,4-but-2-inylene, bis-(alkylene)-arylene having 8–16 C atoms, such as bismethylenephenylene. Trivalent radicals are, in particular, alkyl carrying three oxycarbonylalkyl radicals bound by way of O, and having a total of 7–16 C atoms, such as methyltris-oxycarbonylmethyl. Quadrivalent radicals are, in particular, alkyl which carries four oxycarbonylalkyl radicals bound by way of O and which has a maximum of 9–20 C atoms, such as methyl-tetra-oxycarbonylmethyl.

Optionally substituted 2-aza-trimethylene X is, in particular, 1,3-dioxo-2-aza-trimethylene which is substituted on the N atom, and 2-aza-trimethylene which is substituted on the N atom. In the case of 1,3-dioxo-2-aza-trimethylene, a 2-substituent is especially 3,5-dialkyl-4-hydroxy-phenylalkyl having, in particular, 9–24 C atoms, such as 3,5-di-tert-butyl-4-hydroxyphenyl-methyl or -ethyl, or alkoxycarbonylalkyl having a total of 3–27 C atoms, such as methoxycarbonylmethyl, ethoxycarbonylmethyl, methoxycarbonylethyl or propoxycarbonylpropyl, or a divalent radical which is saturated on the second valency with the same radical as on the first valency, such as alkylene-bis-oxycarbonylalkyl having 5–27 C atoms, such as methylene-bis-oxycarbonylmethyl or 1,2-ethylene-bis-oxycarbonylethyl, or alkyl having 1–20 C atoms, especially 6–18 C atoms, such as n-decyl, or aralkyl having 7–12 C atoms, such as benzyl, or a di- or trivalent radical which is saturated on the remaining free valencies with the same radicals as on the first valency, such as alkylene having 1–20 C atoms, especially 2–12 C atoms, such as ethylene or butylene, arylene-bis-alkylene, such as phenylene-bis-alkylene having a total of 8–16 C atoms, such as phenylene-bis-methylene, alkylphenylene-bis-alkylene having a total of 9–20 C atoms, such as methylphenylene-bis-ethylene, dimethyl-phenylene-bis-propylene, trimethylphenylene-bis-methylene and tetramethylphenylene-bis-methylene, or a trivalent radical of an alkane having 3–9 C atoms, phenenyl-tris-methylene or alkylphenenyl-tris-methylene having a total of 10–20 C atoms, such as methylphenenyl-tris-methylene, dimethyl-phenenyl-tris-methylene or trimethylphenenyl-tris-methylene. In the case of 2-aza-trimethylene, a 2-substituent is in particular alkanoyl having 1–24 C atoms, especially 2–8 C atoms, such as acetyl or propionyl, benzoyl, or a divalent radical which is saturated on the second valency with a radical identical to that on the first valency, such as carbonylalkylenecarbonyl having 3–12 C atoms, such as carbonyl-dimethylenecarbonyl or carbonyloctamethylene carbonyl, or carbonylphenylenecarbonyl.

Optionally substituted 2-aza-tetramethylene X is, in particular, that which in the 1- and/or 4-position optionally carries alkyl having 1–5 C atoms, alkenyl having 3–4 C atoms, alkynyl having 3–4 C atoms or aralkyl having 7–8 C atoms; in the 3-position carries an oxo group; and in the 2-position is optionally substituted, as is described in more detail further on in this text.

A monovalent anion L of an aliphatic carboxylic acid is, in particular, an anion of a carboxylic acid R—COOH, wherein R is an optionally substituted aliphatic hydrocarbon radical. An optionally substituted aliphatic hydrocarbon radical has, in particular, 1–25 C atoms, especially 1–12 C atoms, such as cycloalkyl having 5–12 C atoms, especially 5–6 C atoms, alkenyl having 2–25 C atoms, especially 2–12 C atoms, aralkyl having 7–16 C atoms, particularly 7–12 C atoms, which are optionally substituted by halogen, especially chlorine, hydroxyl, alkyl having 1–6 C atoms or alkoxy having 1–6 C atoms, such as methyl, ethyl, n-hexyl, n-undecyl, 1-ethyl-n-pentyl, cyclohexyl, vinyl, benzyl, chlorobenzyl, hydroxybenzyl, methylbenzyl and methoxybenzyl.

A singly charged anion L of an aliphatic carboxylic acid is also that of an aliphatic α- or β-aminocarboxylic acid, especially of one having 2—20 C atoms, particularly 2–12 C atoms, which is unsubstituted on the amino group, preferably however mono- or dialkylted on the amino group, such as by branched-chain or, in particular, straight-chain alkyl having 1–12 C atoms, especially 1–8 C atoms. Examples of α-aminocarboxylic acids are glycine, α-alanine, valine and isoleucine, which are mono- or disubstituted on the amino group particularly by n-alkyl having 1–8 C atoms, such as di-n-octyl-glycine. An example of β-amino acids is β-alanine which is mono- or disubstituted on the amino group especially by n-alkyl having 1–8 C atoms, such as di-n-propyl-β-alanine.

A singly charged anion L of an aminophosphinic acid or aminophosphonic acid has, in particular, the formula Ia

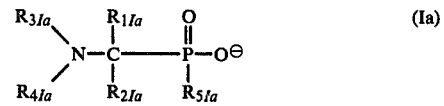

wherein
$R_{1Is}$ and $R_{2Ia}$ independently of one another are hydrogen, alkyl aralkyl, aryl, or aryl or aralkyl substituted by chlorine and/or alkyl groups and/or alkoxy groups, or $R_{1Ia}$ and $R_{2Ia}$ together with the C atom to which they are bound form a cycloalkane ring,
$R_{3Ia}$ and $R_{4Ia}$ independently of one another are hydrogen, alkyl alkoxyalkyl, cycloalkyl, aralkyl, or aralkyl substituted by chlorine and/or alkyl and/or alkoxy groups, and, if neither or only one of the substituents $R_{1Ia}$ and $R_{2Ia}$ is an aromatic radical, $R_{3Ia}$ or $R_{4Ia}$ can also be aryl, or an aryl radical substituted by chlorine and/or alkyl groups and/or alkoxy groups, or $R_{3Ia}$ and $R_{4Ia}$ together with the N atom to which they are bound form a saturated heterocyclic ring, and
$R_{5Ia}$ is alkyl, cycloalkyl, aralkyl, aryl, alkoxy, cycloalkoxy, aralkoxy or aryloxy, whereby the aromatic radical can be substituted by chlorine and/or by alkyl groups and/or alkoxy groups.

If $R_{1Ia}$, $R_{2Ia}$, $R_{3Ia}$, $R_{4Ia}$ or $R_{5Ia}$ are alkyl, the groups can be linear or branched alkyl groups, for example methyl, ethyl, propyl, isopropyl n-butyl, n-hexyl, n-octyl, 2-ethyl-hexyl, n-dodecyl or n-octadecyl. If $R_{3Ia}$ and $R_{4Ia}$ are alkoxyalkyl, they can be, for example, 2-methoxyethyl or 3-methoxypropyl. If these substituents are aralkyl or substituted aralkyl, they can be, for example, benzyl, 4-methylbenzyl, 4-isopropylbenzyl, 3-chlorobenzyl, 4-methoxybenzyl, 2,4-dichlorobenzyl, 2-chloro-4-methylbenzyl, 1- or 2-napthylmethyl, phenylethyl or 2-naphthylethyl. The same substituents as aryl or substituted aryl can be, for example, phenyl, diphenylyl, naphtyl, 4-methylphenyl, 3-chlorophenyl, 3,4-dichlorophenyl, 4-methoxynaphthyl-1, 4-butoxyphenyl, 3-chloro-4-methylphenyl or 3-ethoxyphenyl. If $R_{1Ia}$ and $R_{2Ia}$ together with the C atom to which they are bound form a cycloalkane ring, it can be, for example, a cyclopentane, cyclohexane or 4-methylcyclohexane ring.

If $R_{3Ia}$, $R_{4Ia}$ or $R_{5Ia}$ are cycloalkyl, it can be, for example, cyclopentyl, cyclohexyl or 3-methylcyclohexyl. If $R_{3Ia}$ and $R_{4Ia}$ together with the N atom to which they are bound form a saturated heterocyclic ring, it can be, for example, a pyrrolidine, methylpyrrolidine, dimethylpyrrolidine, piperidine, morpholine, N-methylpiperazine or N-ethylpiperazine ring. If $R_{5Ia}$ is an alkoxy or cycloalkoxy radical, it can be, for example, a methoxy, ethoxy, isopropoxy, butoxy, hexoxy, 2-ethylhexoxy or cyclohexoxy radical. $R_{5Ia}$ as aralkoxy or substituted aralkoxy can be, for example, a benzoxy, 4-chlorobenzoxy, 2,4-dichlorobenzoxy, 3-methylbenzoxy or 2-phenylethoxy radical. $R_{5Ia}$ as aryloxy or as substituted aryloxy can be, for example, a phenoxy, p-tolyloxy, 4-chlorophenoxy, β-naphthoxy, 3-methoxyphenoxy or 3-chloro-4-methylphenoxy group, as is described in DT-OS No. 2,443,400.

Preferred anions are those of formula Ia wherein $R_{1Ia}$ and $R_{2Ia}$ independently of one another are hydrogen, alkyl having 1 to 12 C atoms, aralkyl having 7 to 11 C atoms or aryl having 6 to 12 C atoms, whereby the aromatic ring can be mono- or disubstituted by chlorine and/or methyl and/or alkoxy groups having 1 to 8 C atoms, or $R_{1Ia}$ and $R_{2Ia}$ together with the C atom to which they are bound form a cyclopentane or cyclohexane ring, $R_{3Ia}$ and $R_{4Ia}$ independently of one another are hydrogen, alkyl having 1 to 12 C atoms, cycloalkyl having 5 or 6 C atoms or an aralkyl radical having 7 to 13 C atoms, which can be mono- or disubstituted by chlorine and/or methyl groups and/or alkoxy groups having 1 to 8 C atoms, or, if neither or only one of the substituents $R_{1Ia}$ and $R_{2Ia}$ is an aromatic radical, $R_{3Ia}$ or $R_{4Ia}$ can also be an aryl radical that can be mono- or disubstituted by chlorine and/or alkyl groups having 1 to 4 C atoms and/or alkoxy groups having 1 to 8 C atoms, or $R_{3Ia}$ and $R_{4Ia}$ together with the N atom to which they are bound form a heterocyclic ring of the pyrrolidine, piperidine, piperazine or morpholine class, $R_{5Ia}$ is alkyl having 1 to 8 C atoms, cycloalkyl having 5 or 6 C atoms, aralkyl having 7 to 13 C atoms or aryl having 6 to 12 C atoms, whereby the aromatic ring can be mono- or disubstituted by chlorine and/or methyl groups and/or alkoxy groups having 1 to 8 C atoms, or $R_5$ is an alkoxy radical having 1 to 8 C atoms, the cyclohexoxy radical, the benzoxy radical, the phenoxy radical or a phenoxy radical mono- or disubstituted by chlorine or by methyl groups.

Preferred anions of formula Ia are also those wherein $R_{1Ia}$ and $R_{2Ia}$ independently of one another are hydrogen, alkyl having 1-8 C atoms, benzyl or a phenyl radical substituted by $CH_3$— or $CH_3O$—; or wherein $R_{Ia}$ and $R_{2Ia}$ together with the C atom to which they are bound form a cyclohexane ring, $R_{3Ia}$ and $R_{4Ia}$ independently of one another are hydrogen, alkyl having 1 to 8 C atoms, cyclohexyl, or an aralkyl radical having 7 to 11 C atoms, which can be monosubstituted by methyl, chlorine or alkoxy groups having 1 to 4 C atoms, or, if neither or only one of the substituents $R_{1Ia}$ and $R_{2Ia}$ is an aromatic radical, $R_{3Ia}$ or $R_{4Ia}$ can also be a phenyl radical, which can be mono- or disubstituted by chlorine and/or alkyl having 1 to 4 C atoms and/or alkoxy groups having 1 to 5 C atoms, or $R_{3Ia}$ and $R_{4Ia}$ together with the N atom to which they are bound form a pyrrolidine, piperidine or morpholine ring, $R_{5Ia}$ is alkyl having 1 to 8 C atoms, cyclohexyl, aralkyl having 7 to 11 C atoms, an aryl radical having 6 to 10 C atoms, which can be monosubstituted by Cl, $CH_3$ or $CH_3O$, an alkoxy radical having 1 to 4 C atoms, the benzoxy radical, the phenoxy radical, a chlorophenoxy radical or tolyloxy radical.

Particularly preferred anions of formula Ia are those wherein $R_{1Ia}$ is hydrogen, alkyl having 1 to 6 C atoms, phenyl or 4-methoxyphenyl, $R_{2Ia}$ is hydrogen or methyl, $R_{3Ia}$ is hydrogen alkyl having 2 to 8 C atoms, cyclohexyl, benzyl or 4-methoxybenzyl, $R_{4Ia}$ is hydrogen, alkyl having 2 to 8 C atoms, cyclohexyl, phenyl, 4-methoxyphenyl, 2-methoxy-5-tert.butylphenyl, or $R_{3Ia}$ and $R_{4Ia}$ together with the nitrogen atom to which they are bound form a piperidine or morpholine radical, and $R_{5Ia}$ is alkyl having 1 to 4 C atoms, phenyl, 4-tolyl, 4-methoxyphenyl or an alkoxy radical having 1 to 4 C atoms.

Examples of anions of formula Ia are:

 Ia.1.

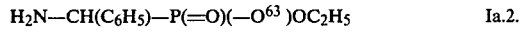 Ia.2.

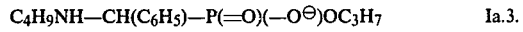 Ia.3.

 Ia.4.

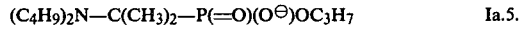 Ia.5.

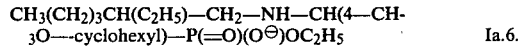 Ia.6.

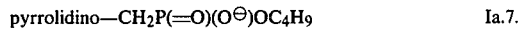 Ia.7.

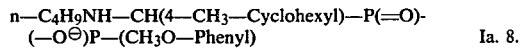 Ia. 8.

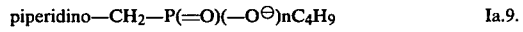 Ia.9.

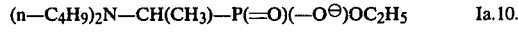 Ia.10.

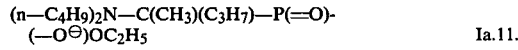 Ia.11.

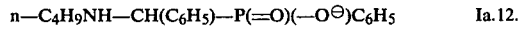 Ia.12.

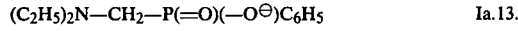 Ia.13.

Optionally substituted imino Z is, in particular, that wherein substituents are: hydroxyl, alkoxy having 1-12 C atoms, especially 1-6 C atoms, alkyl having 1-12 C atoms, especially 1-6 C atoms, cycloalkyl having 5-12 C atoms, particularly 5-6 atoms, aralkyl having 7-12 C atoms or aryl having 6-12 C atoms, especially 6 C atoms; and in particular it is unsubstituted imino. Substituted imino is also alkylimino substituted by —N=C(R$_7$)—C(R$_6$)=C(O$^\ominus$)R$_5$, wherein alkyl has, in particular, 1-6 C atoms, especially 2 C atoms, and the substituent is especially in the 2-position, and wherein $R_5$, $R_6$ and $R_7$ have, in particular, the following meanings:

Alkyl $R_5$, $R_6$ and $R_7$ has, in particular, 1-12 C atoms, especially 1-6 C atoms, such as methyl, ethyl or n-propyl.

Cycloalkyl $R_5$, $R_6$ and $R_7$ is, in particular, that having 5-12 C atoms, especially 5-6 C atoms, such as cyclohexyl.

Aralkyl $R_5$, $R_6$ and $R_7$ is, in particular, that having 7-12 C atoms, such as benzyl or phenethyl.

Aryl $R_5$, $R_6$ and $R_7$ is, in particular, alicyclic or heterocyclic aryl having 4-10 C atoms, such as phenyl, or phenyl substituted by alkyl having 1-12 C atoms, especially 1-6 C atoms, such as methyl, alkoxy having 1-12 C atoms, particularly 1-6 C atoms, or halogen such as chlorine, or, e.g., thienyl.

Alkoxycarbonyl $R_6$ is, in particular, that having 2-12 C atoms, especially 2-6 C atoms, such as methoxycarbonyl or ethoxycarbonyl.

Optionally substituted 1,4-butadi-1,3-enylene $R_5+R_6$ is, in particular, unsubstituted, or is that which carries as substituent: alkyl having 1-12 C atoms, especially 1-6 C atoms, such as methyl, alkoxy having 1-12 C atoms, especially 1-8 C atoms, such as n-octyloxy, or halogen such as chlorine.

Optionally substituted alkyl $R_7$ is, in particular, that having 1–12 C atoms, especially 1–6 C atoms, which carries as substituent halogen such as fluorine or chlorine, such as trifluoromethyl.

Alkoxy $R_7$ is, in particular, that having 1–12 C atoms, especially 1–6 C atoms, such as methoxy or ethoxy.

Optionally substituted amino $R_7$ is, in particular, alkylamino having 1–12 C atoms, such as methylamino, dialkylamino having 2–24 C atoms, such as dimethylamino, and especially anilino, which is unsubstituted, or which carries as substituent in the p-, m- or, in particular, o-position: alkyl having 1–6 C atoms, such as methyl, or especially alkoxy having 1–6 C atoms, such as methoxy.

L is preferably a singly negatively charged anion of an enol of formula I, wherein Z is oxo or imino, $R_5$ is alkyl, $R_6$ is hydrogen, or $R_5$ and $R_6$ together are 1,4-butadi-1,3-enylene and $R_7$ is alkoxy, especially that wherein Z is oxo, $R_5$ is alkyl, $R_6$ is hydrogen and $R_6$ is alkoxy. Equally preferably, $R_7$ is alkyl, particularly methyl or phenyl.

Preferred metal complexes are those of formula III

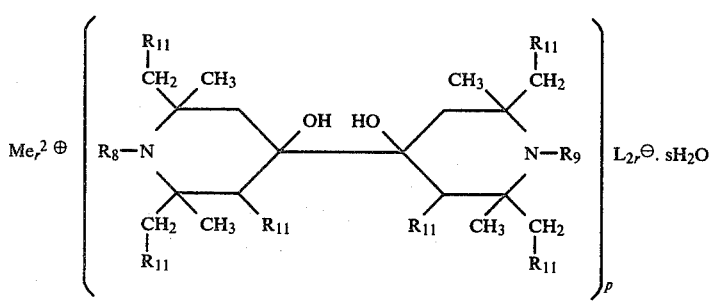

(III), wherein Me, p, r, s and L have the meanings given in the foregoing as being preferred, $R_8$ and $R_9$ independently of one another are hydrogen, alkyl, alkenyl, alkynyl, aralkyl, hydroxyalkyl, alkoxyalkyl, aliphatic or aromatic acyloxyalkyl, cyanoalkyl, halogenoalkyl, epoxyalkyl or alkoxycarbonylalkyl, and $R_{11}$ is hydrogen or methyl.

Alkyl $R_8$ and $R_9$ has, in particular, 1–12 C atoms, especially 1–6 C atoms, such as methyl. Alkenyl $R_8$ and $R_9$ has, in particular, 2–12 C atoms, especially 2–6 C atoms, such as allyl. Alkynyl $R_8$ and $R_9$ has, in particular, 2–12 C atoms, especially 2–6 C atoms, such as propargyl. Aralkyl $R_8$ and $R_9$ has, in particular, 7–12 C atoms, and is optionally substituted, especially by alkyl having 1–12 C atoms, especially 1–6 C atoms, alkoxy having 1–12 C atoms, especially 1–6 C atoms, or halogen such as chlorine, such as benzyl. Hydroxyalkyl $R_8$ and $R_9$ has, in particular, 1–12 C atoms, especially 1–6 C atoms, such as 2-hydroxyethyl. Alkoxyalkyl $R_8$ and $R_9$ has, in particular, 2–12 C atoms, especially 2–6 C atoms, such as 2-methoxyethyl. Aliphatic acyloxyalkyl $R_8$ and $R_9$ has a total of, in particular, 2–18 C atoms, especially 2–12 C atoms. Aromatic acyloxyalkyl $R_8$ and $R_9$ has a total of 7–18 C atoms, especially 7–12 C atoms. Cyanoalkyl $R_8$ and $R_9$ has, in particular, 2–6 C atoms, especially 2–6 C atoms, such as cyanomethyl. Halogenoalkyl $R_8$ and $R_9$ has, in particular, 1–12 C atoms, especially 1–6 C atoms, and halogen is especially chlorine, such as 2-chloroethyl. Epoxyalkyl $R_8$ and $R_9$ has, in particular, 2–12 C atoms, especially 2–6 C atoms, such as 2,3-epoxypropyl. Alkoxycarbonylalkyl $R_8$ and $R_9$ has a total of 3–18 C atoms, especially 3–12 C atoms.

$R_8$ and $R_9$ are preferably identical and are hydrogen or alkyl, especially methyl, such as in 2,2',6,6'-tetraethyl-4,4'-dihydroxy-2,2',3,3',6,6'-hexamethyl-4,4'-bipiperidine and in 2,2,2',2',6,6,6',6'-octamethyl-4,4'-dihydroxy-4,4'-bipiperidine.

Also preferred are metal complexes of formula IV

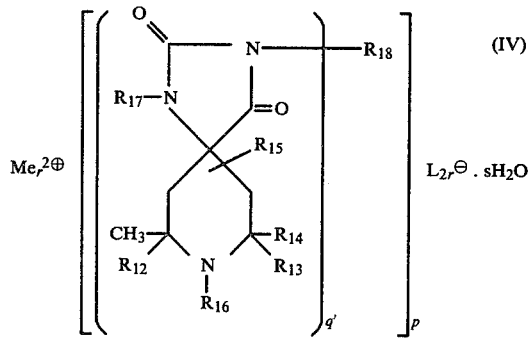

wherein Me, p, r, s and L have the meanings given in the foregoing as being preferred, q' is 1 or 2, $R_{12}$ is alkyl, $R_{13}$ is alkyl, $R_{14}$ is alkyl, phenyl or aralkyl, or $R_{13}$ and $R_{14}$ together are alkylene, $R_{15}$ is hydrogen, alkyl or allyl, $R_{16}$ is hydrogen, oxyl, alkyl, alkenyl aralkly, epoxyalkyl, 2-hydroxyethyl, 2-alkoxyethyl, 2-aryloxyethyl, 2-aralkoxyethyl or 2-acyloxyethyl, $R_{17}$ is hydrogen, alkyl or alkenyl, and $R_{18}$, where n equally 1, is hydrogen, alkyl, alkenyl, aralkyl, aryl, cycloalkyl, epoxyalkyl, alkoxyalkyl, phenoxyalkyl, alkoxycarbonylmethyl, phenoxycarbonylmethyl, hydroxyalkyl, acyloxyalkyl, 2-hydroxyphenethyl, 2-alkoxyphenethyl, 2-aryl-oxyphenethyl, 2-aralkoxyphentethyl or 2-acyloxyphenethyl, or $R_{18}$, where n equals 2, is alkylene, oxaalkylene, alkenylene, arylenedialkylene, arylene, oxydiphenylene, methylenediphenylene, alkylene-di-(oxycarbonylalkylene), alkylene-di-(carbonylalkylene), alkylene-di-(carbonyloxyaralkylene), thiaalkylene-di-(carbonyloxyalkylene), thiaalkylene-di-(carbonyloxyaralkylene), alkenylene-di-(carbonyloxyalkylene), alkenylene-di-(carbonyloxyaralkylene), phenylene-di-(carbonyloxyalkylene), phenylene-di-(carbonyloxyaralkylene), 1,4-cyclohexylene-di-(carbonyloxyalkylene), or 1,4-cyclohexylene-di-(carbonyloxyaralkylene).

Alkyl $R_{12}$, $R_{13}$, $R_{14}$, $R_{15}$, $R_{16}$, $R_{17}$ and $R_{18}$ independently of one another have, in particular, 1–12 C atoms, especially 1–8 C atoms, such as ethyl, n-propyl and particularly methyl. Aralkyl $R_{14}$, $R_{16}$ and $R_{18}$ independently of one another have, in particular, 7–12 C atoms, such as phenethyl and especially benzyl. Alkylene $R_{13}+R_{14}$ has in particular 4–12 C atoms, especially 5 C atoms, such as pentamethylene. Alkenyl $R_{16}$, $R_{17}$ and $R_{18}$ independently of one another have, in particular 2–12 C atoms, especially 2–6 C atoms, such as allyl or methallyl. Epoxyalkyl $R_{16}$ and $R_{18}$ independently of one another have, in particular, 2–12 C atoms, especially 3–6 C atoms, such as 2,3-epoxypropyl. 2-Alkoxyethyl $R_{16}$ has in the alkoxymoiety in particular 1–12 C atoms, especially 1–6 C atoms, such as 2-methoxyethyl. 2-Aryloxyethyl $R_{16}$ has in the aryl moiety in particular 6–12 C atoms, especially 6 C atoms, such as 2-phenoxyethyl. 2-Aralkoxyethyl $R_{16}$ has in the aralkoxy moiety in particular 7–12 C atoms, such as 2-benzyloxyethyl. 2-Acyloxyethyl $R_{16}$ has in the acyloxy moiety in particular 1–20 C atoms, especially 2–8 C atoms, such as alkanoyloxy, e.g. 2-acetoxyethyl. Aryl $R_{18}$ has in particular 6–12 C atoms, such as phenyl, which can also be substituted, particularly by alkyl having 1–12 C atoms, especially 1–6 C atoms, alkoxy having 1–12 C atoms, especially 1–6 C atoms, or halogen such as chlorine. Cycloalkyl $R_{18}$ has in particular 5–12 C atoms, especially 5–6 C atoms, such as cyclohexyl. Alkoxyalkyl $R_{18}$ has in particular 2–18 C atoms, especially 2–12 C atoms, such as methoxymethyl or 2-methoxyethyl. Phenoxyalkyl $R_{18}$ has in particular 7–18 C atoms, especially 7–12 C atoms, such as 2-phenoxyethyl. Alkoxycarbonylmethyl $R_{18}$ has in particular 3–20 C atoms, especially 3–9 C atoms, such as methoxycarbonylmethyl. Hydroxyalkyl $R_{18}$ has in particular 1–12 C atoms, especially 1–6 C atoms, such as 2-hydroxyethyl. Acyloxyalkyl $R_{18}$ has in particular 1–20 C atoms, especially 2–18 C atoms, such as alkanoyloxyalkyl, e.g. 2-acetoxyethyl. 2-Alkoxyphenethyl $R_{18}$ has in the alkoxy moiety in particular 1–12 C atoms, especially 1–6 C atoms. 2-Aryloxyphenethyl $R_{18}$ has in the aryl moiety in particular 6–12 C atoms, especially 6 C atoms. 2-Aralkoxyphenethyl $R_{18}$ has in the aralkoxy moiety in particular 7–12 atoms, especially 7 C atoms. 2-Acyloxyphenethyl $R_{18}$ has in the acyloxy moiety in particular 1–20 C atoms, especially 2–12 C atoms, such as alkanoyloxy. Alkylene $R_{18}$ has in particular 1–20 C atoms, especially 1–8 C atoms, such as methylene, ethylene, 1,3-propylene, 1,4-butylene or 1,8-octylene. Oxaalkylene $R_{18}$ has in particular 2–20 C atoms, especially 2–10 C atoms, such as 3-oxa-pentamethylene. Alkenylene $R_{18}$ has in particular 2–20 C atoms, especially 2–10 C atoms, such as 1,4-but-2-enylene. Arylenedialkylene $R_{18}$ has in particular a total of 8–20 C atoms, especially 8–14 C atoms, such as phenylenedimethylene. Arylene $R_{18}$ has in particular 6–12 C atoms, such as phenylene. Alkylene-di-(oxycarbonylalkylene) $R_{18}$ has in particular a total of 5–20 C atoms, especially 5–12 C atoms, such as alkylene-di-(oxycarbonylmethylene), such as 3,6-dioxa-2,7-dioxo-octamethylene. Alkylene-di-(carbonyloxyalkylene) $R_{18}$ has a total of in particular 5–20 C atoms, especially 7–14 C atoms, such as alkylene-di-(carbonyloxyethylene), such as 3,8-dioxa-4,7-dioxo-decamethylene. Alkylene-di-(carbonyloxyaralkylene) $R_{18}$ has in the alkylene moiety in particular 1–8 C atoms, and the aralkylene moiety is especially phenylethylene, in the case of which the free valency of $R_{18}$ starts from the $\beta$-C atom, such as 2,9-diphenyl-3,8-dioxa-4,7-dioxo-decamethylene. Thiaalkylene-di-(carbonyloxyalkylene) $R_{18}$ has in the thiaalkylene moiety in particular 2–10 C atoms, especially 2–6 C atoms, and in the alkylene moiety 2 C atoms, such as 3,11-dioxa-4,10-dioxo-7-thia-tridecamethylene. Thiaalkylene-di-(carbonyloxyaralkylene) $R_{18}$ has in the thiaalkylene moiety in particular 2–10 C atoms, especially 2–6 C atoms, and the aralkylene moiety is especially phenylethylene, in the case of which the free valency of $R_{18}$ starts from the $\beta$-C atom, such as 2,12-diphenyl-3,11-diphenyl-3,11-dioxa-4,10-dioxo-7-thia-tridecamethylene. Alkenylene-di-(carbonyloxyalkylene) $R_{18}$ has in the alkenylene moiety in particular 2–12 C atoms, especially 4–10 C atoms, and the alkylene moiety is especially ethylene, such as 3,10-dioxa-4,9-dioxo-6,7-dehydro-dodecamethylene. Alkenylene-di-(carbonyloxyaralkylene) $R_{18}$ has in the alkenylene moiety in particular 2–12 C atoms, especially 4–10 C atoms, and the aralkylene moiety is particularly phenylethylene, in the case of which the free valency of $R_{18}$ starts from the $\beta$-C atom, such as 2,11-diphenyl-3,10-dioxa-4,9-dioxo-6,7-dehydrododecamethylene. Phenylene-di-(carbonyloxyalkylene) $R_{18}$ has in the alkylene moiety in particular 2 C atoms, such as phenylene-di-(carbonyloxyethylene). 1,4-Cyclohexylene-di-(carbonyloxyalkylene) $R_{18}$ has in the alkylene moiety in particular 2 C atoms, such as 1,4-cyclohexylene-di-(carbonyloxyethylene). 1,4-Cyclohexylene-di-(carbonyloxyaralkylene) $R_{18}$ has, as aralkylene, in particular phenylethylene, in the case of which the free valency of $R_{18}$ starts from the $\beta$-C atom.

Preferably, $R_{12}$, $R_{13}$ and $R_{14}$ independently of one another are methyl or ethyl, $R_{15}$ is hydrogen or methyl, $R_{16}$ is hydrogen, oxyl or methyl, $R_{17}$ is hydrogen, and $R_{18}$ is, if n is equal to 1, hydrogen, alkyl having 1–8 C atoms, allyl, benzyl, 2,3-epoxypropyl, 2(alkanoyloxy)-ethyl having 2–18 C atoms in the alkanoyloxy moiety, 2-benzoyloxy-ethyl, 2-(alkylbenzoyloxy)-ethyl having 1–4 C atoms in the alkyl moiety, or 2(3,5-di-tert-butyl-4-hydroxyphenethyloxy)-ethyl, or, if n is equal to 2, it is alkylene having 2–6 C atoms, or p-phenylenedimethylene, such as in 7,9-diethyl-6,7,9-trimethyl-1,3,8-triazaspiro[4,5]decane-2,4-dione or in 7,7,9,9-tetramethyl-1,3,8-triazaspiro[4,5]decane-2,4-dione. Particularly preferably, $R_{12}$ and $R_{13}$ are —CH$_2$—$R_{13}'$, and $R_{15}$ is $R_{13}'$, whereby all $R_{13}'$ are identical and are hydrogen or methyl, and whereby $R_{14}$ is methyl.

Also preferred are metal complexes of formula V

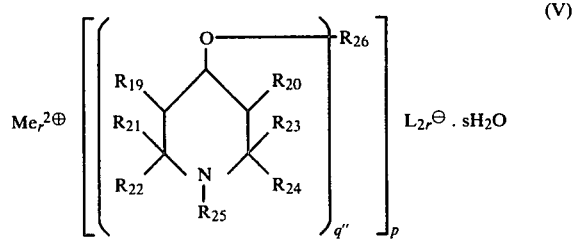

(V)

wherein Me, p, r, s and L have the meanings given in the foregoing as being preferred, $R_{19}$ and $R_{20}$ independently of one another are hydrogen, alkyl, alkenyl, alkynyl or aralkyl, $R_{21}$ and $R_{22}$ independently of one another are alkyl, $R_{23}$ is alkyl, $R_{24}$ is alkyl, phenyl, aralkyl or a 5- or 6-membered heterocyclic radical containing O, S or N, or $R_{23}$ and $R_{24}$ together are alkylene or optionally substituted 3-aza-pentamethylene, $R_{25}$ is hydrogen, oxyl, alkyl, alkenyl, alkoxyalkyl, aralkyl, epoxyalkyl, alkoxycarbonylmethyl, alkenyloxycarbonylmethyl, phenoxycarbonylmethyl, aralkoxycarbonylmethyl, cycloalkyloxycarbonylmethyl, hydroxyalkyl or acyloxyalkyl, q" is 1, 2, 3 or 4, and $R_{26}$ is hydrogen, a mono- to trivalent, optionally substituted hydrocarbon radical or a mono- to quadrivalent radical of an organic or inorganic acid, derived from this by the splitting-off of at least one hydroxyl group.

A monovalent, optionally substituted hydrocarbon radical $R_{26}$ is, in particular, alkyl, alkenyl, aralkyl, cycloalkyl, 2-alkoxycarbonyl-vinyl, 2-alkoxycarbonyl-1-methyl-vinyl or 2-alkoxycarbonyl-1-phenyl-vinyl.

A divalent, optionally substituted hydrocarbon radical $R_{26}$ is, in particular, alkylene, alkenylene or phenylenedimethylene.

A trivalent, optionally substituted hydrocarbon radical $R_{26}$ is, in particular, s-triazine-2,4,6-triyl.

A monovalent radical $R_{26}$ of an organic or inorganic acid is, in particular, that of an aliphatic, araliphatic, alicyclic aromatic or heterocyclic carboxylic acid; or it is a monovalent radical of an S-containing acid, such as of an aliphatic or aromatic sulphonic acid; a monovalent radical of a P-containing acid, such as of an optionally substituted phosphoric acid, phosphonic acid or phosphorous acid; or it is optionally substituted carbamoyl.

A divalent radical $R_{26}$ of an organic or inorganic acid is, in particular, a divalent radical of an aliphatic, aromatic, alicyclic or heterocyclic dicarboxylic acid, carbonyl, sulphinyl or sulphonyl, a radical of a P-containing acid, such as >P-H, >P-alkyl, >P-aryl, >P-aralkyl or —P(OCH$_2$)$_2$C(CH$_2$O)$_2$P—, alkylene-di-aminocarbonyl, arylene-di-aminocarbonyl, phenylene-di-methyleneaminocarbonyl, cyclohexylene-di-aminocarbonyl, oxy-di-(phenyleneaminocarbonyl), methylene-di-(diphenyleneaminocarbonyl), biphenylylene-di-aminocarbonyl, dimethylbiphenylylene-di-aminocarbonyl, methylene-di-(1,4-cyclohexylene-amino-carbonyl), or 1,4-cyclohexylene-di-(methyleneaminocarbonyl).

A trivalent radical $R_{26}$ of an organic or inorganic acid is, in particular, at trivalent radical of a benzenetricarboxylic acid, >P-, >P(=O)— or >B—, and a quadrivalent radical $R_{26}$ is, in particular, such a radical of a benzenetetracarboxylic acid, or >Si<.

Alkyl $R_{19}$, $R_{20}$, $R_{21}$, $R_{22}$, $R_{23}$, $R_{24}$ and $R_{26}$ have in particular 1-12 C atoms, especially 1-6 C atoms, such as ethyl, n-propyl and particularly methyl. Alkenyl $R_{19}$, $R_{20}$, $R_{25}$ and $R_{26}$ have, in particular, 2-12 C atoms, especially 3-4 C atoms, such as allyl or methallyl. Alkynyl $R_{19}$ and $R_{20}$ have in particular 3-4 C atoms, such as propargyl. Aralkyl $R_{19}$, $R_{20}$, $R_{24}$, $R_{25}$ and $R_{26}$ have in particular 7-18 C atoms, especially 7-12 C atoms, and are preferably optionally substituted benzyl or phenethyl, whereby substituents in the phenyl moiety are, in particular: alkyl having 1-12 C atoms, especially 1-6 C atoms, such as methyl, alkoxy having 1-12 C atoms, especially 1-6 C atoms, such as methoxy, or halogen such as chlorine. A 5- or 6-membered heterocyclic radical $R_{24}$ containing O, S or N is, in particular, pyridyl, such as 2-, 3- or 4-pyridyl, 2-furyl, or 2-thienyl. Alkylene $R_{23}+R_{24}$ has, in particular, 4-6 C atoms and is especially pentamethylene. Optionally substituted 3-aza-pentamethylene $R_{23}+R_{24}$ carries as substituent in the 1- and/or 5-position optionally alkyl having 1-6 C atoms, such as methyl, in the 2- and 4-position in each case two alkyl groups, such as methyl and/or ethyl, and in the 3-position a radical corresponding to $R_{25}$, particularly oxyl or alkyl having 1-6 C atoms, such as methyl, or the 3-pentamethylene is unsubstituted in the 3-position, such as 2,2,4,4-tetramethyl-3-aza-pentamethylene, 2,2,3,4,4-pentamethyl-3-azapentamethylene or 1,2,4-trimethyl-2,4-diethyl-3-aza-pentamethylene. Alkoxyalkyl $R_{25}$ has in particular 2-12 C atoms, especially 3-6 C atoms, such as 2-methoxyethyl. Epoxyalkyl $R_{25}$ has in particular 2-12 C atoms, especially 2-6 C atoms, such as 2,3-epoxypropyl. Alkoxy-carbonylmethyl has in the alkoxy moiety in particular 1-12 C atoms, especially 1-6 C atoms, such as methoxycarbonylmethyl. Alkenyloxycarbonylmethyl $R_{25}$ has in the alkenyl moiety in particular 2-12 C atoms, especially 3-6 C atoms, such as allyloxycarbonylmethyl. Aralkoxycarbonylmethyl $R_{25}$ has in the aralkoxy moiety in particular 7-12 C atoms, such as benzyloxycarbonylmethyl. Cycloalkoxycarbonylmethyl has in the cycloalkoxy moiety in particular 5-12 C atoms, especially 6 C atoms, such as cyclohexyloxycarbonylmethyl. Hydroxyalkyl $R_{25}$ has in particular 1-12 C atoms, especially 1-6 C atoms, such as 2-hydroxyethyl. Acyloxyalkyl has in the alkyl moiety in particular 1-12 C atoms, especially 1-6 C atoms, and in the acyl moiety is in particular alkanoyl having 1-18 C atoms, especially 2-12 C atoms, such as 2-acetoxyethyl. Cycloalkyl $R_{26}$ has in particular 5-12 C atoms, especially 5-6 C atoms, such as cyclohexyl. 2-Alkoxycarbonylvinyl $R_{26}$ has in the alkoxy moiety in particular 1-12 C atoms, especially 1-6 C atoms, such as 2-methoxycarbonyl-vinyl. 2-Alkoxycarbonyl-1-methyl-vinyl $R_{26}$ has in the alkoxy moiety in particular 1-12 C atoms, especially 1-6 C atoms, such as 2-methoxycarbonyl-1-methyl-vinyl. 2-Alkoxycarbonyl-1-phenyl-vinyl $R_{26}$ has in the alkoxy moiety in particular 1-12 C atoms, especially 1-6 C atoms, such as 2-methoxycarbonyl-1-phenyl-vinyl. Alkylene $R_{26}$ has in particular 1-18 C atoms, especially 1-12 C atoms, such as particularly straight-chain alkylene having 1-8 C atoms, e.g. 1,2-ethylene, 1,3-propylene or 1,4-butylene. Alkenylene $R_{26}$ has in particular 2-18 C atoms, especially 2-12 C atoms, such as, in particular, straight-chain alkenylene, such as 1,4-but-2-enylene. A monovalent radical $R_{26}$ of an aliphatic carboxylic acid is especially a radical of an alkanecarboxylic acid having, in particular, 1-22 C atoms, especially 1-18 C atoms, such as of acetic acid, propionic acid or butyric acid. A monovalent radical $R_{26}$ of an araliphatic carboxylic acid has in particular 8-20 C atoms, especially 8-12 C atoms, such as the radical of phenylacetic acid or $\beta$-phenylpropionic acid. A monovalent radical $R_{26}$ of an alicyclic carboxylic acid has in particular 6-14 C atoms, especially 6-9 C atoms, such as the radical of cyclohexanecarboxylic acid. A monovalent radical $R_{26}$ of an aromatic carboxylic acid has in particular 7-18 C atoms, especially 7-13 C atoms, such as benzoyl, which is optionally substituted by alkyl having 1-12 C atoms, especially 1-6 C atoms, such as methyl, alkoxy having 1-12 C atoms, especially 1-6 C atoms, such as methoxy, halogen such as chlorine, and/or hydroxyl, such as 4-hydroxy-3,5-dialkyl-benzoyl, e.g. 4-hydroxy-3,5-di-tert-butyl-benzoyl. A monovalent radical $R_{26}$ of a heterocyclic carboxylic acid is in particular that of a pyridinecarboxylic acid, of a furancarboxylic acid or of a thiophenecarboxylic acid. A radical $R_{26}$ of an aliphatic sulphonic acid has in particular 1-20 C atoms, especially 1-6 C atoms, such as that of an alkanesulphonic acid such as methanesulphonic acid. A radical $R_{26}$ of an aromatic sulphonic acid has in particular 6-20 C atoms, especially 6-12 C atoms, such as that of an optionally substituted benzensulphonic acid or naphthalenesulphonic acid, wherein substituents are, for example: alkyl having 1-12 C atoms, especially 1-6 C atoms, such as methyl, alkoxy having 1-12 C atoms, especially 1-6 C atoms, such as methoxy, or halogen such as chlorine or bromine, such as p-toluenesulphonic acid. A monovalent radical $R_{26}$ of a P-containing acid is in particular (ethylenedioxy)P—, —P(OCH$_2$)$_2$C(CH$_3$)$_2$ or —P(=O) (OC$_2$H$_5$)CH$_2$C$_6$H$_5$. Optionally substituted carbamoyl $R_{26}$ has in particular 1-20 C atoms and is, for example, carbamoyl, N-mono- or N-disubstituted carbamoyl, wherein substituents are in particular: alkyl having in particular 1–18 C atoms, especially 1–4 C atoms, such as methyl or ethyl, aralkyl having in particular 7–8 C atoms, such as benzyl or phenethyl, aryl having in particular 6–12 C atoms, such as phenyl, which can also be substituted by, for example, halogen such as chlorine, or alkyl having in particular 1–4 C atoms, such as methyl, cycloalkyl having 5–8 C atoms, such as cyclohexyl, or both substituents together with the N atoms binding them are piperidino, pyrrolidino or morpholino, N-monosubstituted carbamoyl is preferred. A divalent radical $R_{26}$ of an aliphatic or alicyclic carboxylic acid has in particular 2–20 C atoms, especially 2–10 C atoms, such as alkylenedicarbonyl, e.g. oxalyl, malonyl, ethylenedicarbonyl, tetramethylenedicarbonyl, hexamethylenedicarbonyl, octamethylenedicarbonyl or decamethylenedicarbonyl, or thiaalkylenedicarbonyl having in particular 4–12 C atoms, such as 3-thiapentamethylenedicarbonyl, or alkenylenedicarbonyl having in particular 4–12 C atoms, especially 4–6 C atoms, such as vinylenedicarbonyl or 1,4-but-2-enylene-dicarbonyl, or cyclohexenylene dicarbonyl, such as p-cyclohexylenedicarbonyl. A divalent radical $R_{26}$ of an aliphatic carboxylic acid can however also be a divalent radical of a $C_{36}$-dicarboxylic acid, a trivalent radical can be a trivalent radical of a $C_{37}$-$C_{54}$-tricarboxylic acid. A divalent radical $R_{26}$ of an aromatic or heterocyclic carboxylic acid has in particular 6–12 C atoms, such as phenylenedicarbonyl, e.g. o-, m- or p-phenylenedicarbonyl, or pyridine-2,4- or 2,5-dicarbonyl, or thiophene-2,5-dicarbonyl. A radical $R_{26}$ as P-alkyl has in particular 1–4 C atoms, such as methyl or ethyl. A radical $R_{26}$ as $>$P-aryl is especially $>$P-phenyl. A radical $R_{26}$ as $>$P-aralkyl contains in the aralkyl moiety in particular 7–12 C atoms, and therein optionally substituents such as alkyl having in particular 1–12 C atoms, especially 1–8 C atoms, and/or hydroxy, such as benzyl or 3,5-di-tert-butyl-4-hydroxybenzyl. Alkylene-di-aminocarbonyl $R_{26}$ is unsubstituted on the amino, or substituted by alkyl having in particular 1–6 C atoms, such as methyl, and contains in the alkylene moiety especially 2–10 C atoms, such as ethylene or tetramethylene. Arylene-di-aminocarbonyl $R_{26}$ is unsubstituted on the amino, or substituted by alkyl having in particular 1–6 C atoms, such as methyl, and contains in the arylene moiety in particular 6–10 C atoms, especially 6 C atoms, and optionally alkyl substituents such as methyl, such as o-, m- or p-phenylene-di-aminocarbonyl.

In compounds of formula V, malonyl $R_{26}$ is preferably mono- or disubstituted malonyl, whereby q″ is 2, and the remaining symbols in formula V have the aforestated general and preferred meanings. Substituents in the 2-position of the malonyl are one or two 3,5-dialkyl-4-hydroxy-benzyl radicals, wherein alkyl is that having 1–8 C atoms. Alkyl has in particular the meaning of a primary, secondary or especially tertiary alkyl group, such as methyl, tert.-octyl or in particular tert.-butyl. Examples of such malonyl are, in particular, 3,5-di-tert.-butyl-4-hydroxybenzylmalonyl and bis-(3,5-di-tert.-butyl-4-hydroxybenzyl)-malonyl.

In compounds of formula V with q″ equal to 2 and with otherwise the aforementioned general and preferred meanings, a substituted malonyl $R_{26}$ is preferably also that of the formula Va

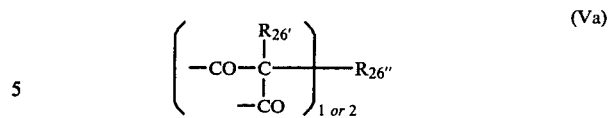

wherein $R_{26'}$ is a 3,5-dialkyl-4-hydroxybenzyl or 2,6-dialkyl-3-hydroxybenzyl, and $R_{26''}$ as a monovalent radical is alkyl having 1–18 C atoms, cyanoalkyl having 2–5 C atoms, $C_1$–$C_4$-alkoxycarbonyl-$C_1$–$C_4$-alkyl, optionally N-$C_1$–$C_{12}$-alkylated or benzylated 2,2,6,6-tetra-$C_1$–$C_6$-alkylpiperidinyl-4-oxycarbonyl-$C_1$–$C_4$-alkyl, $C_2$–$C_{18}$-alkanoyloxy-$C_1$–$C_4$-alkyl, cyclohexylcarbonyloxy-$C_1$–$C_4$-alkyl, benzoyloxy-$C_1$–$C_4$-alkyl or benzylcarbonyloxy-$C_1$–$C_4$-alkyl, di-($C_1$–$C_4$-alkyl)-phosphono $C_1$–$C_4$-alkyl, di-allylphosphono-$C_1$–$C_4$-alkyl, $C_3$–$C_6$-alkenyl, $C_3$–$C_6$-alkynyl, phenyl or $C_7$–$C_{15}$-aralkyl; and $R_{26''}$ as divalent radical is a direct bond, alkylene having 1–12 C atoms, which can be interrupted by one or two of the groups —O—, —S— or —CO—O—, $C_8$–$C_{14}$-arylenebisalkylene or $C_4$–$C_8$-alkenylene. Particularly preferably, $R_{26'}$ is 3,5-di-tert.-butyl-4-hydroxybenzyl or 2,6-di-tert.-butyl-3-hydroxybenzyl, and $R_{26''}$ as monovalent radical is alkyl having 1–8 C atoms, $C_3$–$C_4$-alkenyl, propargly, benzyl, phenyl or optionally N-methylated or N-benzylated 2,2,6,6-tetramethyl-piperidinyl4-oxy-carbonylmethyl, and $R_{26''}$ as divalent radical is $C_2$–$C_6$-alkylene or $C_8$–$C_{14}$-arylenebisalkylene. Alkyl in hydroxybenzyl $R_{26'}$ has in particular 1–8 C atoms, such as methyl, tert.-octyl and especially tert.-butyl. Alkyl $R_{26''}$ is in particular alkyl having 1–8 C atoms, such as methyl. Cyanoalkyl $R_{26''}$ is, for example, cyanomethyl. Alkoxycarbonylalkyl $R_{26''}$ is in particular $C_1$–$C_4$-alkoxycarbonylmethyl, such as methoxycarbonylmethyl. 2- and 6-Substituents in piperidinyl radicals are in particular methyl. Alkanoyloxy-alkyl $R_{26''}$ is in particular $C_2$–$C_{18}$-alkanoyloy-methyl, such as acetoxymethyl. Cyclohexylcarbonyloxyalkyl $R_{26''}$ is, for example, cyclohexylcarbonyloxymethyl. Benzoyloxyalkyl $R_{26''}$ is, for example, benzoyloxymethyl. Benzylcarbonyloxyalkyl $R_{26''}$ is, for example, benzylcarbonyloxymethyl. Dialkylphosphonoalkyl $R_{26''}$ is, for example, dimethylphosphonomethyl. Diallylphosphonoalkyl $R_{26''}$ is, for example, diallylphosphonomethyl. Alkenyl $R_{26''}$ is, for example, methallyl. Alkynyl is, for example, propargyl. Aralkyl $R_{26''}$ is, for example, benzyl. Alkylene $R_{26''}$ is, for example, ethylene. Arylenebisalkylene is, for example, phenylenebismethylene.

Preferably in formula V, $R_{19}$ is hydrogen, $R_{20}$ is hydrogen or methyl, $R_{21}$ and $R_{23}$ are methyl, $R_{22}$ and $R_{24}$ are methyl or ethyl, $R_{25}$ is hydrogen, methyl, allyl, benzyl, 2,3-epoxypropyl, 2-hydroxyethyl, 2-alkanoyloxy-ethyl having 2–18 C atoms in the alkanoyl moiety, or 2-benzoylkoxy-ethyl, more especially hydrogen or methyl, q″ is 1 or 2, and in the case where q″ is 1, $R_{26}$ is alkanoyl having 2–18 C atoms, benzoyl, benzoyl having 1–3 substituents which can be identical or different and denote alkyl having 1–4 C atoms or hydroxyl, β-(3,5-di-tert-butyl-4-hydroxyphenyl)-propionyl, alkycarbamoyl having 1–18 C atoms in the alkyl moiety, phenylcarbamoyl or cyclohexylcarbamoyl; and in the case where q″ is 2, $R_{26}$ is alkylenedicarbonyl having 2–12 C atoms in the alkylene moiety, 3-aza-pentamethylenedicarbonyl, phenylenedicarbonyl, sulphinyl, hexamethylene-di-aminocarbonyl, 2,4-tolylene-di-aminocarbonyl or methylene-di-(p-phenylene-aminocarbonyl). If $R_{20}$ is methyl, $R_{22}$ and $R_{24}$ are preferably ethyl. If $R_{20}$ is hydrogen, $R_{22}$ and $R_{24}$ are preferably methyl.

In the case where q″ equals 1, $R_{26}$ is particularly preferably alkanoyl having 2-18 C atoms, benzoyl, benzoyl having 1-3 substituents which are identical or different and are alkyl having 1-4 C atoms or hydroxyl, or β(3,5-di-tert.butyl-4-hydroxyphenyl)-propionyl; and in the case where q″ equals 2, $R_{26}$ is alkylenedicarbonyl having 1-12 C atoms in the alkylene moiety, 3-aza-pentamethylenedicarbonyl or phenylenedicarbonyl, as is illustrated by 4-benzoyloxy-2,6-di-ethyl-2,3,6-trimethyl-piperidine, 4-benzoyloxy-2,2,6,6-tetramethylpiperidine, 4-stearoyloxy-2,2,6,6-tetramethylpiperidine or bis-(2,2,6,6-tetramethyl-4-piperidyl)-sebacate.

Also preferred are metal complexes of formula VI

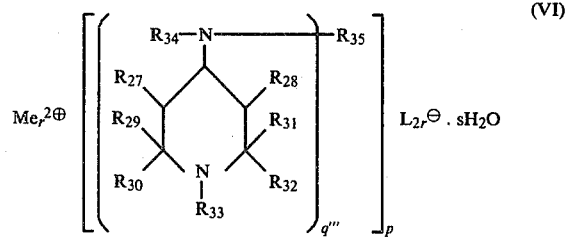

(VI)

wherein Me, p, r, s and L have the meanings given i the foregoing as being preferred, and wherein the symbols otherwise have the following meanings; $R_{27}$ and $R_{28}$ are, independently of one another, hydrogen, alkyl, alkenyl, alkynyl or aralkyl, $R_{29}$ and $R_{30}$ independently of one another are alkyl, $R_{31}$ is alkyl, phenyl, benzyl or phenethyl, $R_{32}$ is alkyl, or $R_{31}$ and $R_{32}$ together are tetramethylene or pentamethylene, $R_{33}$ is hydrogen, oxyl, alkyl, alkenyl, alkoxyalkyl, ralkyl, 2,3-epoxypropyl, alkoxycarbonylmethyl, alkenyloxycarbonylmethyl, phenoxycarbonylmethyl, aralkoxycarbonylmethyl, cyclohexyloxycarbonylmethyl, 2-hydroxyethyl, 2-hydroxypropyl, 2-phenyl-2-hydroxyethyl, 2-acyloxyethyl, 2-acyloxypropyl or 2-phenyl-2-acyloxy-ethyl, $R_{34}$ is hydrogen, alkyl, cycloalkyl or aralkyl, q‴ is 1, 2 or 3, and $R_{35}$ where q‴ is equal to 1 is alkanoyl, alkenoyl, alkoxycarbonyl, benzyloxycarbonyl, cycloalkoxycarbonyl, arylcarbonyl, styrylcarbonyl, aralkylcarbonyl, heterocyclylcarbonyl, optionally substituted carbamoyl, alkylsulphonyl, arylsulphonyl, —P(alkoxy)$_2$, —P(aryloxy)$_2$, —P(alkyl)$_2$, —P(aryl)$_2$, —P(aralkyl)$_2$, —P(cyclohexyl)$_2$, —P(O or S)(alkoxy)$_2$, —P(O or S)(aryloxy)$_2$, —P(O or S)(alkyl)$_2$, —P(O or S)(aryl)$_2$, —P(O or S)(aralkyl)$_2$, —P(O or S))cyclohexyl)$_2$, or $R_{35}$ and $R_{34}$ together with the N atom binding them are succinimido, malonimido or phthalimido; and $R_{35}$ where q‴ is equal to 2 is carbonyl, oxalyl, alkylenedicarbonyl, thiaalkylenedicarbonyl, alkenylenedicarbonyl, arylenedicarbonyl, cyclohexylenedicarbonyl, alkylene-di-aminocarbonyl, arylene-di-aminocarbonyl, cyclohexylene-di-aminocarbonyl, >P(alkoxy), >P(aryloxy), >P(alkyl), >P(aryl), >P(aralkyl), >P(cyclohexyl), >P(O or S)(alkyl), >P(O or S)(aralkyl) or >P(O or S) (cyclohexyl); and $R_{35}$ where q⁗ is equal to 3 is benzenetricarbonyl, 2,4,6-triyl, ≧P, ≧PO or ≧PS.

Alkyl $R_{27}$ and $R_{28}$ have in particular 1-5 C atoms, such as methyl. Alkenyl $R_{27}$ and $R_{28}$ have in particular 3-4 C atoms, such as allyl. Alkynyl $R_{27}$ and $R_{28}$ have in particular 3-4 C atoms, such as propargyl. Aralkyl $R_{27}$ and $R_{28}$ have in particular 7-8 C atoms, such as benzyl. Alkyl $R_{29}$ and $R_{30}$ have in particular 1-6 C atoms, such as methyl or ethyl. Alkyl $R_{31}$ has in particular 1-9 C atoms, such as methyl or ethyl. Alkyl $R_{32}$ has in particular 1-6 C atoms, such as methyl or ethyl. Alkyl $R_{33}$ has in particular 1-8 C atoms, such as methyl. Alkenyl $R_{33}$ has in particular 3-6 C atoms, such as allyl. Alkoxyalkyl $R_{33}$ has in particular 2-21 C atoms, especially 2-12 C atoms, such as 2-methoxyethyl. Aralkyl $R_{33}$ has in particular 7-8 C atoms, such as benzyl or phenethyl, and is optionally substituted in the aryl moiety by chlorine, hydroxyl, alkyl having 1-4 C atoms or alkoxy having 1-4 C atoms, such as 3,5-di-tert-butyl-4-hydroxybenzyl. Alkoxycarbonylmethyl $R_{33}$ has in the alkyl moiety in particular 1-8 C atoms, such as methoxycarbonylmethyl. Alkenyloxycarbonylmethyl $R_{33}$ has in the alkenyl moiety in particular 3-6 C atoms, such as allyloxycarbonylmethyl. Aralkoxycarbonylmethyl $R_{33}$ has in the aralkyl moiety in particular 7-8 C atoms, such as benzyloxycarbonylmethyl. 2-Acyloxyethyl, 2-acyloxypropyl and 2-phenyl-2-acyloxy-ethyl $R_{33}$ have in the acyloxy moiety in particular up to 18 C atoms, such as alkanoyloxy, alkenoyloxy, aroyloxy, such as benzoyloxy which is optionally substituted by chlorine, alkyl having 1-4 C atoms, alkoxy having 1-8 C atoms and/or hydroxyl, such as 3,5-di-tert-butyl-4-hydroxybenzoyl, aralkylcarbonyl such as benzylcarbonyl or phenethylcarbonyl, which are optionally substituted in the aryl moiety by alkyl having 1-4 C atoms, alkoxy having 1-8 C atoms, chlorine and/or hydroxyl, such as β-(3,5-di-tert-butyl-4-hydroxyphenyl)-propionyl, or cycloalkylcarbonyl such as cyclohexylcarbonyl. Alkyl $R_{34}$ has in particular 1-12 C atoms, such as methyl. Cycloalkyl $R_{34}$ has in particular 5-7 C atoms, such as cyclohexyl. Aralkyl $R_{34}$ has in particular 7-8 C atoms, such as benzyl. Alkanoyl $R_{35}$ has in particular 2-18 C atoms, such as acetyl, propionyl, lauroyl or stearoyl. Alkenoyl $R_{35}$ has in particular 3-6 C atoms. Alkoxycarbonyl $R_{35}$ has in the alkoxymoiety in particular 1-8 C atoms, such as methoxycarbonyl. Cycloalkoxycarbonyl $R_{35}$ has in the cycloalkoxy moiety in particular 5-7 C atoms, such as cyclohexyloxycarbonyl. Arylcarbonyl $R_{35}$ is in particular benzoyl which is optionally substituted by chlorine, alkyl having 1-4 C atoms, alkoxy having 1-4 C atoms and/or hydroxyl, such as 3,5-di-tert-butyl-4-hydroxy-benzoyl. Aralkylcarbonyl $R_{35}$ has in the aralkyl moiety in particular 7-12 C atoms, such as benzylcarbonyl or phenethylcarbonyl, and in the aryl moiety is optionally substituted by chlorine, alkyl having 1-4 C atoms, alkoxy having 1-4 C atoms and/or hydroxyl, such as β-(3,5-di-tert-butylphenyl)-propionyl. Heterocyclylcarbonyl $R_{35}$ is, for example, 2-, 3- or 4-pyridylcarbonyl, 2-furylcarbonyl or 2-thienylcarbonyl. Optionally substituted carbamoyl $R_{35}$ is, for example, carbamoyl, mono- or disubstituted carbamoyl, such as alkylcarbamoyl having 1-18 C atoms in the alkyl moiety, arylcarbamoyl having 6-10 C atoms in the aryl moiety, such as phenylcarbamoyl which in the phenyl moiety can also be substituted by chlorine or alkyl having 1-4 C atoms, aralkylcarbamoyl having 7-8 C atoms in the aralkyl moiety, such as benzylcarbamoyl, or cyclohexylcarbamoyl, whereby these carbamoyl radicals can carry as second N substituent alkyl having 1-4 C atoms, especially methyl. Alkylsulphonyl $R_{35}$ is in particular methyl or ethylsulphonyl. Arylsulphonyl $R_{35}$ is in particular phenyl- or tolylsulphonyl. Alkoxy has in the P radicals mentiioned for $R_{35}$ in particular 1-12 C atoms, such as methoxy; aryloxy has therein in particular 6-12 C atoms, such as phenoxy; alkyl has therein in particular 1–12 C atoms, such as methyl; aryl has therein in particular 6–14 C atoms, such as phenyl; and aralkyl has therein in particular 7–8 C atoms, such as benzyl. Alkylenedicarbonyl $R_{35}$ has in the alkylene moiety in particular 1–10 C atoms, such as methylene, ethylene or octamethylene, Thiaalkylenedicarbonyl $R_{35}$ has a total of in particular 4–6 C atoms, such as 3-thia-pentamethylene-di-carbonyl. Alkenylenedicarbonyl $R_{35}$ has a total of in particular 4–6 C atoms. Arylenedicarbonyl is especially phenylenedicarbonyl or alkyl-phenylene-dicarbonyl having 1–4 C atoms in the alkyl moiety. Alkylene-di-aminocarbonyl $R_{35}$ has in the alkylene moiety in particular 2–10 C atoms, such as ethylene- or 1,4-butylene-di-aminocarbonyl. Arylene-di-aminocrbonyl $R_{35}$ has in the arylene moiety in particular 6–13 C atoms, such as phenylene-di-aminocarbonyl.

Preferably, $R_{27}$ is hydrogen, $R_{28}$, $R_{29}$ and $R_{31}$ are methyl, and $R_{30}$ and $R_{32}$ are ethyl; in particular, however, $R_{27}$ and $R_{28}$ are hydrogen, and $R_{29}$, $R_{30}$, $R_{31}$ and $R_{32}$ are methyl.

Methylenedicarbonyl (malonyl) $R_{35}$ in compounds of formula VI is preferably monosubstituted malonyl, whereby q''' is 2, and the remaining symbols in formula VI have the aforestated general and preferred meanings. A substituent in the 2-position of the malonyl is a 3,5-dialkyl-4-hydroxy-benzyl group, wherein alkyl is that having 1–8 C atoms. Alkyl is in particular a primary, secondary or tertiary alkyl, such as methyl, tert.-octyl or especially tert.-butyl. An example of such a malonyl is 3,5-di-tert. butyl-4-hydroxy-benzyl-malonyl.

Particularly suitable also are metal complexes of formula VIa, corresponding to formula VI, wherein the piperidine in the brackets P corresponds to the following formula VIb, and Me, r, L and s have the aforesaid meanings:

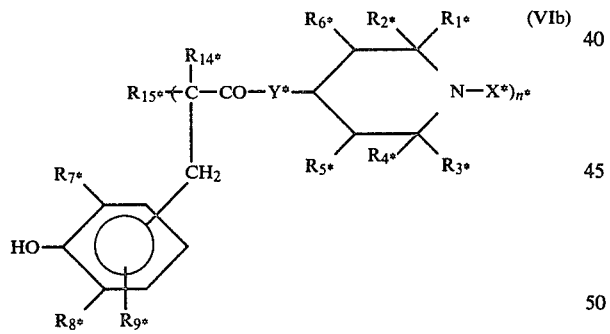
(VIb)

wherein
n|is 1 or 2,
Y| is oxy or imino,
$R_1|,R_2|R_3|$ independently of one another are $C_1$–$C_6$-alkyl, and $R_4|$ is $C_1$–$C_9$-alkyl, phenyl, benzyl or α-phenylethyl, or $R_3|$ and $R_4|$ together are tetramethylene or pentamethylene, $R_5|$ and $R_6|$ independently of one another are hydrogen or $C_1$–$C_5$-alkyl, $R_7|$ and $R_8|$ independently of one another are $C_1$–$C_9$-alkyl, $C_7$–$C_9$-aralkyl or $C_5$–$C_8$-cycloalkyl, $R_9*$ is hydrogen or methyl.

$X^*$ is hydrogen, oxyl, $C_1$–$C_{12}$-alkyl, $C_3$–$C_6$-alkenyl, $C_3$–$C_4$-alkynyl, $C_2$–$C_{21}$-alkoxyalkyl, $C_7$–$C_8$-aralkyl, 2,3-epoxypropyl, or one of the groups —CH$_2$COOR$_{10*}$ or —CH$_2$—CH(R$_{11*}$)—OR$_{12*}$, wherein $R_{10*}$ is $C_1$–$C_8$-alkyl, $C_3$–$C_6$-alkenyl, phenyl, $C_7$–$C_8$-aralkyl or cyclohexyl, and $R_{11*}$ is hydrogen, methyl or phenyl, and $R_{12*}$ is hydrogen, an aliphatic, aromatic, araliphatic or alicyclic acyl group having 1–18 C atoms, wherein the aromatic moiety can optionally be substituted with chlorine, $C_1$–$C_4$-alkyl, $C_1$–$C_8$-alkoxy and/or with hydroxyl, and $R_{14*}$ is cyano, —CHO, —CO—R$_{16*}$, —SO$_2$—R$_{17*}$, —SO—R$_{17*}$, —P(=O(OR$_{18*}$)$_2$ or nitro, wherein R$_{16*}$ and R$_{17*}$ are $C_1$–$C_{17}$-alkyl, phenyl, $C_7$–$C_9$-alkylphenyl, $C_{11}$–$C_{14}$-(hydroxy)(alkyl)phenyl or $C_{12}$–$C_{16}$-(hydroxy)(alkyl)phenylalkyl, or R$_{16*}$ is a radical bound with R$_{15*}$, and R$_{18*}$ is $C_1$–$C_{18}$-alkyl, phenyl or allyl, and $R_{15*}$ is $n^*$ is 1 is hydrogen, a radical of the formula VIc

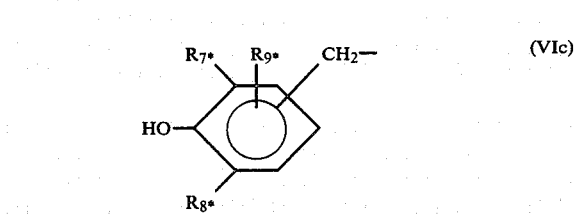
(VIc)

wherein $R_{7*}$, $R_{8*}$ and $R_{9*}$ have the aforesaid meaning, or $C_1$–$C_{20}$-alkyl, or a $C_1$–$C_{10}$-alkyl substituted by phenoxy, $C_7$–$C_{10}$-alkylphenoxy, benzyloxy, cyclohexyloxy, phenylthio, $C_7$–$C_{10}$-alkylphenylthio, $C_2$–$C_{13}$-alkanoyl, cyano, —C(=O)OR$_{19*}$, —O—C(=O)R$_{20*}$ or —P(=O) (OR$_{21*}$)$_2$, whereby R$_{19*}$ is $C_1$–$C_{18}$-alkyl, $C_5$–$C_{12}$-cycloalkyl or a radical of formula VId

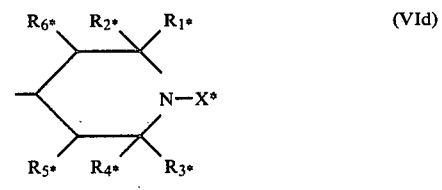
(VId)

wherein $R_{1*}$, $R_{2*}$, $R_{3*}$, $R_{4*}$, $R_{5*}$, $R_{6*}$ and $X^*$ have the aforesaid meaning, $R_{20*}$ is $C_1$–$C_{17}$-alkyl, $C_5$–$C_{12}$-cycloalkyl, phenyl or $C_7$–$C_9$-phenylalkyl, whereby in the last two radicals, phenyl moieties can be substituted by one or two $C_1$–$C_4$-alkyl and/or hydroxyl groups, and $R_{21*}$ is $C_1$–$C_8$-alkyl, allyl or phenyl, and $R_{15*}$ is furthermore $C_2$–$C_{22}$-alkyl interrupted by —O—, —S—, —SO— or —SO$_2$—, or is $C_3$–$C_{18}$-alkenyl, $C_3$–$C_8$-alkynyl, $C_5$–$C_{12}$-cycloalkyl, $C_6$–$C_{18}$-alkylcycloalkyl, $C_6$–$C_{14}$-cycloalkylalkyl, $C_7$–$C_{19}$-aralkyl, $C_7$–$C_{19}$-alkylaralkyl, phenyl or a radical of the above formula VId, or together with R$_{16*}$ is trimethylene or tetramethylene which is optionally substituted by an oxo group and/or vicinally by R$_{14*}$ and a radical of formula VIe

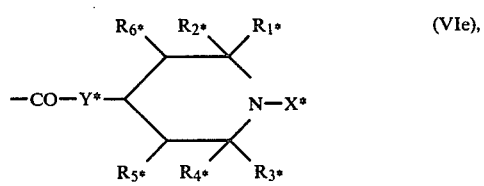
(VIe), wherein X*, Y*, $R_{1*}$, $R_{2*}$, $R_{3*}$, $R_{4*}$, $R_{5*}$, $R_{6*}$ and $R_{14*}$ have the aforesaid meaning, or $R_{15*}$ if n* is 2 is a direct bond, $C_1-C_{20}$-alkylene, $C_2-C_{20}$-alkylene singly or doubly interrupted by —O—, —S—, —SO—, —SO$_2$— or —CO—O—, $C_8-C_{14}$-arene-bis-alkylene, $C_4-C_8$-alkenylene or $C_4-C_8$-alkynylene.

$R_{1*}$, $R_{2*}$ and $R_{3*}$ as alkyl are, e.g., straight-chain or branched-chain alkyl having 1–6 C atoms, such as methyl, ethyl, n-propyl, isopropyl, n-butyl, isobutyl, isopentyl or n-hexyl. Compounds to the mentioned amongst the preferred compounds are those wherein $R_{1*}$ and $R_{3*}$ are methyl or ethyl, and $R_{2*}$ is methyl.

$R_{4*}$ as alkyl is, e.g., straight-chain or branched-chain alkyl having 1–9 C atoms, especially having 1–6 C atoms, and in particular having 1 C atom, such as methyl, ethyl, isopropyl, n-butyl, isopentyl, n-hexyl, 2-ethylhexyl or isononyl, especially methyl.

$R_{5*}$ and $R_{6*}$ as $C_1-C_5$-alkyl are, e.g., straight-chain or branched-chain alkyl, such as methyl, ethyl, isopropyl, isobutyl, n-pentyl. $R_{5*}$ preferably has one C atom less than $R_{1*}$, and $R_{6*}$ one C atom less than $R_{2*}$. The preferred meaning of $R_{5*}$ is hence hydrogen or methyl, and of $R_{6*}$ it is hydrogen.

The benzyl radical carrying $R_{7*}$, $R_{8*}$ and $R_{9*}$ can be a para- or meta-hydroxybenzyl group. The substituents $R_{7*}$ and $R_{8*}$ on the benzyl radical can be straight-chain or branched-chain alkyl groups having 1–9 C atoms, e.g. methyl, ethyl, isopropyl, tert.-butyl, n-hexyl, 1,1,3,3-tetramethylbutyl or tert.-nonyl. If $R_{7*}$ or $R_{8*}$ are cycloalkyl, this can be, for example, cyclopentyl, methylcyclopentyl, cyclohexyl or methylcyclohexyl. If $R_{7*}$ or $R_{8*}$ are aralkyl, this can be, e.g., benzyl or α,α-dimethylbenzyl. $R_{7*}$ and $R_{8*}$ are preferably alkyl groups having 1–4 C atoms, especially methyl or tert.-butyl.

X* as $C_1-C_{12}$-alkyl is, e.g., methyl, ethyl, n-propyl, n-butyl, n-pentyl, n-hexyl, n-octyl, n-decyl or n-dodecyl. Preferred alkyl groups are those having 1–8 C atoms, especially those having 1–4 C atoms, and particularly methyl.

X* is $C_3-C_6$-alkenyl is, for example, allyl, 2-butenyl or 2-hexenyl, especially allyl.

X* as $C_3-C_4$-alkynyl is, for example, propargyl.

If X* is $C_2-C_{21}$-alkoxyalkyl, the alkyl moiety can contain 1–3 C atoms, and the alkoxy moiety can consist of 1–18 C atoms, such as in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl; to be given special mention are compounds wherein X* is an alkoxyalkyl group having 2–6 C atoms.

X* is $C_7-C_8$-aralkyl is, for example, benzyl or α-phenylethyl.

If X* is the —CH$_2$COOR$_{10*}$ group, $R_{10*}$ as $C_1C_{12}$-alkyl is, for example, methyl, ethyl, isopropyl, n-butyl, isobutyl, t-butyl, isopentyl, n-octyl, n-decyl or n-dodecyl. $R_{10*}$ is preferably $C_1-C_4$-alkyl. $R_{10*}$ is $C_3-C_6$-alkenyl is, e.g., allyl, 2-butenyl or 2-hexenyl. As $C_7-C_8$-aralkyl, $R_{10*}$ is, e.g., benzyl or α-phenylethyl.

If X* is the —CH$_2$—CH(R$_{11*}$)—OR$_{12*}$ group, $R_{11*}$ is hydrogen, methyl or phenyl, especially hydrogen. As aliphatic, aromatic, alicyclic or araliphatic $C_1-C_{18}$-acyl radical, $R_{12*}$ is optionally substituted in the aromatic moiety with chlorine, $C_1-C_4$-alkyl, such as methyl, ethyl, n-propyl or t-butyl, or with $C_1-C_8$-alkoxy, such as methoxy, ethoxy, butoxy or octoxy, and/or with hydroxyl, for example acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)-propionyl, phenylacetyl, cinnamoyl, hexahydrobenzoyl, 1- or 2-naphthoyl or decahydronaphthoyl.

$R_{16*}$ and $R_{17*}$ as $C_1-C_{17}$-alkyl have in particular the same meaning as X* as alkyl, having especially 1–12 C atoms, preferably 1–8 C atoms, particularly methyl; as $C_7-C_9$-alkylphenyl they are, e.g., methylphenyl, ethylphenyl or propylphenyl; as $C_{11}-C_{14}$-(hydroxy) (alkyl)-phenyl they are in particular 4-hydroxy-3,5-dialkyl-phenyl, wherein alkyl has in particular 1–8 C atoms, especially 1–4 C atoms, such as methyl or especially tert.-butyl, such as likewise in $C_{12}-C_{16}$(hydroxy)(alkyl)phenylalkyl, particularly 4-hydroxy-3,5-dialkylbenzyl, -phenethyl or -β-phenylpropyl.

$R_{15*}$ as alkyl having 1–20 C atoms can be, for example, one of the alkyl groups mentioned above for X*; it can also be branched-chain alkyl such as isopropyl, isopentyl, 2-ethylbutyl, 2-ethylhexyl or isononyl, or a higher alkyl radical, such as n-hexadecyl, n-octadecyl or n-eicosyl.

As a substituted or interrupted alkyl group, $R_{15*}$ can be, for example, one of the following radicals: 2-phenoxyethyl, 2-benzoyloxyethyl, 2-p-tolyloxypropyl, cyclohexyloxymethyl, 2-(β-naphthoxy)-ethyl, 2-phenylthioethyl, 2-(4-tert.-butylphenylthio)-ethyl, 2-acetylethyl, 2-isobutyrylethyl, 2-(dodecylcarbonyl)-ethyl, 2-cyanoethyl, cyanomethyl, 3-cyanopropyl, methoxycarbonylmethyl, dodecyloxycarbonylmethyl, 2-ethoxycarbonylethyl, 2-(cyclohexyloxycarbonyl) ethyl, 2-(tert.-butyloxycarbonyl)ethyl, 2-(octadecyloxycarbonyl)-propyl, 4-(propoxycarbonyl)-butyl, 2-acetoxyethyl, 2-(isooctanoyloxy)-propyl, 2-(octadecanoyloxy)-ethyl, 2-(cyclopentylcarbonyloxy)-ethyl, 3-benzoyloxypropyl, 2-(p-tert.-butylbenzoyloxy)-ethyl, 2-salicyloyloxy-ethyl, 2-(3,5-di-tert.-butyl-4-hydroxybenzoyloxy)-ethyl, 2-phenylacetyloxyethyl, 2-(3,5-di-tert.-butyl-4-hydroxyphenylpropionyloxy)-propyl, diethylphosphonomethyl, 2-dimethylphosphono-ethyl, 2-(dioctylphosphono)-ethyl, diphenylphosphonomethyl, 3-(diallylphosphono)-propyl, methoxymethyl, 2-butoxyethyl, 2-octadecyloxyethyl, isopropoxymethyl, 3-butylthio-propyl, 2-dodecylthioethyl, 2-(isohexylsulphinyl)-ethyl, 2-octadecylsulphonylethyl, 2-ethylsulphonyl-propyl.

$R_{15*}$ as an alkenyl or alkynyl group can be, e.g., allyl, methallyl, 2-buten-1-yl, 3-hexen-1-yl, undecenyl, oleyl, propyrgyl or 2-heptin-1-yl.

Examples of $R_{15*}$ as cycloalkyl, alkyl-cycloalkyl or cycloalkyl-alkyl are the radicals cyclopentyl, cyclohexyl, cyclooctyl, cyclododecyl, methylcyclopentyl, dimethylcyclohexyl, propylcyclooctyl, hexylcyclododecyl, cyclohexylmethyl, 3-cyclooctylpropyl or decyhydronaphthyl-α-methyl.

Examples of $R_{15*}$ as aralkyl or alkyl-aralkyl are the groups benzyl, 2-phenylethyl, 2-phenylpropyl, β-naphthylmethyl, 4-methylbenzyl, 4-butylbenzyl or 4-methylnaphthyl-1-methyl.

If n* is 2, $R_{15*}$ is a direct bond or a divalent organic radical. This can be alkylene, such as methylene, ethylene or polymethylene having up to 20 C atoms; or the alkylene radical is interrupted by 1 or 2 hetero members, such as the divalent radicals —CH$_2$O—CH$_2$—, —CH$_2$CH$_2$O—CH$_2$CH$_2$—, —CH$_2$CH$_2$—O—CH$_2$CH$_2$—O—CH$_2$CH$_2$—, —(CH$_2$)$_3$—S—(CH$_2$)$_3$—, —CH$_2$CH$_2$—S—(CH$_2$)$_4$—S—CH$_2$CH$_2$—, —CH$_2$C-

H$_2$—SO—CH$_2$CH$_2$—, —CH$_2$CH$_2$—SO$_2$—CH$_2$CH$_2$—, —CH$_2$CH$_2$—SO$_2$—(CH$_2$)$_8$—SO$_2$—CH$_2$CH$_2$—, —CH$_2$COOCH$_2$CH$_2$OOCCH$_2$, —CH$_2$CH$_2$COOCH$_2$CH$_2$OOCCH$_2$CH$_2$—, —CH$_2$CH$_2$—COO(CH$_2$)$_4$—OOC—CH$_2$CH$_2$—, CH$_2$CH$_2$OCO(CH$_2$)$_4$COOCH$_2$CH$_2$—, —CH$_2$CH$_2$OCO(CH$_2$)$_8$COOCH$_2$CH$_2$—. It can also be arene-bis-alkylene, such as p-xylylene, benzene-1,3-bis(ethylene), diphenyl-4,4'-bis(methylene) or naphthalene-1,4-bis(methylene). It can finally be alkenylene or alkynylene having 4–8 C atoms, such as 2-butenylene-1,4,2-butynylene-1,4 or 2,4-hexadiinylene-1,6.

Preferred compounds VIa of formula VIa are those wherein n* is 1 or 2, Y* is oxy or imino, R$_1$*, R$_2$*, R$_3$* and R$_4$* independently of one another are C$_1$–C$_6$-alkyl, or R$_3$* and R$_4$* together are tetramethylene or pentamethylene, R$_5$* and R$_6$* independently of one another are hydrogen or C$_1$–C$_5$-alkyl, R$_7$* and R$_8$* independently or one another are C$_1$–C$_4$-alkyl, R$_9$* is hydrogen, X* is hydrogen, oxyl, C$_1$–C$_8$-alkyl, C$_3$–C$_4$-alkenyl or alkynyl, C$_6$–C$_6$-alkoxyalkyl, C$_7$–C$_8$-aralkyl, or one of the groups —CH$_2$—COOR$_{10}$* or —CH$_2$—CH(R$_{11}$*)—OR$_{12}$*, wherein R$_{10}$* is C$_1$–C$_4$-alkyl, C$_3$–C$_4$-alkenyl, phenyl, C$_7$–C$_8$-aralkyl or cyclohexyl; and R$_{11}$* is hydrogen, methyl or phenyl; and R$_{12}$* is hydrogen or an aliphatic, aromatic, alicyclic or araliphatic acyl group having 1–18 C atoms, wherein the aromatic moiety can optionally be substituted with chlorine, C$_1$–C$_4$-alkyl, C$_1$–C$_8$-alkoxy and/or hydroxyl; R$_{14}$* is cyano, —CO—R$_{16}$* having the above meaning, —SO$_2$—R$_{17}$* with the above meaning or —P(=O) (OR$_{18}$*)$_2$ with the above meaning; and R$_{15}$*, if n* is 1, is hydrogen, a radical of formula VIc with the above meaning, C$_1$–C$_{18}$-alkyl, C$_3$–C$_4$-alkenyl, propargyl, benzyl, phenyl, C$_1$–C$_4$-alkyl substituted by one of the groups —CN, —C(=O)OR$_{19}$*, —O—C(=O)R$_{20}$* or —P(=O)(OR$_{12}$*)$_2$ having the above meanings, or a radical of formula VId having the above meaning, or together with R$_{16}$* it is trimethylene or tetramethylene which is optionally substituted as described above; or, if n* is 2, it is C$_2$–C$_6$-alkylene or C$_8$–C$_{14}$-arene-bis-alkylene.

Particularly preferred compounds VIb of formula VIa are those wherein n* is 1 or 2, Y* is oxy or imino, R$_1$* and R$_3$* are methyl or ethyl, R$_2$* and R$_4$* are methyl, and R$_5$*, if R$_1$* is methyl, is hydrogen, or, if R$_1$* is ethyl, it is methyl, R$_6$* is hydrogen, R$_7$* and R$_8$* independently of one another re C$_1$–C$_4$-alkyl, and R$_9$* is hydrogen, whereby the benzyl radical, which carries R$_7$*, R$_8$* and R$_9$*, is a 4-OH-benzyl, X* is hydrogen, C$_1$–C$_4$-alkyl, allyl, propargyl or C$_2$–C$_6$-alkoxyalkyl, or one of the groups —CH$_2$—COOR$_{10}$* or —CH$_2$—CH(R$_{11}$*)—OH, wherein R$_{10}$* is C$_1$–C$_4$-alkyl, R$_{11}$* is hydrogen or methyl, R$_{14}$* is cyano, —CO—R$_{16}$* having the above meaning or —SO$_2$—R$_{17}$* having the above meaning, and R$_{15}$*, if n* is 1, is hydrogen, 4-OH-3,5-di-C$_1$–C$_4$-alkyl-benzyl, C$_1$–C$_{12}$-alkyl, C$_3$–C$_4$-alkenyl, propargyl, benzyl, phenyl, or a radical or formula VIf or VIg

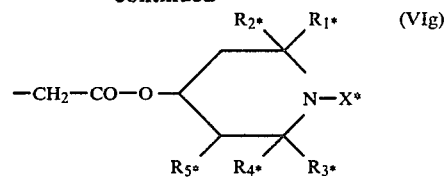

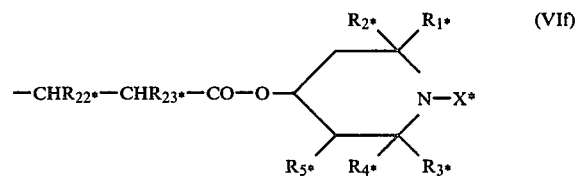

wherein R$_1$*, R$_2$*, R$_3$*, R$_4$*, R$_5$* and X* have the aforesaid preferred meanings given under VIa, and R$_{22}$* and R$_{23}$* are hydrogen or methyl, or together with R$_{16}$* are trimethylene or tetramethylene, which is optionally substituted as described in the foregoing; or, if n* is 2, it is C$_2$–C$_6$-n-alkylene or C$_8$–C$_{14}$-arene-bis-alkylene.

To be particularly emphasised are compounds VIa of formula VIa wherein n* is 1 to 2, Y* is oxy or imino, R$_1$*, R$_2$*, R$_3$* and R$_4$* are methyl, and R$_5$* and R$_6$* are hydrogen, or R$_1$* and R$_3$* are ethyl, R$_2$*, R$_4$* are methyl, and R$_6$ is hydrogen, R$_7$* and R$_8$* are methyl or tert.-butyl, R$_9$* is hydrogen, whereby the benzyl carrying R$_7$*, R$_8$* and R$_9$* is a 4-OH benzyl, X* is hydrogen or methyl, R$_{14}$* is cyano, —CO—R$_{16}$* with R$_{16}$ being C$_1$–C$_6$-alkyl, or C$_1$–C$_6$-alkylsulphonyl, and R$_{15}$*, if n* is 1, is hydrogen, 4-OH-3,5-di-tert.-butyl-benzyl, C$_1$–C$_{12}$ n-alkyl, benzyl, phenyl, optionally N-methylated (2,2,6,6-tetramethyl-piperidinyl-4)-oxycarbonylmethyl or optionally N-methylated (2,3,6-triethyl-2,6-dimethyl-piperidinyl-4)-oxycarbonylmethyl, or together with R$_{16}$* it is trimethylene or tetramethylene; or, if n* is 2, it is C$_2$–C$_6$-n-alkylene.

Compounds amongst these to be especially emphasised are compounds VIa of formula VIa wherein n* is 1, Y* is oxy, R$_1$*, R$_2$*, R$_3$*, R$_4$*, R$_5$*, R$_6$*,R$_7$*,R$_8$*, R$_9$*, X* and R$_{15}$* have the preferred meanings given under VIa, R$_{14}$* is cyano or —CO—R$_{16}$*, wherein R$_{16}$* is C$_1$–C$_6$-alkyl, or together with R$_{15}$* trimethylene or tetramethylene.

Preferably in the complexes of formula VI, R$_{27}$ is hydrogen, R$_{28}$ is hydrogen or methyl, R$_{29}$ and R$_{31}$ are methyl or ethyl, R$_{30}$ and R$_{32}$ are methyl, R$_{33}$ is hydrogen, oxyl, methyl, allyl, benzyl, alkoxycarbonylmethyl having 1–4 C atoms in the alkoxy moiety, 2-hydroxyethyl, 2-alkanoyloxyethyl having 1–4 C atoms in the alkanoyloxy moiety, 2-benzoyloxyethyl, whereby R$_{33}$ is in particular hydrogen or methyl, R$_{34}$ is hydrogen or methyl, q''' is 1 or 2, and R$_{35}$, if q''' is 1, alkanoyl having 2–18 C atoms, benzoyl, benzoyl having 1–3 substituents which are identical or different and are: alkyl having 1–4 C atoms and/or hydroxyl or β-(3,5-di-tert.-butyl-4-hydroxy-phenyl)-propionyl, methylsulphonyl, phenylsulphonyl, tolylsulphonyl, alkylcarbamoyl having 1–12 C atoms in the alkyl moiety phenylcarbamoyl or cyclohexylcarbamoyl, and R$_{35}$, if q''' is 2, is carbonyl, alkylenedicarbonyl having 1–10 C atoms in the alkylene moiety, phenylenedicarbonyl hexamethylene-diaminocarbonyl, 2,4-tolylene-di-aminocarbonyl or 4,4'-diphenylenemethane-di-aminocarbonyl, such as is illustrated by 4-acetamido-2,6-diethyl-2,3,6-trimethylpiperidine, 4-benzamido-2,2,6,6-tetramethyl-piperidine or N,N'-bis(2,2,6,6-tetramethyl-4-piperidyl)-succinamide.

Also preferred are metal complexes of formula VII

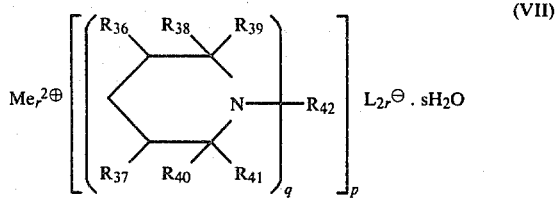

wherein Me, p, q, r, s and L have the meanings given in the foregoing as being preferred, and the meanings of the other symbols are as follows: $R_{36}$ and $R_{37}$ independently of one another are hydrogen, alkyl, alkenyl, alkynyl or aralkyl, $R_{38}$ and $R_{39}$ independently of one another are alkyl, $R_{40}$ is alkyl, phenyl, benzyl or phenethyl, $R_{41}$ is alkyl, or $R_{40}$ and $R_{41}$ together are tetramethylene or pentamethylene, and $R_{42}$, where q is 1, is hydrogen, oxyl, alkyl, alkenyl, alkynyl, alkoxyalkyl, aralkyl, 2,3-epoxypropyl, alkoxycarbonylmethyl, alkenyloxycarbonylmethyl, phenoxycarbonylmethyl, aralkoxycarbonylmethyl, cyclohexylcarbonylmethyl, 2-hydroxyethyl, 2-hydroxypropyl, 2-phenyl-2-hydroxyethyl, 2-acyloxyethyl, 2-acyloxypropyl or 2-phenyl-2-acyloxy-ethyl, and $R_{42}$, where q is 2, is alkylene, 1,4-but-2-enylene, alkylene-di-(carbonyloxyethylene), alkylene-di-(carbonyloxy-methylethylene), wherein methyl is in the α-position with respect to carbonyloxy, alkylene-di-(carbonyl-phenylethylene), wherein phenyl is in the α-position with respect to carbonyloxy, alkylene-dioxycarbonylmethyl or xylylene-di-oxycarbonylmethyl.

Alkyl $R_{36}$ and $R_{37}$ have in particular 1-5 C atoms, such as methyl. Alkenyl $R_{36}$ and $R_{37}$ have in particular 3-4 C atoms, such as allyl. Alkynyl $R_{36}$ and $R_{37}$ have in particular 3-4 C atoms, such as propargyl. Aralkyl $R_{36}$ and $R_{37}$ have in particular 7-8 C atoms, such as benzyl. Alkyl $R_{38}$ and $R_{39}$ have in particular 1-6 C atoms, such as methyl or ethyl. Alkyl $R_{40}$ has in particular 1-9 C atoms, such as methyl. Alkyl $R_{41}$ has in particular 1-6 C atoms, such as methyl. Alkyl $R_{42}$ has in particular 1-8 C atoms, such as methyl. Alkenyl $R_{42}$ has in particular 3-6 C atoms, such as allyl. Alkynyl $R_{42}$ has in particular 3-4 C atoms, such as propargyl. Alkoxyalkyl $R_{42}$ has in particular 2-21 C atoms, especially 2-12 C atoms, such as 2-methoxyethyl. Aralkyl $R_{42}$ has in particular 7-8 C atoms, such as benzyl. Alkoxycarbonylmethyl $R_{42}$ has in the alkoxy moiety in particular 1-12 C atoms, such as methoxycarbonylmethyl. Alkenyloxycarbonylmethyl $R_{42}$ has in the alkenyloxy moiety in particular 3-6 C atoms, such as allyloxycarbonylmethyl. Aralkoxycarbonylmethyl $R_{42}$ has in the aralkoxy moiety in particular 7-8 C atoms, such as benzyloxycarbonylmethyl. 2-Acyloxyethyl, 2-acyloxypropyl and 2-phenyl-2-acyloxy-ethyl $R_{42}$ contain as acyl the radical of an aliphatic, aromatic, alicyclic or araliphatic carboxylic acid having up to 18 C atoms, such as alkanoyl, e.g. acetyl or propionyl, benzoyl that is optionally substituted by chlorine, alkyl having 1-4 C atoms, alkoxy having 1-8 C atoms and/or hydroxyl, such as 3,5-di-tert.-butyl-4-hydroxybenzoyl, cyclohexylcarbonyl or aralkylcarbonyl, such as benzylcarbonyl or phenethylcarbonyl, which is optionally substituted in the phenyl moiety by chlorine, alkyl having 1-4 C atoms, alkoxy having 1-8 C atoms and/or hydroxyl, such as β-(3,5-di-tert.-butyl-4-hyroxy-phenyl)-propionyl. Alkylene $R_{42}$ has in particular 4-8 C atoms, such as tetramethylene. Alkylene has in the mentioned alkylene-di-(carbonyloxyethylene)-radicals $R_{42}$ in particular 1-10 C atoms, such as methylene or ethylene. And alkylene has in alkylene-di-oxycarbonyl methyl $R_{42}$ especially 2-8 C atoms, such as ethylene.

Preferably in complexes of formula VII, $R_{36}$ is hydrogen, $R_{37}$ is hydrogen or methyl, $R_{38}$ and $R_{40}$ are methyl or ethyl, $R_{39}$ and $R_{41}$ are methyl, q is 1, and $R_{42}$ is hydrogen, methyl, 2-alkanoyloxy-ethyl having 2-12 C atoms in the alkanoyloxy moiety, 2-benzoyloxy-ethyl, 2-(3,5-di-tert.-butyl-4-hydroxybenzoyloxy)-ethyl or 2[β-(3,5-di-tert.-butyl-4-hydroxyphenyl)-propionyloxy]-ethyl, and in particular $R_{42}$ is hydrogen or methyl, such as is illustrated by 2,6-diethyl-2,3,6-trimethyl-piperidine, 2,2,6,6-tetramethyl-piperidine or 1,2,2,6,6-pentamethyl-piperidine. If $R_{38}$ and $R_{40}$ are ethyl, $R_{37}$ is especially methyl. If $R_{38}$ and $R_{40}$ are methyl, $R_{37}$ is in particular hydrogen.

Metal complexes also preferred are those of formula VIII

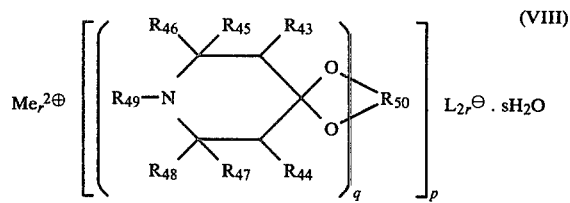

wherein Me, p, q, r, s and L have the meanings given in the foregoing as being preferred, and the symbols otherwise have the following meanings: $R_{43}$ and $R_{44}$ independently of one another are hydrogen, alkyl, alkenyl, akynyl or aralkyl, $R_{45}$ and $R_{46}$ each independently represent alkyl, $R_{47}$ is alkyl, $R_{48}$ is alkyl, phenyl, benzyl or phenethyl, or $R_{47}$ and $R_{48}$ together are tetramethylene or pentamethylene, $R_{49}$ is hydrogen, oxyl, alkyl, akenyl, alkynyl, alkoxyalkyl, aralkyl, 2,3-epoxypropyl, alkoxycarbonylmethyl, alkenyloxycarbonylmethyl, phenoxycarbonylmethyl, aralkoxycarbonylmethyl, cyclohexyloxycarbonylmethyl, 2-hydroxyethyl, 2-hydroxypropyl, 2-phenyl-2-hydroxy-ethyl, 2-acyloxyethyl, 2-acyloxypropyl or 2-phenyl-2-acyloxyethyl, and $R_{50}$, if q is 1, is optionally substituted ethylene, o-phenylene, optionally substituted 1,3-propylene, and $R_{50}$, if q is 2, is

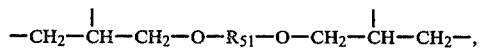

$(CH_2)_2C(CH_2—)_2$, $(—CH_2)_2CR_{55}—CH_2—O—R_{51}—O—CH_2—CR_{53}(CH_2—)_2$, wherein $R_{51}$ is a divalent acyl radical, and $R_{53}$ is hydrogen, methyl or ethyl.

Alkyl $R_{43}$ and $R_{44}$ have in particular 1-5 C atoms, such as methyl. Alkenyl $R_{43}$ and $R_{44}$ have in particular 3-4 C atoms, such as allyl. Alkynyl $R_{43}$ and $R_{44}$ have in particular 3-4 C atoms, such as propargyl. Aralkyl $R_{43}$ and $R_{44}$ have in particular 7-8 C atoms, such as benzyl. Alkyl $R_{45}$ and $R_{46}$ have in particular 1-6 C atoms, such as methyl or ethyl. Alkyl $R_{47}$ has in particular 1-6 C atoms, such as methyl or ethyl. Alkyl $R_{48}$ has in particular 1-9 C atoms, such as methyl or ethyl. Alkyl $R_{49}$ has in particular 1-8 C atoms, such as methyl. Alkenyl $R_{49}$ has especially 3-6 C atoms, such as propargyl. Alkoxyalkyl $R_{49}$ has in particular 2-21 C atoms, especially 2-12 C atoms, such as 2-methoxyethyl. Aralkyl $R_{49}$ has in particular 7-8 C atoms, such as benzyl. Alkoxycarbonylmethyl $R_{49}$ has in the alkyl moiety especially 1-12 C atoms, such as methoxycarbonylmethyl. Alkenyloxycarbonylmethyl $R_{49}$ has in the alkenyloxy moiety in particular 3–6 C atoms, such as allyloxycarbonylmethyl. Aralkoxycarbonylmethyl $R_{49}$ has in the aralkoxy moiety in particular 7–8 C atoms, such as benzyloxycarbonylmethyl. 2-Acyloxyethyl, 2-acyloxypropyl and 2-phenyl-2-acyloxyethyl $R_{49}$ have as acyloxy in each case that having up to 18 C atoms, such as aliphatic, aromatic, araliphatic or alicyclic acyloxy, e.g. alkanoyloxy such as acetoxy, benzoyloxy, which is optionally substituted by chlorine, alkyl having 1–4 C atoms, alkoxy having 1–8 C atoms and/or hydroxyl, such as 3,5-di-tert-butyl-4-hydroxy-benzoyloxy, benzylcarbonyloxy or phenethylcarbonyloxy, which can both be substituted in the phenyl moiety by chlorine, alkyl having 1–4 C atoms, alkoxy having 1–8 C atoms and/or hydroxyl, such as $\beta$-(3,5-di-tert-butyl-4-hydroxyphenyl)-propionyloxy, or cyclohexylcarbonyloxy. Optionally substituted ethylene $R_{50}$ is in particular —$CR_{52}R_{53}$—$CHR_{54}$—, wherein $R_{52}$ is hydrogen, methyl, acyloxymethyl, alkoxymethyl having 1–4 C atoms in the alkoxy moiety, alkenyloxymethyl having 2–4 C atoms in the alkenyloxy moiety, benzyloxymethyl or optionally substituted carbamoyloxymethyl, $R_{53}$ is hydrogen, methyl or ethyl, and $R_{54}$ is hydrogen, methyl or ethyl. Acyl in acyloxymethyl has, in particular, up to 18 C atoms, such as aliphatic, cycloaliphatic, aromatic or araliphatic acyl, e.g. alkanoyl, such as acetyl, cycloalkylcarbonyl, benzoyl which is optionally substituted by halogen, alkyl having 1–4 C atoms, and/or hydroxyl, such as 3,5-di-tert-butyl-4-hydroxy-benzoyl, aralkylcarbonyl having especially 7–8 C atoms in the aralkyl moiety, which is optionally substituted in the aryl moiety by chlorine, alkyl having 1–4 C atoms and/or hydroxyl, such as $\beta$-(3,5-di-tert-butyl-4-hydroxy-phenyl)-propionyl. And optionally substituted carbamoxymethyl is in particular N-monosubstituted, such as by alkyl having 1–12 C atoms, such as methyl, cyclohexyl, aralkyl having 7–8 C atoms, such as benzyl, or aryl having 6–12 C atoms, such as phenyl. Optionally substituted 1,3-propylene $R_{50}$ is, in particular, —$CHR_{52}$—$CH_2$—$CR_{53}R_{54}$—, or —$CHR_{53}$—$CH_2$—$CR_{52}R_{54}$—, or —$CH_2$—$CR_{52}$—$R_{53}$—$CHR_{54}$—, wherein $R_{52}$, $R_{53}$ and $R_{54}$ have the aforementioned meanings. A divalent acyl radical $R_{51}$ has in particular up to 12 C atoms, such as a radical of an aliphatic, aromatic or araliphatic dicarbonyl acid, such as alkylenedicarbonyl, e.g. malonyl or ethylenedicarbonyl, phenylenedicarbonyl or phenylenedimethylcarbonyl; or $R_{51}$ is —CONH—alkylene—NHCO—, wherein alkylene has in particular 2–8 C atoms, such as ethylene or 1,4-butylene, or —CONH—arylene—NHCO, wherein arylene has especially 6–12 C atoms, such as phenylene, or —CONH—xylylene—NHCO— or —CONH—$C_6H_5$—$CH_2$—$C_6H_5$—NHCO—.

Preferably in complexes of formula VIII, $R_{43}$ is hydrogen, $R_{44}$ is hydrogen or methyl, $R_{45}$ and $R_{47}$ are methyl, $R_{46}$ and $R_{48}$ are methyl or ethyl, $R_{49}$ is hydrogen or methyl, q is 1 or 2, and $R_{50}$, if q is 1, is ethylene, methylethylene, hydroxymethyl-ethylene, acyloxymethyl-ethylene having 2–12 C atoms in the acyl moiety, benzolyloxymethyl-ethylene which is optionally substituted in the benzoyl moiety by alkyl having 1–4 C atoms, and/or hydroxyl, $\beta$-(3,5-di-tert-butyl-4-hydroxyphenyl)-propionylmethyl-ethylene, 1,3-propylene, 2-methyl-1,3-propylene or 2-ethyl-1,3-propylene, whereby all these propylenes can be substituted in the 2-position by methyl, hydroxymethyl, acyloxymethyl having 2–12 C atoms, benzoyloxymethyl, which for its part can be substituted in the benzoyl moiety by alkyl having 1–4 C atoms and/or hydroxyl, or $\beta$-(3,5-di-tert-butyl-4-hydroxy-phenyl)-propionyloxy-methyl, and $R_{50}$, if q is 2, is (—$CH_2$)$_2$C(CH$_2$—)$_2$, such as illustrated by 8-aza-6,7,9-trimethyl-7,9-diethyl-1,4-dioxaspiro [4,5]decane, 8-aza-7,7,9,9-tetramethyl-1,4-dioxaspirol [4.5]decane or 9-aza-8,8,10,10-tetramethyl-1,5-dioxaspiro [5.5]undecane. If $R_{46}$ and $R_{48}$ are ethyl, $R_{44}$ is in particular methyl. If $R_{46}$ and $R_{48}$ are methyl, $R_{44}$ is especially hydrogen.

Also preferred, but only in second place, are metal complexes of formula IX

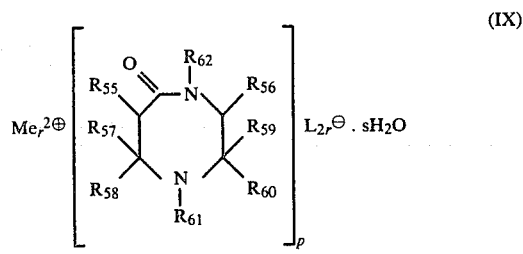

(IX)

wherein Me, p, r, s and L have the aforementioned preferred meanings, and the meanings of the other symbols are: $R_{55}$ and $R_{56}$ independently of one another are hydrogen, alkyl, alkenyl, alkynyl or aralkyl, $R_{57}$ and $R_{58}$ each independently represent alkyl, $R_{59}$ is alkyl, phenyl, benzyl or phenethyl, $R_{60}$ is alkyl, or $R_{59}$ together with $R_{60}$ is tetramethylene or pentamethylene, $R_{61}$ is hydrogen, oxyl, alkyl, alkenyl, akoxyalkyl or aralkyl, and $R_{62}$ is hydrogen, alkyl, alkenyl, propargyl, aralkyl, —$CH_2COOR_{63}$ or —$CH_2CH_2COOR_{63}$, wherein $R_{63}$ is alkyl, phenyl, benzyl, or cyclohexyl, or —$CH_2CH(R_{64})OR_{65}$ wherein $R_{64}$ is hydrogen, methyl or phenyl, and $R_{65}$ is hydrogen or acyl.

Alkyl $R_{55}$ and $R_{56}$ have in particular 1–5 C atoms, such as methyl. Alkenyl $R_{55}$ and $R_{56}$ have in particular 3–4 C atoms, such as allyl. Alkynyl $R_{55}$ and $R_{56}$ have in particular 3–4 C atoms, such as propargyl. Aralkyl $R_{55}$ and $R_{56}$ have, in particular, 7–8 C atoms, such as benzyl. Alkyl $R_{57}$ and $R_{58}$ have in particular 1–6 C atoms, such as methyl or ethyl. Alkyl $R_{59}$ has especially 1–9 C atoms, such as methyl or ethyl. Alkyl $R_{60}$ has in particular 1–6 C atoms, such as methyl or ethyl. Alkyl $R_{61}$ has in particular 1–12 C atoms, such as methyl. Alkenyl $R_{61}$ has in particular 3–6 C atoms, such as allyl. Alkoxyalkyl $R_{61}$ has in particular 2–21 C atoms, especially 2–12 C atoms, such as 2-methoxyethyl. Aralkyl $R_{61}$ has in particular 7–8 C atoms, such as benzyl. Alkyl $R_{62}$ has in particular 1–12 C atoms, such as methyl. Alkenyl $R_{62}$ has especially 3–6 Carbon atoms, such as allyl. Aralkyl $R_{62}$ has in particular 7–8 C atoms, such as benzyl. Alkyl $R_{63}$ has especially 1–8 C atoms, such as methyl. Acyl $R_{65}$ has in particular up to 18 C atoms, such as aliphatic, aromatic, araliphatic or alicyclic acyl, such as alkanoyl, e.g. acetyl or propionyl, benzoyl which can also be substituted by chlorine, alkyl having 1–4 C atoms, alkoxy having 1–8 C atoms and/or hydroxy, such as 3,5-ditert.-butyl-4-hydroxy-benzoyl, benzylcarbonyl or phenethylcarbonyl, which can both be substituted in the phenyl moiety by chlorine, alkyl having 1–4 C atoms, alkoxy having 1–8 C atoms and/or hydroxyl, such as $\beta$-(3,5-di-tert-butyl-4-hydroxyphenyl)-propionyl.

Preferably in complexes of formula IX, $R_{55}$ is hydrogen, $R_{56}$ is hydrogen or methyl, $R_{57}$ and $R_{59}$ are methyl or ethyl, $R_{59}$ and $R_{60}$ are methyl, $R_{61}$ is hydrogen, oxyl or alkyl having 1–4 C atoms, and $R_{62}$ is hydrogen, alkyl having 1–12 C atoms, allyl, benzyl, alkoxycarbonylmethyl having 1–8 C atoms in the alkoxy moiety, alkylcarbamoyl having 1–12 C atoms in the alkyl moiety, phenylcarbamoyl, chlorophenylcarbamoyl, methylphenylcarbamoyl, benzylcarbamoyl or cyclohexylcarbamoyl.

In particular, $R_{55}$ is hydrogen, $R_{56}$ is hydrogen or methyl, $R_{57}$ and $R_{59}$ are methyl or ethyl, $R_{58}$ and $R_{60}$ are methyl, $R_{61}$ is hydrogen or methyl, and $R_{62}$ is hydrogen, alkyl having 1–8 C atoms, allyl, benzyl, alkylcarbamoyl having 1–12 C atoms in the alkyl moiety, phenylcarbamoyl or cyclohexylcarbamoyl, such as is illustrated by 2,7-diethyl-2,3,7-trimethyl-1,4-diaza-5-oxo-cycloheptane, 2,2,7,7-tetramethyl-1,4-diaza-5-oxo-cycloheptane or 1,2,2,7,7-pentamethyl-1,4-diaza-5-oxo-cycloheptane. If $R_{57}$ and $R_{59}$ are ethyl, $R_{56}$ is in particular methyl. If $R_{57}$ and $R_{59}$ are methyl, $R_{56}$ is especially hydrogen.

Also preferred are metal complexes of formula X

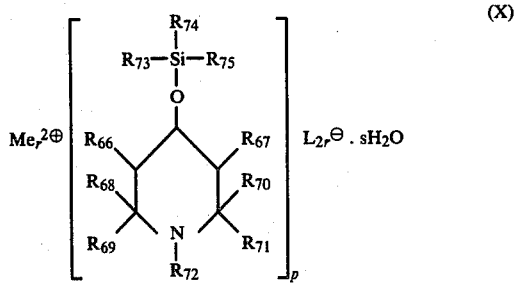

(X)

wherein Me, p, r, s and L have the meanings given in the foregoing as being preferred, and the meanings of the other symbols are as follows: $R_{66}$ and $R_{67}$ independently of one another are hydrogen, alkyl, alkenyl, alkynyl or aralkyl, $R_{68}$, $R_{69}$ and $R_{70}$ independently of one another are alkyl, $R_{71}$ is alkyl, phenyl, benzyl or phenethyl, or $R_{70}$ and $R_{71}$ together are tetramethylene or pentamethylene, $R_{72}$ is hydrogen, oxyl, alkyl, alkenyl, alkoxyalkyl, aralkyl, alkoxycarbonylmethyl, alkenyloxycarbonylmethyl, phenoxycarbonylmethyl, methyl, aralkoxycarbonylmethyl, cyclohexyloxycarbonylmethyl, or —CH$_2$—CH(R$_{76}$)OR$_{77}$, wherein $R_{76}$ is hydrogen, methyl or phenyl, and $R_{77}$ is hydrogen or acyl, $R_{73}$ is alkyl, methyl, phenyl or vinyl, $R_{74}$ and $R_{75}$ independently of one another are hydrogen, methyl, phenyl, vinyl, alkoxy, alkoxyalkoxy, cyclohexyloxy, aralkoxy, aryloxy, 1R$_{72}$-2-R$_{68}$-2-R$_{69}$-3-R$_{66}$-5-R$_{67}$-6-R$_{70}$-6-R$_{71}$-4-piperidyloxy, or, if $R_{73}$ and $R_{74}$ are hydrogen, methyl, phenyl or vinyl, $R_{75}$ is also a radical of formula XI

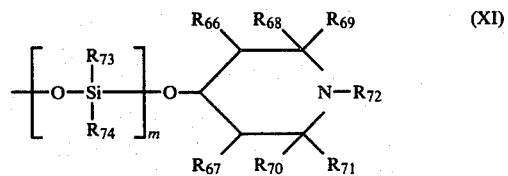

(XI)

wherein m is an integer from 1–10.

Alkyl $R_{66}$ and $R_{67}$ have in particular 1–5 C atoms, such as methyl. Alkenyl $R_{66}$ and $R_{67}$ have in particular 3–4 C atoms, such as allyl. Alkynyl $R_{66}$ and $R_{67}$ have in particular 3–4 C atoms, such as propargyl. Aralkyl $R_{66}$ and $R_{67}$ have in particular 7–8 C atoms, such as benzyl. Alkyl $R_{68}$, $R_{69}$ and $R_{70}$ have in particular 1–6 C atoms, such as methyl or ethyl. Alkyl $R_{71}$ has in particular 1–9 C atoms, such as methyl or ethyl. Alkyl $R_{72}$ has in particular 1–12 C atoms, such as methyl. Alkenyl $R_{72}$ has in particular 3–6 C atoms, such as allyl. Alkoxyalkyl $R_{72}$ has in particular 2–14 C atoms, such as 2-methoxyethyl. Aralkyl $R_{72}$ has in particular 7–8 C atoms, such as benzyl. Alkoxycarbonylmethyl $R_{72}$ has in the alkoxy moiety in particular 1–8 C atoms, such as methoxycarbonylmethyl. Alkenyloxycarbonylmethyl $R_{72}$ has in the alkenyloxy moiety especially 3–6 C atoms, such as allyloxycarbonylmethyl. Aralkoxycarbonylmethyl $R_{72}$ has in the aralkoxy moiety in particular 7–8 C atoms, such as benzyloxycarbonylmethyl. Acyl $R_{77}$ has especially up to 18 C atoms, such as aliphatic, aromatic, araliphatic or alicyclic acyl, such as alkanoyl, e.g. acetyl or propionyl, benzoyl that is optionally substituted by chlorine, alkyl having 1–4 C atoms, alkoxy having 1–8 C atoms, and/or hydroxyl, such as 3,5-di-tert-butyl-4-hydroxy-benzoyl, benzylcarbonyl or phenethylcarbonyl, which are both optionally substituted by chlorine, alkyl having 1–4 C atoms, alkoxy having 1–8 C atoms, and/or hydroxy, such as β-(3,5-di-tert-butyl-4-hydroxyphenyl)-propionyl, or cyclohexylcarbonyl. Alkoxy $R_{74}$ has in particular 1–8 C atoms, such as methoxy. Alkoxyalkoxy $R_{74}$ and $R_{75}$ have in particular 3–10 C atoms, such a 2-methoxyethoxy. Aralkoxy $R_{74}$ and $R_{75}$ have in particular 7–8 C atoms, such as benzyloxy or phenylethyloxy. Aryloxy $R_{74}$ and $R_{75}$ are, in particular, phenoxy which is optionally substituted by chlorine, alkyl having 1–4 C atoms or alkoxy having 1–4 C atoms.

Preferably, in complexes of formula X, $R_{66}$ is hydrogen, $R_{67}$ is hydrogen or methyl, $R_{68}$ and $R_{70}$ are methyl or ethyl, $R_{69}$ and $R_{71}$ are methyl, $R_{72}$ is hydrogen or alkyl having 1–4 C atoms, $R_{73}$ and $R_{74}$ are methyl or phenyl, and $R_{75}$ is methyl, phenyl or 1-R$_{72}$ -2-R$_{68}$-2-methyl-5-R$_{67}$-6-R$_{70}$-6-methyl-4-piperidyloxy, with the aforementioned meanings for $R_{67}$, $R_{68}$, $R_{70}$ and $R_{72}$.

Particularly preferably, $R_{66}$ is hydrogen, $R_{67}$ is hydrogen or methyl, $R_{68}$ and $R_{70}$ are methyl or ethyl, $R_{69}$ and $R_{71}$ are methyl, $R_{72}$ is hydrogen or methyl, $R_{73}$ and $R_{74}$ are methyl or phenyl, and $R_{75}$ is methyl, phenyl or 1-R$_{72}$-2-R$_{68}$-2-methyl-5-R$_{67}$-6-R$_{70}$-6-methyl-4-piperidyloxy, with the aforestated meanings for $R_{67}$, $R_{68}$, $R_{70}$ and $R_{72}$, such as is illustrated by 2,2,6,6-tetramethyl-4-trimethylsiloxypiperidine, diphenylbis-(2,2,6,6-tetramethylpiperidine-4-oxy)-silane, dimethylbis-(2,2,6,6-tetramethyl-piperidine-4-oxy)-silane or 1,2,2,6,6-pentamethyl-4-triphenylsiloxy-piperidine. If $R_{68}$ and $R_{70}$ are ethyl, $R_{67}$ is in particular methyl. If $R_{68}$ and $R_{70}$ are methyl, $R_{67}$ is especially hydrogen.

The complexes according to the invention optionally contain various stereoisomers which are likewise subject of the invention. On synthesis of the complexes of the invention there is frequently obtained a mixture of stereoisomers; in particular the starting materials can already be mixtures of stereoisomers. Such mixtures can, if desired, be separated in a manner known per se at any given stage of synthesis.

Preferably in the aforesaid preferred metal complexes, especially in those of formulae III-X, Me$^{2\oplus}$ is zinc, cobalt and especially nickel, r is 1 or 2, q is 1 or 2, p is 1, s is a value from 0–2, and L is a singly charged anion of an alkanecarboxylic acid having 1–12 C atoms, or in particular of an enol corresponding to formula II, as given in the foregoing, especially the anion of acetylacetonate.

Also preferred however are those of the aforementioned compounds wherein Me is a trivalent cation, namely aluminum or chromium, and the other symbols have the aforesaid meanings.

The following may for example be emphasised:

(1) (2,2,6,6-tetramethyl-4-stearyloxy-piperidine)-nickel-di-acetylacetonate,
(2) [bis-(2,2,6,6-tetramethyl-4-piperidyl)-sebacate]-di-(zinc-di-acetate),
(3) [bis-(2,2,6,6-tetramethyl-4-piperidyl)-sebacate]-di-(nickel-di-oenanthate),
(4) [bis-(2,2,6,6-tetramethyl-4-piperidyl)-sebacate]-di-(zinc-di-laurate),
(5) [bis-(2,2,6,6-trimethyl-4-piperidyl)-sebacate]-di-(nickel-di-laurate),
(6) (2,2,6,6-tetramethyl-4-benzoyloxy-piperidine)-nickel-di-acetylacetonate,
(7) (1,2,2,6,6-pentamethyl-4-stearoyloxy-piperidine)-nickel-di-acetylacetonate,
(8) (2,2,6,6-tetramethyl-4-benzoylamido-piperidine)-nickel-di-acetylacetonate,
(9) (3-n-octyl-7,7,9,9-tetramethyl-1,3,8-triazaspirol [4.5]decane-2,4-dione)-nickel-di-acetylacetonate,
(10) [2,2,6,6-tetramethylpiperidine-4-spiro-2'-(1',3'-dioxane)-5'-spiro -5"-(1",3"-dioxane)-2"-spiro-4'''-(2''', 2''', 6''', 6'''-tetramethylpiperidine]-di-(nickel-di-acetylacetonate),
(11) (8-aza-2-hydroxymethyl-7,7,9,9-tetramethyl-1,4-dioxaspiro [4.5]decane-nickel-di-acetylacetonate,
(12) (2,3,6-trimethyl-2,6-diethyl-4-benzoylamidopiperidine)-nickel-di-acetylacetonate,
(13) (2,2,6,6-tetramethyl-4-acetamidopiperidine)-nickel-di-benzoylacetonate,
(14) (2,6-diethyl-2,3,6-trimethyl-4-acetamidopiperidine)-Co(II)-di-acetylacetonate,
(15) (8-aza-7,9-diethyl-6,7,9-trimethyl-1,4-dioxa-spiro [4.5]decane-Ni-di-ethylacetylacetate,
(16) (2,6-diethyl-2,3,6-trimethyl-4-benzoyloxypiperidine)-Ni-di-2-acetyl-phenolate,
(17) (2,6-diethyl-2,3,6-trimethyl-4-benzoylamidopiperidine)-Co(II)-di-oenanthate,
(18) (2,2,6,6-tetramethyl-4-benzoyloxypiperidine-1-oxyl)-Ni-di-acetylacetonate,
(19) (2,2,2',2',6,6,6',6'-octamethyl-4,4'-dihydroxy-4,4'-biperidine)-di-(Ni-di-acetylacetonate),
(20) (2,2,6,6-tetramethyl-4-triphenylsiloxypiperidine)-(1,3-di-phenyl-propanedione(1,3)ato)-Ni,
(21) [diphenyl-bis-(2,2,6,6-tetramethyl-piperidine-4-oxy)-silane]-di-(Co(II)-di-acetylacetonate),
(22) [bis(2,2,6,6-tetramethyl-4-piperidinyl)-diethyl-malonate]-di-(Zn-di-laurate),
(23) [N,N'-bis-(2,2,6,6-tetramethyl-4-piperidinyl)-oxalamide]-di-(Ni-di-benzoylacetylacetate),
(24) (2,2,6,6-tetramethyl-4-benzamidopiperidine)-Ni-di-(2-benzoyl-5-n-octaxyphenolate),
(25) (2,2,6,6-tetramethyl-4-benzoyloxypiperidine)-Al(III)-tris-sec-butylate,
(26) (2,2,6,6-tetramethyl-4-stearoyloxypiperidine)-Cr(III)-tris-stearate,
(27) (2,2,6,6-tetramethyl-4-stearoyloxypiperidine)-Ca-di-acetyl-acetonate, as well as the complexes mentioned in the Examples.

The metal complexes of formula I can be produced in a manner known per se, particularly by a process wherein a metal compound of formula XII $$Me^{w\oplus}L_w^{\ominus} \qquad (XII),$$

or a hydrate thereof, is reacted with an amine of formula XIII

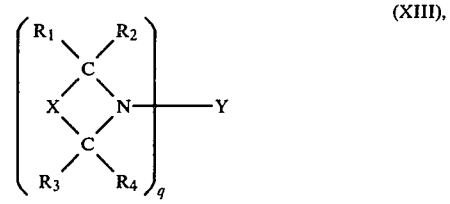

or with a hydrate thereof, wherein Me, L, X, $R_1$, $R_2$, $R_3$, $R_4$, q and Y have the aforesaid meanings.

Advantageously there are used about r moles of the metal compound XII and about p moles of the amine XIII. The reaction can be advantageously performed in an inert solvent by bringing together solutions of the two reactants, especially in the stochiometrically required ratio, and then removing the solvent, e.g. by evaporation.

Suitable solvents are, in particular, inert organic solvents such as hydrocarbons, e.g. light petrol, cyclohexane, benzene, toluene or xylene, chlorinated hydrocarbons such as chloroform, ketones such as acetone or methyl ethyl ketone, esters such as ethyl acetate, ethers such as dioxane, tetrahydrofuran, ethylene glycol dimethyl ether, dimethylene glycol dimethyl ether, ethylene glycol monomethyl ether or ethylene glycol monoethyl ether, alcohols such as alkanols, e.g. methanol, ethanol or isopropanol, nitriles such as acetonitrile, or mixtures of such solvents. Inert solvents are inert particularly under the reaction conditions.

The starting materials of formulae XII and XIII are known and are in many cases available commercially, or, if the one or other of them should be new, they can be produced by methods known per se.

Thus, for example, 1-H-4-oxo-piperidines carrying in the 2- and 6-position various substituents can be produced by reaction of a ketone $R_1$—CO—$R_2$ with ammonia. The formed pyrimidine is hydrolysed, as described in Helv.Chim.Acta 30, 114 (1947), to a γ-aminoketone, which is then reacted in a second stage with ammonia and a ketone $R_3$—CO—$R_4$ (see Monatsh.Chemie 88, 464 (1957)). Hydrolysis then yields the desired NH compounds, which can serve as starting materials for the various amines of formula XIII; e.g. as 2,6-dimethyl-2,6-di-$R_{10}$-3-$R_{11}$-4-oxo-piperidine for piperidines such as are obtained in formula III; as 2-methyl-2-$R_{12}$-3-$R_{15}$-4-oxo-6-$R_{13}$-6-$R_{14}$-piperidine for piperidines such as are obtained in formula IV; 2-$R_{21}$-2-$R_{22}$-3-$R_{19}$-4-oxo-5-$R_{20}$-6-$R_{23}$-6-$R_{24}$-piperidine for piperidines such as are obtained in formula V; 2-$R_{29}$-2-$R_{30}$-3-$R_{27}$-4-oxo-5-$R_{28}$-6-$R_{31}$-6-$R_{32}$-piperidine for piperidines such as are obtained in formula VI; as 2-$R_{40}$-2-$R_{41}$-3-$R_{37}$-4-oxo-5-$R_{36}$-6-$R_{38}$-6-$R_{39}$-piperidine for piperidines such as are obtained in formula VII; as 2-$R_{45}$-2-$R_{46}$-3-$R_{43}$-4-oxo-5-$R_{44}$-6-$R_{47}$-6-$R_{48}$-piperidine for piperidines such as are obtained in formula VIII; and as 2-$R_{57}$-2-$R_{58}$-3-$R_{55}$-4-oxo-5-$R_{56}$-6-$R_{59}$-6-$R_{60}$-piperidine for amines such as are obtained in formula IX. The respective further conversions of these intermediates can be performed in a manner analogous to that in the case of the sterically hindered amines mentioned at the beginning as prior art.

The metal complexes of formula I according to the invention are able to protect a large number of organic polymers from damage caused by light, and at the same time they have good extraction stability and compatibility with the polymeric substrates. Polymers which can be stabilised in this way are, for example, the following:

1. Polymers of mono- and diolefins, for example polyethylene (which can be optionally crosslinked), polypropylene, polyisobutylene, polymethylbutene-1, polymethylpentene-1, polyisoprene or polybutadiene.
2. Mixtures of the polymers given under (1), e.g. mixtures of polypropylene with polyethylene or with polyisobutylene.
3. Copolymers of mono- and diolefins, such as ethylenepropylene copolymers, propylene-butene-1 copolymers, propylene-isobutylene copolymers, ethylene-butene-1 copolymers, as well as terpolymers of ethylene with propylene and a diene, such as hexadiene, dicyclopentadiene, or ethylidenenorbornene.
4. Polystyrene.
5. Copolymers of styrene or α-methylstyrene with dienes or acryl derivatives, such as styrene-butadiene, styreneacrylonitrile, styrene-acrylonitrile-methylacrylate; mixtures of high impact strength composed of styrene copolymers and another polymer, such as a polyacrylate, a diene polymer or an ethylene-propylene-diene terpolymer; as well as block copolymers of styrene, such as styrene-butadiene-styrene, styrene-isoprene-styrene or styrene-ethylene/butylene-styrene.
6. Graft copolymers of styrene, such as styrene on polybutadiene, styrene and acrylonitrile on polybutadiene, as well as mixtures with the copolymers mentioned under (5), such as are known as so-called ABS polymers.
7. Polyurethanes and polyureas.

The compounds of formula I are incorporated into the substrates at a concentration of 0.005 to 5 percent by weight, calculated on the basis of the material to be stabilised.

Preferably, 0.01 to 1.0% by weight, particularly preferably 0.02 to 0.5% by weight, of the compounds, relative to the material to be stabilised, is incorporated into this material. Incorporation can be effected, for example, by the mixing of at least one of the compounds of formula I and, optionally, further additives into the melt, by methods customarily used in the art, either before or during moulding, or by application of the dissolved or dispersed compounds to the polymers, optionally with subsequent removal of the solvent by evaporation.

The compounds of formula I may also be added before or during polymerisation, whereby as a result of a possible incorporation into the polymer chian there can be obtained stabilised substrates in which the stabilisers are not volatile or capable of extraction.

The addition can however also be effected by incorporating the constituents of formulae XII and XIII into the substrate, whereby there are used in particular the anhydrous forms of the constituents of the formulae XII and XIII. The symbols in the formulae XII and XIII have in this case the aforesaid meanings, especially those given as being preferred.

The invention accordingly relates also to a stabiliser mixture of a compound of formula XII and a compound of formula XIII, wherein Me, L, X, $R_1$, $R_2$, $R_3$, $R_4$, q and Y have the aforesaid meanings, especially the aforestated preferred meanings, especially as per formulae III, IV, VI, VII, VIII, X and, especially, V.

In particular there can also be preferably used the constituents from which are composed the complexes mentioned generally, and especially those mentioned specifically, in the foregoing, as well as the complexes given in the Examples.

The ratio of the compounds of formulae XII and XIII, including the preferred meanings above, especially as per formulae III, IV, V, VI, VII, VIII and X, can, but need not be, so selected that it corresponds to a complex of formula I. The ratio XII:XIII and other above types, like XII:XIII as per V in mol% of 0.1:99.9 up to 99.9:0.1 is suitable, especially the ratio of 1:99 up to 99.1, particularly that of 1:99 up to 80:20, and more particularly that of 5:95 up to 70:30.

Such a stabiliser mixture can be used as described for the complexes of formula I, particularly in amounts of 0.01–5 percent by weight, relative to the polymer to be stabilised.

the following may be mentioned as examples of further additives together with which the stabilisers and mixtures according to the invention can be used:

1. Antioxidants 1.1. Simple 2,6-dialkylphenols, for example 2,6-ditert.butyl-4-methylphenol, 2-tert.butyl-4,6-dimethylphenol, 2,6-ditert.butyl-4-methoxymethylphenol and 2,6-dioctadecyl-4-methylphenol.

1.2. Derivatives of alkylated hydroquinones, for example 2,5-ditert.butyl-hydroquinone, 2,5-ditert.amyl-hydroquinone, 2,6-ditert.butyl-hydroquinone, 2,5-ditert.butyl-4-hydroxy-anisole, 3,5-ditert.butyl-4-hydroxy-anisole, tris-(3,5-ditert.butyl-4-hydroxyphenyl)-phosphite, 3,5-ditert.butyl-4-hydroxyphenyl-stearate and bis-(3,5-ditert.butyl-4-hydroxyphenyl)-adipate.

1.3. Hydroxylated thiodiphenyl ethers, for example 2,2'-thiobis-(6-tert.butyl-4-methylphenol), 2,2'-thiobis-(4-octylphenol), 4,4'-thiobis-(6-tert.butyl-3-methylphenol), 4,4'-thiobis-(3,6-di-sec.amylphenol), 4,4'-thiobis-(6-tert.butyl-2-methylphenol) and 4,4'-bis(2,6-dimethyl-4-hydroxyphenyl)-disulphide.

1.4. Alkylidene-bisphenols, for example 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-ditert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecyl-mercapto-butane, 1,1,5,5-tetra-(5-tert.butyl-4-hydroxy-2-methylphenyl)-pentane and ethylene-glycol-bis-[3,3-bis-(3'-tert.butyl-4'-hydroxyphenyl)-butyrate].

1.5. O-, N- and S-benzyl compounds, for example 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis(4-tert.butyl-3-hydroxy-2,6-dimethylbenzyl)-dithiol terephthalate.

1.6. Hydroxybenzylated malonic esters, for example 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-ditert.butyl-4-hydroxybenzyl)-malonic acid didodecylmercapto ethylester and 2,2-bis-(3,5-ditert.butyl-4-hydroxybenzyl)-malonic acid di-[4-(1,1,3,3-tetramethylbutyl)-phenyl]-ester.

1.7. Hydroxybenzyl-aromatics, for example 1,3,5-tri-(3,5-ditert.butyl-4-hydroxybenzyl)-2,4,6-trimethylbenzene, 1,4-di-(3,5-ditert.butyl-4-hydroxybenzyl)-2,3,5,6-tetramethylbenzene and 2,4,6-tri-(3,5-ditert.butyl-4-hydroxybenzyl)-phenol.

1.8. s-Triazine compounds, for example 2,4-bis-octylmercapto-6-(3,5-ditert.butyl-4-hydroxyanilino)-s-triazine, 2-octylmercapto-4,6-bis-(3,5-ditert.butyl-4-hydroxyanilino)-s-triazine, 2-octylmercapto-4,6-bis-(3,5-ditert.butyl-4-hydroxyphenoxy)-s-triazine, 2,4,6-tris-(3,5-ditert.butyl-4-hydroxyphenoxy)-s-triazine, 2,4,6-tris-(3,5-ditert.butyl-4-hydroxyphenylethyl)-s-triazine and 1,3,5-tris-(3,5-ditert.butyl-4-hydroxybenzyl)-isocyanurate.

1.9. Amides of β-3,5-ditert.butyl-4-hydroxyphenyl-propionic acid, for example 1,3,5-tris-(3,5-ditert.butyl-4-hydroxyphenyl-propionyl)-hexahydro-s-triazine and N,N'-di-(3,5-ditert.butyl-4-hydroxyphenol-propionyl)-hexamethylenediamine.

1.10. Esters of β- 3,5-ditert.butyl-4-hydroxyphenyl-propionic acid with monohydric or polyhydric alcohols, for example methanol, ethanol, octadecanol; 1,6-hexanediol; 1,9-nonanediol, ethylene glycol; 1,2-propanediol, diethylene glycol, thiodiethylene glycol, neopentyl glycol, 3-thiaundecanol, 3-thiapentadecanol, trimethylhexanediol, trimethylolethane, trimethylolpropane, pentaerylthritol, tris-hydroxyethyl-isocyanurate and 4-hydroxymethyl-1-phospha-2,6,7-trioxabicyclo[2,2,2]octane. 1.11. Esters of β-5-tert.butyl-4-hydroxy-3-methylphenyl-propionic acid with monohydric or polyhydric alcohols, for example methanol, ethanol, octadecanol; 1,6-hexanediol; 1,9-nonanediol, ethylene glycol; 1,2-propanediol, diethylene glycol, thiodiethylene glycol, neopentyl glycol, 3-thiaundecanol, 3-thia-pentadecanol, trimethylhexanediol, trimethylolethane, trimethylolpropane, pentaerythritol, trishydroxyethyl-isocyanurate and 4-hydroxymethyl-1-phospa-2,6,7-trioxa-bicyclo [2,2,2]octane. 1.12. Esters of 3,5-ditert.butyl-4-hydroxyphenylacetic acid with monohydric or polyhydric alcohols, for example methanol, ethanol, octadecanol; 1,6-hexanediol; 1,9-nonanediol, ethylene glycol, 1,2-propanediol; diethylene glycol, thiodiethylene glycol, neopentyl glycol, 3-thiaundecanol, 3-thia-pentadecanol, trimethylhexanediol, trimethylolethane, trimethylolpropane, pentaerylthritol, trishydroxyethylisocyanurate and 4-hydroxymethyl-1-phospha-2,6,7-trioxabicyclo [2,2,2]octane. 1.13. Acylaminophenols, for example N-(3,5-di-tert.butyl-4-hydroxyphenyl)-stearic acid amide and N,N'-di-(3,5-ditert.butyl-4-hydroxyphenyl)-thiobisacetamide.

1.14. Benzylphosphonates, for example 3,5-ditert.butyl-4-hydroxybenzyl-phosphonic acid dimethyl ester, 3,5-di-tert.butyl-4-hydroxybenzyl-phosphonic acid diethyl ester, 3,5-ditert.butyl-4-hydroxybenzyl-phosphonic acid dioatadecyl ester and 5-tert.butyl-4-hydroxy-3-methylbenzyl-phosphonic acid dioctadecyl ester.

1.15 Spiro compounds, for example 3,9-bis-(3,5-ditert.butyl-4-hydroxyphenyl)-2,4,8,10-tetraspiro [5.5]undecane; 3,9-bis-[1,1-dimethyl-2(3,5-di-tert. butyl-4-hyroxyphenyl)-ethyl]-2,4,8,10-tetraoxyspiro [5.5]undecane.

1.16 Aminoaryl derivatives, for example phenyl-1-naphthylamine, phenyl-2-naphthylamine, phenyl-2-napthylamine, N,N'-di-phenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, mono- and dioctyliminodibenzyl, polymerised 2,2,4-trimethyl-1,2-dihydroquinoline, octylated di-phenylamine, nonylated diphenylamine, N-phenyl-N'-isopropyl-p-phenylenediamine, N,N'-di-sec.octyl-p-phenylenediamine, N-phenyl-N'-sec.octyl-p-phenylenediamine, N,N'-dimethyl-(1,4-dimethylpentyl)-p-phenylenediamine, N,N'-dimethyl-N,N'-di-(sec.octyl)-p-phenylenediamine, 2,6-dimethyl-4-methoxyaniline, 4-ethoxy-N-sec.butyl-aniline, diphenylamine-acetone condensation product, aldol-1-naphthylamine, phenothiazine.

2. UV absorbers and light stability agents, for example 2-(2'-hydroxyphenyl)-benztriazoles, 2,4-bis-(2'-hydroxyphenyl)-6-alkyl-s-triazines, 2-hydroxybenzophenones, esters of optionally substituted benzoic acids, acrylates, oxalic acid diamides.

3. Metal deactivators
4. Phosphites
5. Compounds which decompose peroxide
6. Basic co-stabilizers
7. Nucleating agents
8. Other additives, for example lubricants, fillers, carbon black, asbestos, kaolin, talcum, glass fibres, pigments, fluorescent brighteners, flameproofing agents and antistatic agents.

The use of the stabilisers of the formula I or of the mixtures in combination with the antioxidants contained in the above list is effective above all in polyolefins.

The following Examples describe the invention, but do not restrict it to what is described therein.

EXAMPLES 1 to 39

The following general process is suitable for obtaining these compounds. The sterically hindered amines and the metal compound of the formula $Me^{w\oplus}L_w^{\ominus}$ in a solvent which is inert to and sufficiently effective for these components and the end product. If necessary, the mixture is heated until a homogeneous solution is obtained. Thereafter the mixture is refluxed for a short time and the solvent is then evaporated off under a pressure of 11 mm Hg. When choosing the solvent, particular care is to be taken that none of the two components to be dissolved therein crystallises out as sparingly soluble compound during the subsequent evaporation of the solvent mixture and is consequently excluded from the equilibrium of the formation of the ternary complex of the general formula I. The residue is thereafter dried under such conditions that the amine component cannot volatilise.

In Table I, the suitable solvents, the reaction conditions (column 5) and the drying conditions (column 6) are indicated for the Examples defined in columns 1 to 4. Column 7 describes the properties of the end products obtained.

Table 1

| Example | amine component* cf. Table 2) | Me^w+ | H-L= | metal:amine ratio r= | p= | solvent | h | reaction conditions temperature °C | drying temperature/time/pressure (°C. h = hours) (mm Hg) | colour/consistency | solubility** in ethanol | chloroform | toluene | ***ligroin |
|---|---|---|---|---|---|---|---|---|---|---|---|---|---|---|
| 1 | 1 | Ni^+2 | acetylacetone | 1 | 1 | benzene | ½ | rfl. | 50°/16^h/11 | light green | (+) | + | (+) | (+) |
| 2 | 1 | Ni^+2 | acetylacetone | 2 | 1 | benzene | ½ | rfl. | 50°/16^h/11 | light green | + | + | + | (+) |
| 3 | 1 | Co^+2 | acetylacetone | 1 | 1 | benzene | ½ | rfl. | 50°/16^h/11 | pale violet | (+) | + | (+) | (+) |
| 4 | 3 | Ni^+2 | acetylacetone | 1 | 1 | methylene chloride | 2 | 25° C. | 30°/16^h/11 | light green | (+) | + | (+) | (+) |
| 5 | 3 | Ni^+2 | acetylacetone | 1 | 2 | methylene chloride | 2 | 25° C. | 30°/16^h/11 | light green | (+) | + | (+) | (+) |
| 6 | 3 | Co^+2 | acetylacetone | 1 | 1 | methylene chloride | 1 | 25° C. | 30°/16^h/11 | pale violet | + | + | (+) | (+) |
| 7 | 3 | Zn^+2 | acetylacetone | 1 | 1 | ethanol | ½ | rfl. | 50°/16^h/11 | white/wax | + | (+) | (+) | (+) |
| 8 | 4 | Ni^+2 | acetylacetone | 1 | 1 | methanol | ½ | rfl. | 40°/16^h/11 | light green | (+) | + | (+) | (+) |
| 9 | 2 | Ni^+2 | acetylacetone | 1 | 1 | chloroform | ½ | rfl. | 40°/16^h/11 | light green | (+) | + | (+) | (+) |
| 10 | 5 | Ni^+2 | acetylacetone | 1 | 1 | chloroform | ½ | rfl. | 40°/16^h/11 | light green | + | + | + | — |
| 11 | 6 | Ni^+2 | acetylacetone | 1 | 1 | chloroform | ½ | rfl. | 40°/16^h/11 | light green | (+) | + | + | (+) |
| 12 | 7 | Ni^+2 | acetylacetone | 2 | 1 | chloroform | ½ | rfl. | 40°/16^h/11 | light green | + | + | + | (+) |
| 13 | 7 | Ni^+2 | acetylacetone | 1 | 2 | chloroform | ½ | rfl. | 40°/16^h/11 | light green | + | + | +m | (+) |
| 14 | 8 | Ni^+2 | acetylacetone | 1 | 1 | toluene | 1 | 25° C. | 60°/16^h/11 | light green | (+) | + | + | (+) |
| 15 | 3 | Ni^+2 | o-hydroxy-acetophenone | 1 | 1 | benzene | ½ | 25° C. | 50°/16^h/11 | green | + | + | + | — |
| 16 | 2 | Ni^+2 | 2-hydroxy-4-n-oxtoxy-benzophenone | 1 | 1 | benzene | ½ | 25° C. | 50°/16^h/11 | light green | (+) | + | + | (+) |
| 17 | 2 | Ni^+2 | dibenzoyl-methane | 1 | 1 | chloroform | ½ | rfl. | 40°/16^h/11 | yellow | + | + | (+) | — |
| 18 | 3 | Ni^+2 | 2-acetoacetic ester | 1 | 1 | toluene | ½ | rfl. | 60°/16^h/11 | light blue | + | + | (+) | (+) |
| 19 | 3 | Ni^+2 | o-methoxy-octoacetic anilide | 1 | 1 | dioxan | 3½ | rfl. | 60°/16^h/11 | green | (+) | + | (+) | — |
| 20 | 5 | Ni^+2 | o-methoxy-octoacetic anilide | 1 | 1 | dioxan | 1½ | rfl. | 60°/16^h/11 | light green | — | + | (+) | — |
| 21 | 1 | Ni^+2 | enanthic acid | 1 | 1 | toluene | ½ | rfl. | 80°/16^h/11 | yellowish green, wax | — | + | (+) | (+) |
| 22 | 1 | Ni^+2 | lauric acid | 1 | 1 | toluene | ½ | rfl. | 80°/16^h/11 | light green, wax | — | + | (+) | (+) |
| 23 | 1 | Zn^+2 | acetic acid | 1 | 1 | ethanol | ½ | rfl. | 60°/16^h/11 | white | (+) | + | + | — |
| 24 | 1 | Zn^+2 | acetic acid | 2 | 1 | ethanol | ½ | rfl. | 60°/16^h/11 | white | + | + | (+) | — |
| 25 | 1 | Zn^+2 | lauric acid | 1 | 1 | toluene | ½ | rfl. | 80°/16^h/11 | white | (+) | (+) | (+) | (+) |
| 26 | 1 | Zn^+2 | enanthic acid | 1 | 1 | toluene | ½ | rfl. | 80°/16^h/11 | white | (+) | (+) | (+) | (+) |
| 27 | 3 | Ni^+2 | O-ethyl-diethylamino-methane-phosphonic acid | 1 | 1 | toluene | ½ | rfl. | 60°/16^h/11 | brownish beige | + | + | + | — |
| 28 | 3 | Co^+2 | O-ethyl-diethylamino-methane-phosphonic acid | 1 | 1 | benzene | ½ | rfl. | 40°/16^h/11 | violet, wax | + | + | + | + |
| 29 | 1 | Co^+2 | acetylacetone | 2 | 1 | toluene | ½ | rfl. | 60°/16^h/11 | violet | (+) | + | + | (+) |
| 30 | 1 | Mg^+2 | acetylacetone | 2 | 1 | chloroform | ½ | rfl. | 60°/16^h/11 | white | + | + | (+) | — |
| 31 | 1 | Al^+3 | acetylacetone | 2 | 1 | toluene | ½ | rfl. | 60°/16^h/11 | white | + | + | + | (+) |
| 32 | 3 | Ca^+2 | acetylacetone | 1 | 1 | ethanol | ½ | rfl. | 60°/16^h/11 | white, wax | (+) | — | (+) | — |
| 33 | 3 | Mg^+2 | acetylacetone | 1 | 1 | chloroform | ½ | rfl. | 60°/16^h/11 | white | + | + | + | + |
| 34 | 5 | Cr^+3 | acetylacetone | 1 | 1 | toluene | ½ | rfl. | 60°/16^h/11 | violet | + | + | + | (+) |
| 35 | 6 | Co^+2 | acetylacetone | 1 | 1 | toluene | ½ | rfl. | 60°/16^h/11 | violet | (+) | + | (+) | (+) |
| 36 | 9 | Ni^+2 | acetylacetone | 1 | 1 | toluene | 2 | rfl. | 80°/16^h/60 | green | + | + | +, | + |
| 37 | 9 | Mn^+2 | acetylacetone | 1 | 1 | toluene | 2 | rfl. | 80°/16^h/60 | pink | + | + | + | + |
| 38 | 10 | NI^+2 | acetylacetone | 1 | 1 | toluene | 2 | rfl. | 80°/16^h/60 | green | + | + | + | + |
| 39 | 10 | Co^+2 | acetylacetone | 1 | 1 | toluene | 2 | rfl. | 80°/16^h/60 | bluish green | + | + | + | + |
| 40 | 11 | Ni^+2 | acetylacetone | 1 | 1 | toluene | ½ | 25° C. | 50°/16^h/11 | beige | + | + | + | (+) |
| 41 | 1 | Co^+2 | benzoylacetone | 2 | 1 | toluene | ½ | rfl. | 60°/16^h/11 | reddish brown | (+) | (+) | (+) | (+) |
| 42 | 3 | Ni^+2 | benzoylacetone | 1 | 1 | toluene | ½ | rfl. | 60°/16^h/11 | green | + | + | (+) | (+) |

Table 1-continued

| | amine component* cf. Table 2) | $Me^{w\oplus}L_p^\ominus$ | | metal: amine ratio | | reaction conditions | | | drying temperature/ time/ pressure (°C. h = hours) (mm Hg) | properties of the end products | | | | |
|---|---|---|---|---|---|---|---|---|---|---|---|---|---|---|
| | | | | | | | h = hours rfl = reflux | | | | solubility** in | | | |
| Example | | $Me^{w+}$ | H-L= | r= | p= | solvent | h | temperature °C. | | colour/ consistency | ethanol | chloroform | toluene | ***ligroin |
| 43 | 6 | $Ni^{+2}$ | benzoylacetone | 1 | 1 | toluene | ½ | refl. | 60°/16$^h$/11 | green | + | + | + | (+) |
| 44 | 11 | $Ni^{+2}$ | benzoylacetone | 1 | 1 | toluene | ½ | 25° C. | 60°/16$^h$/11 | green | + | (+) | (+) | (+) |
| 45 | 3 | $Ni^{+2}$ | 3-methyl-pentanedione-2.4 | 1 | 1 | toluene ethanol 1:1 | ½ | rfl. | 60°/16$^h$/11 | olive green | + | − | + | − |
| 46 | 12 | $Ni^{+2}$ | acetylacetone | 1 | 1 | methylene-chloride | 2 | 25° C. | 25°/16$^h$/11 | light green | (+) | + | + | (+) |
| 47 | 3 | $Ni^{+2}$ | ethylacetate | 1 | 1 | methyl-cello-solve | 1½ | rfl. | 60°/16$^h$/11 | dark green, wax | + | + | + | (+) |
| 48 | 6 | $Ni^{+2}$ | acetoacetic acid | 1 | 1 | methylene chloride | ½ | rfl. | 40°/16$^h$/11 | light green, wax | (+) | + | + | + |
| 49 | 5 | $Ni^{+2}$ | tenoyltri-fluoroacetone | 1 | 1 | ethylene-glycol dimethyl ether | ½ | rfl. | 60°/16$^h$/11 | green | + | + | + | (+) |
| 50 | 5 | $Ni^{+2}$ | 1-phenyl-3-methyl-4-nonylcarbonyl-pyrazolone-5 | 1 | 1 | chloroform | ½ | rfl. | 60°/16$^h$/11 | light green | (+) | + | (+) | (+) |
| 51 | 3 | $Ni^{+2}$ | 1-phenyl-3-methyl-4-nonylcarbonyl-pyrazolone-5 | 1 | 1 | toluene | ½ | rfl. | 60°/16$^h$/11 | light green | (+) | (+) | (+) | (+) |
| 52 | 1 | $Ni^{+2}$ | o-methoxy-acetoacetic anilide | 1 | 1 | dioxan | 1 | rfl. | 60°/16$^h$/11 | green | (+) | + | (+) | − |
| 53 | 6 | $Ni^{+2}$ | N-(n-butyl)salicylald-imine | 1 | 1 | toluene | ½ | rfl. | 80°/16$^h$/11 | green | + | + | + | + |
| 54 | 5 | $Ni^{+2}$ | N-methylaceto-phenonimine | 1 | 1 | chloroform | ½ | rfl. | 60°/16$^h$/11 | greyish beige | (+) | (+) | (+) | (+) |
| 55 | 3 | $Ni^{+2}$ | N-methylaceto-phenonimine | 1 | 1 | chloroform | ½ | rfl. | 60°/16$^h$/11 | brown | (+) | (+) | (+) | (+) |
| 56 | 5 | $Ni^{+2}$ | bis-acetyl-acetone.ethylenedi-imine | 1 | 1 | toluene | ½ | rfl. | 60°/16$^h$/11 | brownish beige | + | + | + | (+) |
| 57 | 5 | $Ni^{+2}$ | O-ethyl-a-ethyl-hexyl-benzylphos-phonic acid | 1 | 1 | benzene | ½ | rfl. | 50°/16$^h$/11 | light green | + | + | + | + |
| 58 | 3 | $Ni^{+2}$ | N,N-diethyl-aminomethyl-phenylphos-phonic acid | 1 | 1 | toluene | ½ | rfl. | 60°/16$^h$11 | light yellow | (+) | + | + | − |
| The following compounds were prepared for the comparison with the prior art | | | | | | | | | | | | | | |
| A | 3 | $Ni^{+2}$ | 2,2'-thio-bis(4-di-tert.octyl)-phenol | 1 | 1 | benzene | ½ | rfl. | 60°/16$^h$/11 | light green, wax | (+) | + | + | + |
| B | 2 | $Ni^{+2}$ | O-ethyl-4-hydroxy-3,5-di-tert.butyl-benzyl-phosphoric acid | 1 | 1 | benzene | ½ | rfl. | 40°/16$^h$/11 | greenish beige | + | + | + | (+) |
| C | 1 | $Ni^{+2}$ | 2,2'-thio-bis-(4-di-tert.octyl)phenol | 2 | 1 | toluene | ½ | rfl. | 80°/16$^h$/11 | green, resin | + | + | + | + |
| D | 1 | $Ni^{+2}$ | O-ethyl-4-hydroxy-3,5-di-tert.butyl-benzylphosphos- | 2 | 1 | toluene | ¾ | rfl. | 80°/16$^h$/11 | beige | (+) | + | + | − |

Table 1-continued

| Example | amine component* cf. Table 2) | Me^w⊕L_w⊖ Me^w+ | H-L= phonic acid | metal: amine ratio r= | p= | solvent | reaction conditions h = hours rfl = reflux tempe- rature h °C. | drying temperature/ time/ pressure (°C. h = hours) (mm Hg) | properties of the end products colour/ consistency | solubility** in ethanol | chloroform | toluene | ***ligroin |
|---|---|---|---|---|---|---|---|---|---|---|---|---|---|

*The amine components are here designated by the numbers 1 to 8. The meaning of these abbreviatons follows from Table 2.
**The columns headed "solubility" denote the solubility of the end product in the cited solvents, the plus and minus signs meaning:
+the substance passes into solution at room temperature
(+)the substance only passes into solution when heat is applied
−the substance is not noticeably soluble
***"ligroin" = petroleum fraction which boils at 110°-140° C.

The nickel complex of o-methoxy-acetoacetic anilide required for obtaining the compounds of Examples 19, 20 and 53 can be prepared in analogous manner to the nickel-II-β-ketoamine complexes, see Inorg. Synthesis vol. 11, page 72, Table 2

| amine compound in Table 1 | name of the amine components |
|---|---|
| 1 | bis-(2,2,6,6-tetramethyl-4-piperidyl)-sebacate |
| 2 | 2,2,6,6-tetramethyl-4-benzoyloxy-piperidine |
| 3 | 2,2,6,6-tetramethyl-4-stearoyloxy-piperidine |
| 4 | 1,2,2,6,6-pentamethyl-4-stearoyloxy-piperidine |
| 5 | 2,2,6,6-tetramethyl-4-benzamido-piperidine |
| 6 | 1,3,8-triaza-3n-octyl-7,7,9,9-tetramethyl-spiro[4.5]decane-2,4-dione |
| 7 | 2,2,6,6-tetramethylpiperidine-4-spiro-2'-(1',3'-dioxane)-5'-spiro-5''-(1'',3''-dioxane)-2''-spiro-4'''-(2''',2''',6''',6'''-tetramethyl-piperidine) |
| 8 | 8-aza-2-hydroxymethyl-7,7,9,9,-tetramethyl-1,4-dioxa-spiro[4.5]decane |
| 9 | bis-(3,5-di-tert.butyl-4-hydroxybenzyl)-malonic-acid-bis(2,2,6,6-tetramethyl-4-piperidinyl)-ester |
| 10 | n-butyl-(3,5-di-tert.butyl-4-hydroxybenzyl)-malonic acid-bis(1,2,2,6,6-pentamethyl-4-piperidinyl)-ester |
| 11 | 2,2,6,6-tetramethyl-4-benzoyloxypiperidine-1-oxyl |
| 12 | 1-thia-3,3,5,5-tetramethyl-4-aza-cyclohexane-1,1-dioxide |

EXAMPLE 59

1000 parts of polypropylene powder (melt index 1.5 g/ 10 minutes at 230° C., 2160 g are mixed in a drum mixer with 1 part of pentaerylthritol-tetrakis-[3-(3'5'-di-tert.butyl-4-hydroxyphenyl)-propionate]and 2.5 parts of a nickel compound of Table IV and subsequently granulated in an extruder at a temperature of 200°-220° C. The resultant granules are processed to a sheet in the conventional manner using an extruder with slot die. This sheet is cut into ribbons which are then stretched to 6 times their length at elevated temperature and wound on a spool. The titre of the ribbons is 900-1000 den., and their ultimate tensile strength is 5.5-6.5 g/den.

These polypropylene ribbons are applied without tension to test carriers and exposed in a xenotest apparatus 150. Five test specimens are taken after different times and their ultimate tensile determined. Criterion for the protective action of the individual nickel compounds is the "protective factor", which is defined as follows:

$$\text{"protective factor"} = \frac{\text{exposure time of the light stabilised sample up to 50\% loss of ultimate tensile strength}}{\text{exposure time of the unstabilised sample up to 50\% loss of ultimate tensile strength}}$$

The values obtained are given in the following Tables III and IV:

Table III

| light stability agent compound of Example No. | exposure time in hours to 50% less of ultimate tensile strength | "protective factor" |
|---|---|---|
| no light stability agent | 150 | 1 |
| agent A | 550 | 4 |
| agent B | 460 | 3 |
| 1 | 3200 | 21 |
| 2 | 2800 | 19 |
| 3 | 2550 | 17 |
| 4 | 2200 | 15 |
| 5 | 2750 | 18 |
| 6 | 2200 | 15 |
| 8 | 2300 | 15 |
| 9 | 2100 | 14 |
| 10 | 1800 | 12 |
| 11 | 2200 | 15 |
| 12 | 2600 | 17 |
| 13 | 2300 | 15 |
| 14 | 1600 | 11 |
| 15 | 1600 | 11 |
| 16 | 1550 | 10 |
| 18 | 2600 | 17 |
| 21 | 1400 | 9 |
| 26 | 1600 | 11 |
| 28 | 1950 | 13 |
| 32 | 1800 | 12 |
| 33 | 2550 | 17 |
| 35 | 2450 | 16 |
| 36 | 2550 | 17 |
| 38 | 3100 | 21 |
| 40 | 1950 | 13 |
| 42 | 3200 | 21 |
| 43 | 2350 | 16 |
| 47 | 2400 | 16 |
| 53 | 3100 | 21 |

Table IV

| light stability agent compound of Example No. | exposure time in hours to 50% less of ultimate tensile strength | "protective factor" |
|---|---|---|
| no light stability agent | 220 | 1 |
| compound C | 970 | 4.5 |
| compound D | 980 | 4.5 |
| 29 | 2000 | 9 |

Table IV-continued

| light stability agent compound of Example No. | exposure time in hours to 50% less of ultimate tensile strength | "protective factor" |
|---|---|---|
| 30 | 2000 | 9 |
| 37 | 2050 | 9 |
| 44 | 1900 | 9 |
| 52 | 1740 | 8 |

EXAMPLE 60

1000 parts of polypropylene powder (melt index 2.5 g/ 10 minutes at 230° C., 2160 g) are mixed in a drum mixer with 1 part of pentaerythritol-tetrakis-[3-(3',5'-di-tert.butyl-4-hydroxyphenyl)-propionate] and 1.5 parts of a mixture of components I and II of Table V and subsequently granulated in an extruder at a temperature of 200°–220° C. The resultant granules are processed to a sheet in the conventional manner using an extruder with slot die. This sheet is cut into ribbons which are then stretched to 6 times their length at elevated temperature and wound on a spool. The titre of the ribbons is 900–1000 den., and their ultimate tensile strength is 5.5–6.5 g/den.

These polypropylene ribbons are applied without tension to test carriers and exposed in a xenotes apparatus 1200. Five test specimens are taken after different times and their ultimate tensile determined. Criterion for the protective action of the individual nickel compounds is the "protective factor", which is defined as follows:

$$\text{"protective factor"} = \frac{\text{exposure time of the light stabilised sample up to 50\% loss of ultimate tensile strength}}{\text{exposure time of the unstabilised sample up to 50\% loss of ultimate tensile strength}}$$

The values obtained are listed in the following Table V:

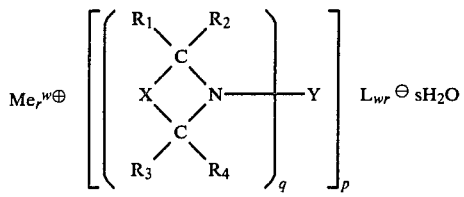

(I)

wherein
Me is a doubly or triply positively charged metal ion,
w is 2 or 3,
p is 1 or 2,
q is 1 or 2,
r is equal to the number, to half the number or to a quarter of the number of the $>$N-Y groups present within the bracket q,
$R_1$, $R_2$, $R_3$ and $R_4$ independently of one another are alkyl, or
$R_1$ and $R_3$ together are alkylene, or
$R_1$ and $R_2$ or $R_3$ and $R_4$, independently of one another, together are alkylene or azaalkylene,
and, if q is 1,
Y is hydrogen, oxyl, optionally substituted alkyl, alkenyl, alkynyl or aralkyl,
or, if q is 2,
Y is alkylene, alkenylene, alkynylene or arylene-dialkylene,
s is a value from 0 to 2,
X is a divalent organic radical which supplements the N-containing ring to form a piperidine ring, and
L is a singly charged anion of an enol of formula II

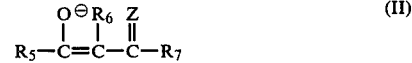

(II)

wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxy- Table V

| component I amine component of Table II | component II $Me^{w+}L_w^-$ | | molar ratio of components I:II | exposure time in hours up to 50% less of ultimte tensile strength | "protective factor" |
|---|---|---|---|---|---|
| | $Me^{w+}$ | HL = | | | |
| none | | no stabiliser | — | 150 | 1 |
| 3 | $Ni^{+2}$ | 2,2'-thio-bis-(4-di-tert.octyl)-phenol | 1:1 | 550 | 4 |
| 1 | $Ni^{+2}$ | acetylacetone | 1:1 | 3200 | 21 |
| 1 | $Co^{+2}$ | acetylacetone | 1:1 | 2200 | 15 |
| 2 | $Ni^{+2}$ | acetylacetone | 1:1 | 2000 | 13 |
| 2 | $Ni^{+2}$ | 2-hydroxy-4-n-octoxy-benzophenone | 1:1 | 1850 | 12 |
| 3 | $Ni^{+2}$ | acetylacetone | 1:1 | 2500 | 17 |
| 3 | $Ni^{+2}$ | acetylacetone | 1:2 | 2400 | 16 |
| 3 | $Co^{+2}$ | acetylacetone | 1:1 | 2100 | 14 |
| 5 | $Ni^{+2}$ | acetylacetone | 1:1 | 1550 | 10 |
| 6 | $Ni^{+2}$ | acetylacetone | 1:1 | 2300 | 15 |
| 11 | $Ni^{+2}$ | acetylacetone | 1:1 | 1950 | 13 | carbonyl, or $R_5$ and $R_6$ together are optionally substituted 1,4-butadi-1,3-enylene or 1,4-butylene, and $R_7$ is optionally substituted alkyl, alkenyl, cycloalkyl, aralkyl, aryl, alkoxy or optionally substituted amino.

We claim:
1. Metal complex of formula I

2. Metal complex of formula I

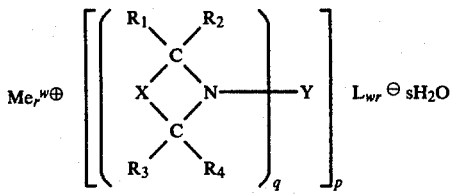

wherein
Me is a doubly or triply positively charged metal ion,
w is 2 or 3,
p is 1 or 2,
q is 1 or 2,
r is equal to the number, to half the number or to a quarter of the number of the >N-Y groups present within the bracket q,
$R_1$, $R_2$, $R_3$ and $R_4$ independently of one another are alkyl, or
$R_1$ and $R_2$ or $R_3$ and $R_4$, independently of one another, together are alkylene,
and, if q is 1,
Y is hydrogen, oxyl, optionally substituted alkyl, alkenyl, alkynyl or aralkyl,
or, if q is 2,
Y is alkylene, alkenylene, alkynylene or arylene-dialkylene,
s is a value from 0 to 2,
X is a divalent organic radical which supplements the N-containing ring to form a piperidine ring, and
L is a singly charged anion of an enol of formula II

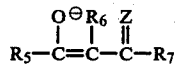

4. Metal complex according to claim 3, wherein r is equal to the number of the >N-Y groups in the bracket q.

5. Metal complex according to claim 3, characterised in that the enol is an enol of formula II, wherein Z is an alkylimino substituted by $-N=C(R_7)-C(R_6)=C(O^\ominus)R_5$, wherein $R_5$, $R_6$ and $R_7$ have the meaning in claim 3, or Z is hydroxyimino, alkoxyimino, alkylimino, cycloalkylimino, aralkylimino or arylimino.

6. Metal complex according to claim 3, characterised in that the enol is an enol of formula II, wherein Z is oxo or imino, $R_5$ is $C_1-C_{12}$-alkyl, $R_6$ is hydrogen, or $R_5$ and $R_6$ together are 1,4-butadi-1,3-enylene optionally substituted by $C_1-C_{12}$-alkyl, $C_1-C_{12}$-alkoxy or halogen, and $R_7$ is $C_1-C_{12}$-alkoxy.

7. Metal complex according to claim 6, characterised in that the enol of formula II is the enolate ion of acetylacetonate.

8. Metal complex according to claim 7, wherein r is equal to the number of the >N-Y groups in the bracket q.

9. Metal complex according to claim 6, wherein r is equal to the number of the >N-Y groups in the bracket q.

10. Metal complex according to claim 3, characterised in that the enol is an enol of formula II, wherein Z is oxo or imino, $R_5$ is $C_1-C_{12}$-alkyl, $R_6$ is hydrogen, or $R_5$ and $R_6$ together are 1,4-butadi-1,3-enylene optionally substituted by $C_1-C_{12}$-alkyl, $C_1-C_{12}$-alkoxy or halogen, and $R_7$ is $C_1-C_{12}$-alkyl or phenyl.

11. Metal complex according to claim 6, characterised in that z is oxo.

12. Metal complex according to claim 11, wherein r is equal to the number of the >N-Y groups in the bracket q.

13. Metal complex according to claim 2 of formula III

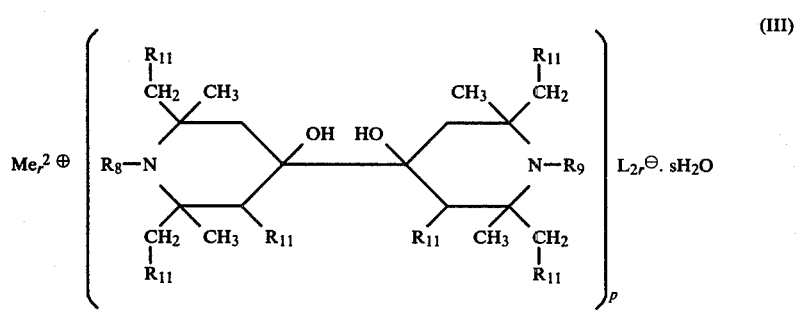

wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxycarbonyl, or $R_5$ and $R_6$ together are optionally substituted 1,4-butadi-1,3-enylene or 1,4-butylene, and $R_7$ is optionally substituted alkyl, alkenyl, cycloalkyl, aralkyl, aryl, alkoxy or optionally substituted amino.

3. Metal complex according to claim 2, characterised in that the enol is that of formula II, wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxycarbonyl, or $R_5$ and $R_6$ together are optionally substituted 1,4-butadi-1,3-enylene or 1,4-butylene, and $R_7$ is optionally substituted alkyl, alkenyl, cycloalkyl, arylkyl, aryl or alkoxy.

wherein Me, p, r, s and L have the meanings given in claim 2, $R_8$ and $R_9$ independently of one another are hydrogen, alkyl, alkenyl, alkynyl, aralkyl, hydroxyalkyl, alkoxyalkyl, aliphatic or aromatic acyloxyalkyl, cyanoalkyl, halogenoalkyl, epoxyalkyl or alkoxycarbonylalkyl, and $R_{11}$ is hydrogen or methyl.

14. Metal complex according to claim 13, wherein r is equal to the number of the >N-Y groups in the bracket q.

15. Metal complex according to claim 2, of formula IV

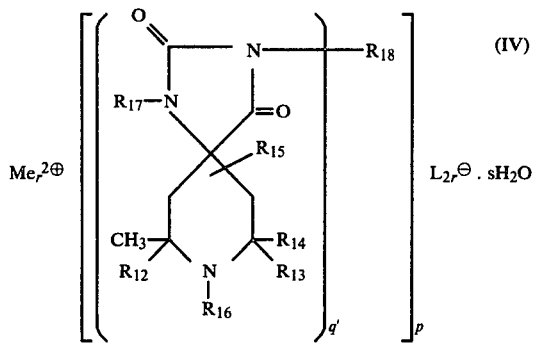

wherein Me, p, r, s and L have the meanings given in claim 2, q' is 1 or 2, $R_{12}$ is alkyl, $R_{13}$ is alkyl, $R_{14}$ is alkyl, phenyl or aralkyl, or $R_{13}$ and $R_{14}$ together are alkylene, $R_{15}$ is hydrogen, alkyl or allyl, $R_{16}$ is hydrogen, oxyl, alkyl, alkenyl, aralkyl, epoxyalkyl, 2-hydroxyethyl, 2-alkoxyethyl, 2-aryloxyethyl, 2-aralkoxyethyl or 2-acyloxyethyl, $R_{17}$ is hydrogen, alkyl or alkenyl, and $R_{18}$, where q' equals 1, is hydrogen, alkyl, alkenyl, aralkyl, aryl, cycloalkyl, epoxyalkyl, alkoxyalkyl, phenoxyalkyl, alkoxycarbonylmethyl, phenoxycarbonylmethyl, hydroxyalkyl, acyloxyalkyl, 2-hydroxyphenethyl, 2-alkoxyphenethyl, 2-aryloxyphenethyl, 2-aralkoxyphenethyl or 2-acyloxyphenethyl, or $R_{18}$, where q' equals 2, is alkylene, oxaalkylene, alkenylene, arylene-dialkylene, arylene, oxy-diphenylene, methylene-diphenylene, alkylene-di-(oxycarbonylalkylene), alkylene-di-(carbonyloxyalkylene), alkylene-di-(carbonyloxyaralkylene), thiaalkylene-di-(carbonyloxyalkylene), thiaalkylene-di-(carbonyloxyaralkylene), alkenylene-di-(carbonyloxyalkylene), alkenylene-di-(carbonyloxyaralkylene), phenylene-di-(carbonyloxyalkylene), phenylene-di-(carbonyoxyaralkylene), 1,4-cyclohexylene-di-(carbonyloxyalkylene) or 1,4-cyclohexylene-di-(carbonyloxyaralkylene).

16. Metal complex according to claim 15, wherein r is equal to the number of the >N-Y groups in the bracket q.

17. Metal complex according to claim 2, of formula VI

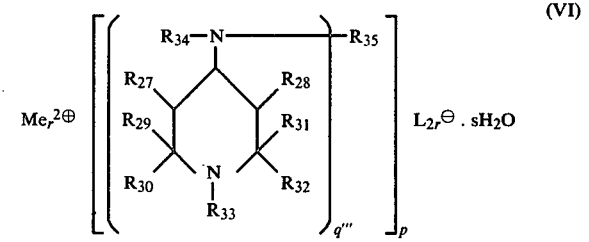

wherein Me, p, r, s and L have the meanings given in claim 2, and wherein the other symbols have the following meanings: $R_{27}$ and $R_{28}$ are, independently of one another, hydrogen, alkyl, alkenyl, alkynyl or aralkyl, $R_{29}$ and $R_{30}$ independently of one another are alkyl, $R_{31}$ is alkyl, $R_{32}$ is alkyl, or $R_{31}$ and $R_{32}$ together are tetramethylene or pentamethylene, $R_{33}$ is hydrogen, oxyl, alkyl, alkenyl, alkoxyalkyl, aralkyl, 2,3-epoxypropyl, alkoxycarbonylmethyl, alkenyloxycarbonylmethyl, phenoxycarbonylmethyl, aralkoxycarbonylmethyl, cyclohexyloxycarbonylmethyl, 2-hydroxyethyl, 2-hyroxypropyl, 2-phenyl-2-hydroxyethyl, 2-acyloxyethyl, 2-acyloxypropyl or 2-phenyl-2-acyloxy-ethyl, $R_{34}$ is hydrogen, alkyl, cycloalkyl or aralkyl, q''' is 1, 2 or 3, and $R_{35}$ where q''' is equal to 1 is alkanoyl, alkenoyl, alkoxycarbonyl, benzyloxycarbonyl, cycloalkoxycarbonyl, arylcarbonyl, styrylcarbonyl, aralkylcarbonyl, heterocyclylcarbonyl, optionally substituted carbamoyl, alkylsulphonyl, arylsulphonyl, —P(alkoxy)$_2$, —P(aryloxy)$_2$, —P(alkyl)$_2$, —P(aryl)$_2$, —P(aralkyl)$_2$, —P(cyclohexyl)$_2$, —P(O or S)(alkoxy)$_2$, —P(O or S)(aryloxy)$_2$, —P(O or S)(alkyl)$_2$, —P(O or S)(aryl)$_2$, —P(O or S)(aralkyl)$_2$, —P(O or S))cyclohexyl)$_2$, or $R_{35}$ and $R_{34}$ together with the N atom binding them are succinimido, malonimido or phthalimido; and $R_{35}$ where q''' is equal to 2 is carbonyl, oxalyl, alkylenedicarbonyl, thiaalkylenedicarbonyl, alkenylenedicarbonyl, arylenedicarbonyl, cyclohexylenedicarbonyl, alkylene-di-aminocarbonyl, arylene-di-aminocarbonyl, cyclohexylene-di-aminocarbonyl, >P(alkoxy), >P(aryloxy), >P(alkyl), >P(aryl), >P(aralkyl), >P(cyclohexyl) >P(O or S)(alkyl), >P(O or S)(aralkyl) or >P(O or S) (cyclohexyl); and $R_{35}$ where q''' is equal to 3 is benzenetricarbonyl, s-triazine-2,4,6-triyl, $\equiv$P, $\equiv$PO or $\equiv$PS.

18. Metal complex according to claim 17, wherein r is equal to the number of the >N-Y groups in the bracket q.

19. Metal complex according to claim 2, of formula VIII

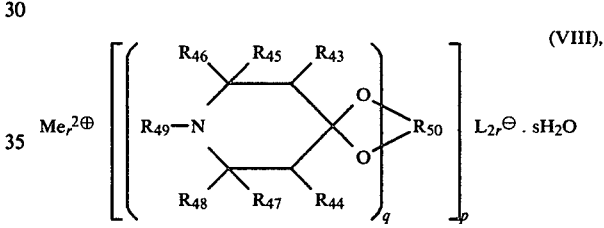

wherein Me, p, q, r, s and L have the meanings given in claim 2 and the other symbols have the following meanings: $R_{43}$ and $R_{44}$ independently of one another are hydrogen, alkyl, alkenyl, alkynyl or aralkyl, $R_{45}$ and $R_{46}$ each independently represent alkyl, $R_{47}$ is alkyl, $R_{48}$ is alkyl, or $R_{47}$ and $R_{48}$ together are tetramethylene or pentamethylene, $R_{49}$ is hydrogen, oxyl, alkyl, alkenyl, alkynyl, alkoxyalkyl, aralkyl, 2,3-epoxypropyl,alkoxycarbonylmethyl, alkenyloxycarbonylmethyl, phenoxycarbonylmethyl, aralkoxycarbonylmethyl, cyclohexyloxycarbonylmethyl, 2-hydroxyethyl, 2-hydroxypropyl, 2-phenyl-2-hydroxy-ethyl, 2-acyloxyethyl, 2-acyloxypropyl or 2-phenyl-2-acyloxyethyl, and $R_{50}$, if q is 1, is optionally substituted ethylene, o-phenylene, optionally substituted 1,3-propylene, and $R_{50}$, if q is 2, is

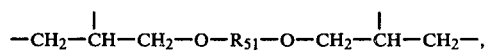

(—CH$_2$)$_2$C(CH$_2$—)$_2$, (—CH$_2$)$_2$CR$_{55}$—CH$_2$—O—R$_{51}$—O—CH$_2$—CR$_{53}$(CH$_2$—)$_2$, wherein $R_{51}$ is a divalent acyl radical, and $R_{53}$ is hydrogen, methyl or ethyl.

20. Metal complex according to claim 19, wherein r is equal to the number of the >N-Y groups in the bracket q.

21. Metal complex according to claim 2, of formula X

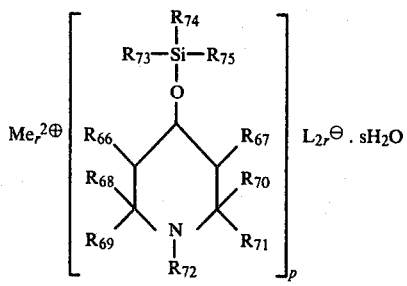

wherein Me, p, r, s and L have the meanings given in claim 2, and the meanings of the other symbols are as follows: $R_{66}$ and $R_{67}$ independently of one another are hydrogen, alkyl, alkenyl, alkynyl or aralkyl, $R_{68}$, $R_{69}$ and $R_{70}$ independently of one another are alkyl, $R_{71}$ is alkyl, or $R_{70}$ and $R_{71}$ together are tetramethylene or pentamethylene, $R_{72}$ is hydrogen, oxyl, alkyl, alkenyl, alkoxyalkyl, aralkyl, alkoxycarbonylmethyl, alkenyloxycarbonylmethyl, phenoxycarbonylmethyl, aralkoxycarbonylmethyl, cyclohexyloxycarbonylmethyl, or $-CH_2-CH(R_{76})OR_{77}$, wherein $R_{76}$ is hydrogen, methyl or phenyl, and $R_{77}$ is hydrogen or acyl, $R_{73}$ is hydrogen, methyl, phenyl, or vinyl, $R_{74}$ and $R_{75}$ independently of one another are hydrogen, methyl, phenyl, vinyl, alkoxy, alkoxyalkoxy, cyclohexyloxy, aralkoxy, aryloxy, 1-$R_{72}$-2-$R_{68}$-2-$R_{69}$-3-$R_{66}$-5-$R_{67}$-6-$R_{70}$-6-$R_{71}$-4-piperidyloxy, or, if $R_{73}$ and $R_{74}$ are hydrogen, methyl, phenyl or vinyl, $R_{75}$ can be a radical of formula XI

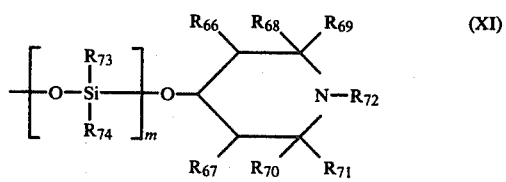

wherein m is an integer from 1–10.

22. Metal complex according to claim 21, wherein r is equal to the number of the >N-Y groups in the bracket q.

23. Metal complex according to claim 2, wherein w is 2, and Me is manganese, zinc, cobalt or nickel; or w is 3 and Me is aluminium.

24. Metal complex according to claim 2, wherein w is 2 and Me is nickel.

25. Metal complex according to claim 24, wherein r is equal to the number of the >N-Y groups in the bracket q.

26. Metal complex according to claim 2, wherein r is 1 or 2.

27. Metal complex according to claim 2, (3-n-octyl-7,7,9,9-tetramethyl-1,3,8-triazaspiro[4.5]decane-2,4-dione)-nickel-di-acetylacetonate.

28. Metal complex according to claim 2, [2,2,6,6-tetramethylpiperidine-4-spiro-2'-(1',3'-dioxane)-5'-spiro-5''-(1'',3''-dioxane)-2''-spiro-4'''-(2''',2''',6''',6'''-tetramethylpiperidine]-di-(nickel-di-acetylacetonate).

29. Metal complex according to claim 2, (8-aza-2-hydroxymethyl-7,7,9,9,-tetramethyl-1,4-dioxaspiro[4.5-]decane)-nickel-di-acetylacetonate.

30. Metal complex according to claim 2, (8-aza-7,9-diethyl-6,7,9-trimethyl-1,4-dioxa-spiro[4.5]decane)-Ni-di-ethylacetylacetate.

31. Metal complex according to claim 2, (2,2,6,6-tetramethyl-4-triphenylsiloxypiperidine)-(1,3-di-phenylpropanedione(1,3)ato)-Ni.

32. Metal complex according to claim 2, [diphenylbis-(2,2,6,6-tetramethyl-piperidine-4-oxy)-silane]-di-(Co(II)-di-acetylacetonate.

33. Metal complex according to claim 2, wherein w is 2 and Me is magnesium, calcium, strontium, barium, cadmium, vanadyl, manganese, zinc, cobalt or nickel, or w is 3 and Me is chromium or aluminium.

34. Stabilizer mixture comprising a compound of formula XII and a compound of formula XIII

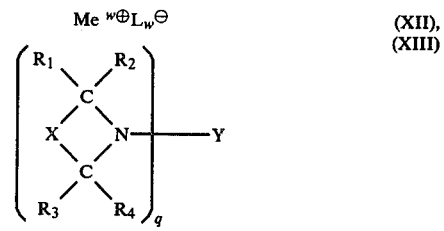

wherein Me, L, w, X, $R_1$, $R_2$, $R_3$, $R_4$, Y and q are as defined in claim 2.

35. Stabiliser mixture according to claim 34, characterised in that the ratio of the compounds of the formulae XII and XIII in mol-% is from 0.1:99.9 up to 99.9:0.1.

36. Stabiliser mixture according to claim 35, characterised in that the ratio of the compounds of the formulae XII and XIII in mol-% is from 1:99 up to 99:1.

37. Stabiliser mixture according to claim 36, characterised in that the ratio of the compounds of the formulae XII and XIII in mol-% is from 1:99 up to 80:20.

38. A process for stabilizing organic polymers against light induced degradation comprising incorporating into said polymers 0.01 to 5% by weight of a stabilizer mixture of claim 34.

39. A metal complex of formula V

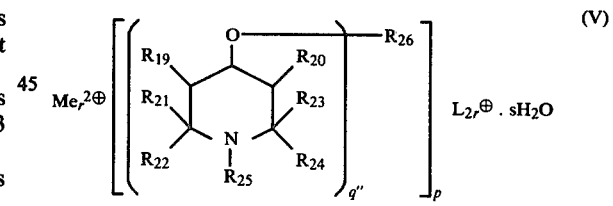

wherein Me is a doubly positively charged metal ion, is 1 or 2, r is equal to the number, to half the number or a quarter of the number of the >N-$R_{25}$ groups present within the parenthesis q'', s is 0 to 2

$R_{19}$ and $R_{20}$ independently of one another are hydrogen, alkyl, alkenyl, alkynyl or aralkyl, $R_{21}$ and $R_{22}$ independently of one another are alkyl, $R_{23}$ is alkyl, $R_{24}$ is alkyl, phenyl or aralkyl or $R_{23}$ and $R_{24}$ together are alkylene, $R_{25}$ is hydrogen, oxyl, alkyl, alkenyl, alkoxyalkyl, aralkyl, epoxyalkyl, alkoxycarbonylmethyl, alkenyloxycarbonylmethyl, phenoxycarbonylmethyl, aralkoxycarbonylmethyl, cycloalkyloxycarbonylmethyl, hydroxyalkyl or acyloxyalkyl, q'' is 1, 2, 3 or 4, $R_{26}$ is hydrogen, a mono- to trivalent, optionally substituted hydrocarbon radical or a mono- to quadrivalent radical derived from an organic or inorganic acid by the splitting-off of at least one hydroxyl group and L is a singly charged enol anion of formula (II)

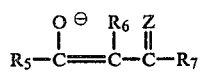

wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxycarbonyl, or $R_5$ and $R_6$ together are optionally substituted 1,4-butadi-1,3-enylene or 1,4-butylene, and $R_7$ is optionally substituted alkyl, alkenyl, cycloalkyl, aralkyl, aryl, alkoxy or optionally substituted amino.

40. Metal complex according to claim 39, (2,2,6,6-tetramethyl-4-stearoyloxy-piperidine)-nickel-di-acetylacetonate.

41. Metal complex according to claim 39, (2,2,6,6-tetramethyl-4-benzoyloxy-piperidine)-nickel-di-acetylacetonate.

42. Metal complex according to claim 39, (1,2,2,6,6-pentamethyl-4-stearoyloxy-piperidine)-nickel-di-acetylacetonate.

43. Metal complex according to claim 39, (2,2,6,6-tetramethyl-4-benzoylamido-piperidine)-nickel-di-acetylacetonate.

44. Metal complex according to claim 39, (2,3,6-trimethyl-2,6-diethyl-4-benzoylamidopiperidine)-nickel-di-acetylacetonate.

45. Metal complex according to claim 39, (2,2,6,6-tetramethyl-4-acetamidopiperidine)-nickel-di-benzoylacetonate.

46. Metal complex according to claim 39, (2,6-diethyl-2,3,6-trimethyl-4-acetamidopiperidine)-Co(II)-di-acetylacetonate.

47. Metal complex according to claim 39, (2,6-diethyl-2,3,6-trimethyl-4-benzoyloxypiperidine)-Ni-di-2-acetyl-phenolate.

48. Metal complex according to claim 39, (2,2,6,6-tetramethyl-4-benzoyloxypiperidine-1-oxyl)-Ni-di-acetylacetonate.

49. Metal complex according to claim 39, (2,2,2′,2′,6,6,6′,6′-octamethyl-4,4′-dihydroxy-4,4′-bipiperidine)-di-(Ni-di-acetylacetonate.

50. Metal complex according to claim 39, [N,N′-bis-(2,2,6,6-tetramethyl-4-piperidinyl)-oxalamide]-di-(Ni-di-benzoylacetylacetate.

51. Metal complex according to claim 39, (2,2,6,6-tetramethyl-4-benzamidopiperidine)-Ni-di-(2-benzoyl-5-n-octoxyphenolate).

52. Metal complex according to claim 39, (2,2,6,6-tetramethyl-4-stearoyloxypiperidine)-Ca-di-acetylacetonate.

53. Metal complex according to claim 39, wherein r is equal to the number of the >N-Y groups in the bracket q.

54. A process for stabilizing organic polymers against light induced degradation comprising incorporating into said polymers 0.01 to 5% by weight of a metal complex of claim 39.

55. Stabilizer mixtue composed of a compound of formula XII and a compound of formula V′

$$Me^{w\oplus}L_w^{\ominus} \qquad (XII)$$

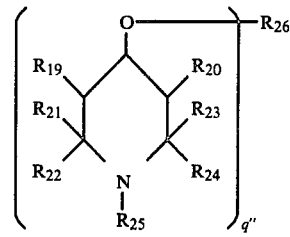

wherein Me, L, $R_{19}$, $R_{20}$, $R_{21}$, $R_{22}$, $R_{23}$, $R_{24}$, $R_{25}$, $R_{26}$ and q″ are as defined in claim 11, and w is 2 or 3.

56. Metal complex of formula VII

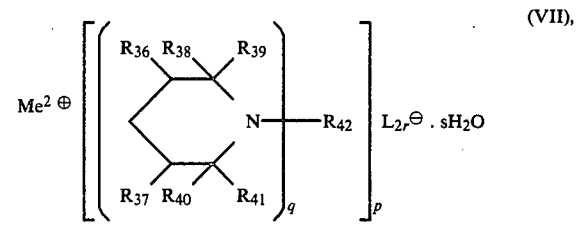

wherein
Me is a doubly positively charged metal ion,
p is 1 or 2,
q is 1 or 2,
r is equal to the number, to half the number or to a quarter of the number of the >N-Y groups present within the bracket q,
$R_{36}$ and $R_{37}$ independently of one another are hydrogen, alkyl, alkenyl, alkynyl or aralkyl,
$R_{38}$, $R_{39}$, $R_{40}$ and $R_{41}$ independently of one another are alkyl, or $R_{40}$ and $R_{41}$ together are tetramethylene or pentamethylene,
and, where q is 1,
$R_{42}$ is hydrogen, oxyl, alkyl, alkenyl, alkynyl, alkoxyalkyl, aralkyl, 2,3-epoxypropyl, alkoxycarbonylmethyl, alkenyloxycarbonylmethyl, phenoxycarbonylmethyl, aralkoxycarbonylmethyl, cyclohexyloxycarbonylmethyl, 2-hydroxyethyl, 2-hydroxypropyl, 2-phenyl-2-hydroxy-ethyl, 2-acyloxyethyl, 2-acyloxypropyl or 2-phenyl-2-acyloxy-ethyl,
and, where q is 2,
$R_{42}$ is alkylene, 1,4-but-2-enylene, alkylene-di-(carbonyloxyethylene), alkylene-di-(carbonyloxymethylethylene), wherein methyl is in the α-position with respect to carbonyloxy, alkylene-di-(carbonyl-phenylethylene), wherein phenyl is in the α-position with respect to carbonyloxy, alkylene-di-oxycarbonylmethyl or xylylene-di-oxycarbonylmethyl,
s is a value from 0 to 2, and
L is a singly charged anion of an anol of formula II

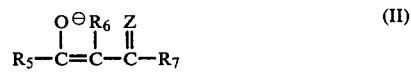

wherein Z is oxo or optionally substituted imino, $R_5$ is alkyl, alkenyl, cycloalkyl, aralkyl or aryl, $R_6$ is hydrogen, alkyl, alkenyl, cycloalkyl, aralkyl, aryl or alkoxycarbonyl, or $R_5$ and $R_6$ together are optionally substituted 1,4-butadi-1,3-enylene or 1,4-butylene, and $R_7$ is optionally substituted alkyl, alkenyl, cycloalkyl, aralkyl, aryl, alkoxy or optionally substituted amino.

57. Metal complex according to claim 56, wherein r is equal to the number of the >N-Y groups in the bracket q.

* * * * *